(12) United States Patent
Koerber et al.

(10) Patent No.: US 9,006,485 B2
(45) Date of Patent: Apr. 14, 2015

(54) ANILINE TYPE COMPOUNDS

(75) Inventors: Karsten Koerber, Eppelheim (DE); Prashant Deshmukh, Mannheim (DE); Florian Kaiser, Mannheim (DE); Michael Rack, Eppelheim (DE); Timo Frasetto, Mannheim (DE); Gemma Veitch, Basel (CH); Markus Kordes, Bobenheim-Roxheim (DE); Marco Naujok, Lustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/236,362

(22) PCT Filed: Aug. 10, 2012

(86) PCT No.: PCT/EP2012/065649
§ 371 (c)(1),
(2), (4) Date: Jan. 31, 2014

(87) PCT Pub. No.: WO2013/024008
PCT Pub. Date: Feb. 21, 2013

(65) Prior Publication Data
US 2014/0155451 A1 Jun. 5, 2014

Related U.S. Application Data

(60) Provisional application No. 61/522,752, filed on Aug. 12, 2011.

(30) Foreign Application Priority Data

Aug. 12, 2011 (EP) .................................. 11177499

(51) Int. Cl.
*C07C 313/00* (2006.01)
*A01N 41/12* (2006.01)
(Continued)

(52) U.S. Cl.
CPC ................ *A01N 43/50* (2013.01); *A01N 43/56* (2013.01); *A01N 43/80* (2013.01); *C07D 401/04* (2013.01);
(Continued)

(58) Field of Classification Search
USPC .......................................... 564/102; 514/406
See application file for complete search history.

(56) References Cited

FOREIGN PATENT DOCUMENTS

| EP | 2 143 720 | 1/2010 |
|---|---|---|
| WO | WO 01/70671 | 9/2001 |

(Continued)

OTHER PUBLICATIONS

Caira, Mino R., "Crystalline Polymorphism of Organic Compounds", Topics in Current Chemistry,1998, p. 164-208, vol. 198, Search Report.

International Preliminary Report on Patentability dated Jun. 11, 2013, prepared in International Application No. PCT/EP2012/065649.
International Search Report dated Nov. 6, 2012, prepared in International Application No. PCT/EP2012/065649.
Cho et al., "Synthesis of Pyrroloazepines. Facile Synthesis of 2-Sustituted Pyrrole Derivatives by the Phosgene Method", J. Heterocyclic Chem., vol. 34, No. 87, 1997, pp. 87-91.
(Continued)

*Primary Examiner* — Nizal Chandrakumar
(74) *Attorney, Agent, or Firm* — Brinks Gilson & Lione

(57) ABSTRACT

The present invention relates to compounds of the formula (I)

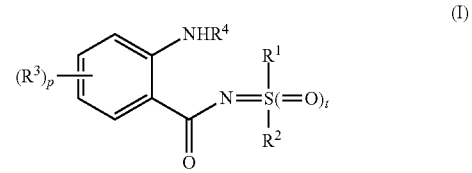

Figure 1:
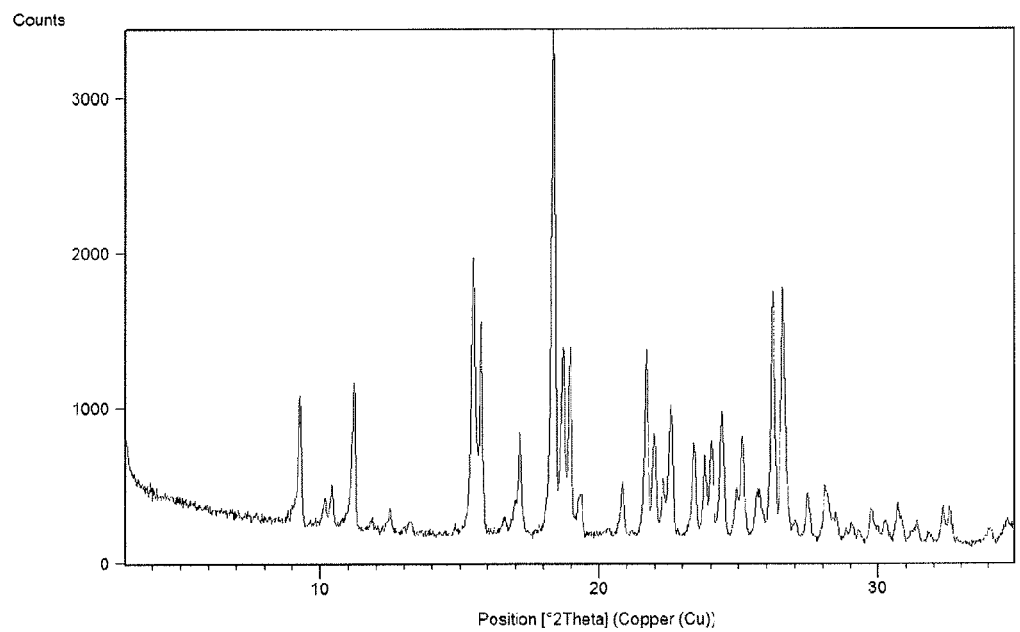

wherein
$R^1$ and $R^2$ independently of one another are hydrogen, $C_1$-$C_{10}$-alkyl, $C_1$-$C_{10}$-haloalkyl, $C_3$-$C_{10}$-cycloalkyl, $C_3$-$C_{10}$-halocycloalkyl, $C_2$-$C_{10}$-alkenyl, $C_2$-$C_{10}$-haloalkenyl or together represent an aliphatic chain, or the like; $R^3$ is halogen, cyano, $C_1$-$C_8$-alkyl, $C_1$-$C_8$-haloalkyl, $C_3$-$C_8$-cycloalkyl, $C_3$-$C_8$-halocycloalkyl, $C_2$-$C_8$-alkenyl, $C_2$-$C_8$-haloalkenyl, $C_1$-$C_8$-alkoxy, phenyl, or the like; $R^4$ is hydrogen, $C_1$-$C_{10}$-alkyl, $C_1$-$C_{10}$-haloalkyl, $C_3$-$C_8$-cycloalkyl, $C_3$-$C_8$-halocycloalkyl, $C_2$-$C_{10}$-alkenyl, $C_2$-$C_{10}$-haloalkenyl, phenyl, or the like; t is 0 or 1; p is 0, 1, 2, 3 or 4.

The present invention also relates to a process for preparing a compound of the formula (I) which comprises reacting a compound of the formula II with a compound of the formulae III or IV:

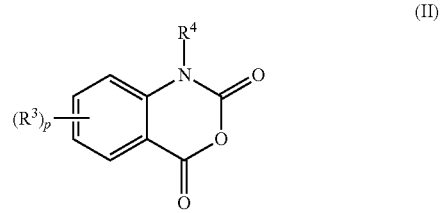

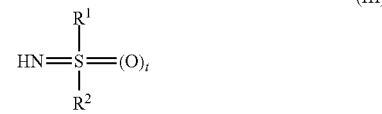

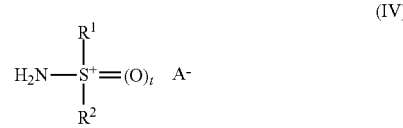

where t, p, $R^1$ $R^3$, $R^3$ and $R^4$ are as defined in any of claims 1 to 6 and where $A^-$ is an equivalent of an anion having a $pK_B$ of at least 10 (determined under standard conditions in water).

19 Claims, 2 Drawing Sheets

(51) Int. Cl.
*A01N 43/50* (2006.01)
*A01N 43/56* (2006.01)
*A01N 43/80* (2006.01)
*C07D 401/04* (2006.01)
*C07C 381/10* (2006.01)
*C07D 401/14* (2006.01)
*C07D 413/14* (2006.01)
*C07D 409/14* (2006.01)
*A01N 37/28* (2006.01)

(52) U.S. Cl.
CPC ........... C07C 381/10 (2013.01); *C07B 2200/13* (2013.01); C07D 401/14 (2013.01); C07D 413/14 (2013.01); C07D 409/14 (2013.01); A01N 37/28 (2013.01); A01N 41/12 (2013.01)

(56) References Cited

FOREIGN PATENT DOCUMENTS

| WO | WO 03/015518 | | 2/2003 | |
|---|---|---|---|---|
| WO | WO 03/016300 | | 2/2003 | |
| WO | WO 03016284 | | 2/2003 | |
| WO | WO 03/024222 | | 3/2003 | |
| WO | WO 2006/000336 | | 1/2006 | |
| WO | WO 2006/068669 | | 6/2006 | |
| WO | WO 2007/006670 | | 1/2007 | |
| WO | WO 2007006670 | * | 1/2007 | ........... C07D 401/04 |
| WO | WO 2007/043677 | | 4/2007 | |
| WO | WO 2008/011131 | | 1/2008 | |
| WO | WO 2008/130021 | | 10/2008 | |
| WO | WO 2011/064188 | | 6/2011 | |
| WO | WO 2013/024007 | | 2/2013 | |
| WO | WO 2013/024009 | | 2/2013 | |
| WO | WO 2013/024010 | | 2/2013 | |

OTHER PUBLICATIONS

Clark et al., "Synthesis of insecticidal fluorinated anthranilic diamides", Bioorganic & Medicinal Chemistry, vol. 16, 2008, pp. 3163-3170.

deGroot et al., "Synthesis and Photoisomerisation of 2,3.17,18,22-pentamethyl-10,23-dihydro-1,19-[21$H$,24$H$]-bilindione, an unsymmetrical bilirubin model compound", Journal of the Royal Netherlands Chemical Society, vol. 101, No. 6, 1982, pp. 219-223.

Gschwend et al., Organic Reactions, vol. 26, 1979, p. 26.

Lahm et al., "Insecticidal anthranilic diamides: A new class of potent ryanodine receptor activators", Bioorganic & Medicinal Chemistry Letters, vol. 15, 2005, pp. 4898-4906.

Lahm et al., "Rynaxypyr™: A new insecticidal anthranilic diamide that acts as a potent and selective ryanodine receptor activator", Bioorganic & Medicinal Chemistry Letters, vol. 17, 2007, pp. 6274-6279.

Liu et at "Design, Synthesis and Insecticidal Evaluation of Novel Pyrazolecarboxamides Containing Cyano Substituted N-Pyridylpyrazole", Chin. J. Chem., vol. 28, 2010, pp. 1757-1760.

Micetich et al., "The Sequential Lithiation of 1-Phenylpyrazoles", Heterocycles, vol. 23, No. 4, 1985, pp. 943-951.

Purandare et al., "Pyrazole inhibitors of coactivator associated arginine methyltransferase 1 (CARM1)", Bioorganic & Medicinal Chemistry Letters, vol. 18, 2008, pp. 4438-4441.

Tertov et al., "Reactions of N-Substituted Diazoles and their Halo Derivatives with Naphthyllithium and Naphthylsodium", Khimiya Geterotsiklicheskikh Soedinenii, No. 3, 1975, pp. 392-395.

* cited by examiner

ANILINE TYPE COMPOUNDS

This application is a National Stage application of International Application No. PCT/EP2012/065649, filed Aug. 10, 2012, which claims the benefit of U.S. Provisional Application No. 61/522,752, filed Aug. 12, 2011, the entire contents of which are hereby incorporated herein by reference. This application also claims priority under 35 U.S.C. §119 to European Patent Application No. 11177499.8, filed Aug. 12, 2011, the entire contents of which is hereby incorporated herein by reference.

The present invention relates to novel aniline type compounds carrying a sulf(ox)iminocarbonyl radical in the ortho position with respect to the amino group of the aniline type compounds and to a process for their preparation. The compounds are useful as intermediates in the production of novel N-(het)arylpyrazole carboxanilides carrying a sulf(ox)iminocarbonyl radical in the ortho position with respect to the amide group.

BACKGROUND OF THE INVENTION

N-(Het)arylpyrazole carboxanilides of the formula (V) carrying a sulf(ox)imino-carbonyl radical $A^1$-C(O) in the ortho position with respect to the amide group have been disclosed in WO 2007/006670:

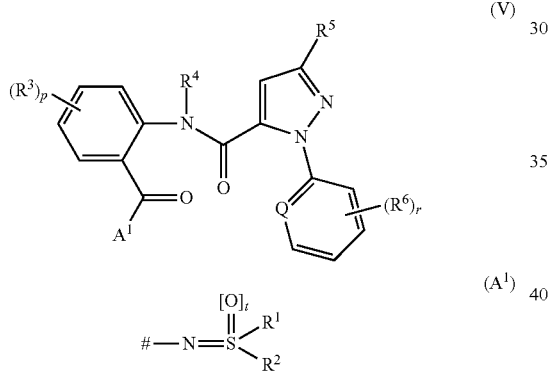

In formula V, the variables p, r, t, Q, $R^1$, $R^2$, $R^3$, $R^4$, $R^5$ and $R^6$ are as defined hereinafter and in the claims. These compounds belong to the class of anthranilamide insecticides, exemplified by cyanthraniliprole and chloranthraniliprole, and show high activity against invertebrate pests.

WO 2007/006670 teaches three synthetic routes for preparing these compounds, to be specific:

(1) Reacting a N-(het)arylpyrazole carboxanilide compound carrying an activated carboxyl group instead of the group C(O)-$A^1$ with a suitable sulfimine (NH=$SR^1R^2$) or sulfoximine (NH=S(O)$R^1R^2$);

(2) Reacting a 2-(1-(het)arylpyrazole-5-yl)-benzo[d]1,3-oxazine-4-one with a suitable sulfimine or sulfoximine;

(3) Reacting a N-(het)arylpyrazole carboxanilide compound carrying primary carboxamide group instead of the group C(O)-$A^1$ with a suitable sulfoxide (O=$SR^1R^2$).

The primary carboxamides themselves are prepared by reacting a 2-(1-(het)aryl-pyrazole-5-yl)-benzo[d]1,3-oxazine-4-one with ammonia.

According to each of these synthetic routes (1) to (3) the sulf(ox)iminocarbonyl radical $A^1$-C(O) is introduced in the very last step of the synthesis. As these routes require preformation of the major part of the N-(het)arylpyrazole carboxanilide molecule and while the yields in these lasts steps of routes (1) to (3) are only moderate, these routes are not very attractive for preparing the compounds of formula (V). Routes (2) to (3) require the synthesis of 2-(1-(het)arylpyrazole-5-yl)-benzo[d]1,3-oxazine-4-ones which are not available on large scale. Likewise, the starting compounds of route (1), i.e. N-(het)arylpyrazole carboxanilides (V), where $A^1$ is OH, are not available on large scale. Apart from that, some steps in the preparation of precursors of (V) require the use of dangerous and/or expensive reagents such organo-lithium compounds. When starting from readily available starting materials, the total number of reaction steps required for the preparation of the precursors used in routes (1) to (3) is high and overall yields are low.

Therefore, it is an object of the present invention to provide a method for the preparation of compounds of formula (V) which overcomes the problems associated with the processes of prior art. Moreover, it is a high need for a process, which can be performed on large scale and which can start from readily accessible starting materials.

SUMMARY OF INVENTION

It has now surprisingly been found that compounds of the formula V can be prepared by reacting an aniline compound of the formula I as defined hereinafter and in the claims with a suitable pyrazole derivative of the formula VI. The compounds of the formula I are novel and can surprisingly be prepared on large scale by reacting an isatoic anhydride of the formula II with a compound of the formulae III or IV as defined hereinafter and in the claims. Thus, the compound of the formula I allows a convergent synthesis of the compound of formula V in high yields from readily accessible starting materials, thereby allowing to avoid the problems associated with the processes of prior art.

Therefore, a first aspect of the invention relates to a compound of the formula (I)

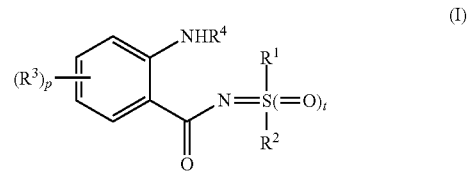

in which
t is 0 or 1;
p is 0, 1, 2, 3 or 4;
$R^1$ and $R^2$ are selected, independently of one another, from the group consisting of hydrogen, $C_1$-$C_{10}$-alkyl, $C_1$-$C_{10}$-haloalkyl, $C_3$-$C_{10}$-cycloalkyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, wherein the eight last radicals may optionally be substituted by one or more radicals $R^a$, or $R^1$ and $R^2$ together represent a $C_2$-$C_9$-alkylene, $C_2$-$C_9$-alkenylene or $C_3$-$C_9$-alkynylene chain forming together with the sulfur atom to which they are attached a 3-, 4-, 5-, 6-, 7-, 8-, 9- or 10-membered saturated, partially unsaturated or fully unsaturated ring, wherein 1 to 4 of the $CH_2$ groups in the $C_2$-$C_9$-alkylene chain or 1 to 4 of any of the $CH_2$ or CH groups in the $C_2$-$C_9$-alkenylene chain or 1 to 4 of any of the $CH_2$ groups in the $C_2$-$C_9$-alkynylene chain may be replaced by 1 to 4 groups independently selected from the group consisting of C=O, C=S, O, S, N, NO, SO, $SO_2$ and $NR^y$, and wherein the carbon atoms in the $C_2$-$C_9$-alkylene, $C_2$-$C_9$-alkenylene or $C_2$-$C_9$-alkynylene chain may be substituted with 1 to 5 identical or different substituents $R^x$, and wherein the sulfur and nitrogen atoms in the $C_2$-$C_9$-alkylene, $C_2$-$C_9$-alkenylene or $C_2$-$C_9$-alkynylene chain, independently of one another, may be oxidized;

$R^3$ if present, are independently selected from the group consisting of halogen, cyano, azido, nitro, —SCN, $SF_5$, $C_1$-$C_8$-alkyl, $C_1$-$C_8$-haloalkyl, $C_3$-$C_8$-cycloalkyl, $C_3$-$C_8$-halocycloalkyl, $C_2$-$C_8$-alkenyl, $C_2$-$C_8$-haloalkenyl, $C_2$-$C_8$-alkynyl, $C_2$-$C_8$-haloalkynyl, wherein the eight last radicals may optionally be substituted by one or more radicals $R^a$, —$OR^b$, $SR^b$, —$S(O)_mR^b$, —$S(O)_nN(R^c)R^d$, —$N(R^c)R^d$, —$Si(R^f)_2R^g$, —$N(R^c)C(=O)R^b$, —$C(=NR^c)R^b$, —$C(=O)N(R^c)R^d$, —$C(=S)N(R^c)R^d$, phenyl which may be substituted by 1, 2, 3, 4 or 5 radicals $R^e$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^e$, for p>1 it being possible that $R^3$ are identical or different, or two radicals $R^3$ bound on adjacent carbon atoms may be together a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —$C(=O)OCH_2$—, —$O(CH_2)O$—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —$C(=S)SCH_2$—, —$S(CH_2)S$—, —$CH_2CH_2NR^y$—, —$CH_2CH=N$—, —CH=CH—$NR^y$—, —CH=N—$NR^y$—, —OCH=N— and —SCH=N—, thus forming, together with the carbon atoms to which they are bound, a 5- or 6-membered ring, where the hydrogen atoms of the above groups may be replaced by one or more substituents selected from halogen, methyl, halomethyl, hydroxyl, methoxy and halomethoxy or one or more $CH_2$ groups of the above groups may be replaced by a C=O group;

$R^4$ is selected from the group consisting of hydrogen, $C_1$-$C_{10}$-alkyl, $C_1$-$C_{10}$-haloalkyl, $C_3$-$C_8$-cycloalkyl, $C_3$-$C_8$-halocycloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, wherein the eight last radicals may optionally be substituted by one or more radicals $R^a$, phenyl which may be substituted by 1, 2, 3, 4 or 5 radicals $R^e$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^e$;

$R^a$ is selected from the group consisting of cyano, azido, nitro, —SCN, $SF_5$, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —$Si(R^f)_2R^g$, —$OR^b$, —$SR^b$, —$S(O)_mR^b$, —$S(O)_nN(R^c)R^d$, —$N(R^c)R^d$, $C(=O)R^b$, $C(=O)OR^b$, —$C(=O)N(R^c)R^d$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^e$;

or two geminally bound radicals $R^a$ together form a group selected from =$CR^hR^k$, =$NR^c$, =$NOR^b$ and =$NNR^c$;

two radicals $R^a$, together with the carbon atoms to which they are bound, form a 3-, 4-, 5-, 6-, 7- or 8-membered saturated or partially unsaturated carbocyclic ring or a 3-, 4-, 5-, 6-, 7- or 8-membered saturated or partially unsaturated heterocyclic ring containing 1, 2 or 3 heteroatoms or heteroatom groups selected from N, O, S, NO, SO and $SO_2$, as ring members; where in the case of more than one $R^a$, $R^a$ can be identical or different;

$R^b$ is selected from the group consisting of hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, where the five last mentioned radicals may be unsubstituted, partially or fully halogenated and/or wherein one or two $CH_2$ groups may be replaced by a CO group; and/or may carry 1-2 radicals selected from $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkoxycarbonyl, —$Si(R^f)_2R^g$, phenyl, benzyl, pyridyl and phenoxy, it being possible for phenyl, benzyl, pyridyl and phenoxy to be unsubstituted, partially or fully halogenated and/or to carry 1-3 substituents selected from the group consisting of $C_1$-$C_6$-alkyl, $C_1$-$C_6$-haloalkyl, $C_1$-$C_6$-alkoxy, $C_1$-$C_6$ haloalkoxy and $C_1$-$C_6$-alkoxycarbonyl;

where in the case of more than one $R^b$, $R^b$ can be identical or different;

$R^c$, $R^d$ are, independently from one another, selected from the group consisting of hydrogen, cyano, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, where the five last mentioned radicals may be unsubstituted, partially or fully halogenated and/or wherein one or two $CH_2$ groups may be replaced by a CO group; and/or may carry 1 or 2 radicals selected from $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-alkoxycarbonyl, —$Si(R^f)_2R^g$, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and $C_1$-$C_6$-alkoxycarbonyl;

or $R^c$ and $R^d$, together with the nitrogen atom to which they are bound, form a 3-, 4-, 5-, 6- or 7-membered saturated, partly unsaturated or completely unsaturated N-heterocyclic ring which may contain 1 or 2 further heteroatoms selected from N, O and S as ring members, where the heterocyclic ring may carry 1, 2, 3 or 4 substituents selected from halogen, $C_1$-$C_4$-alkyl, $C_1$-$C_4$-haloalkyl, $C_1$-$C_4$-alkoxy and $C_1$-$C_4$-haloalkoxy;

$R^e$ is selected from the group consisting of hydrogen, cyano, $C_1$-$C_6$-alkyl, $C_2$-$C_6$-alkenyl, $C_2$-$C_6$-alkynyl and $C_3-C_8$-cycloalkyl, where the four last-mentioned radicals may be unsubstituted, partially or fully halogenated and/or wherein one or two $CH_2$ groups may be replaced by a CO group, and/or may carry 1-2 radicals selected from $C_1-C_4$-alkoxy, $C_1-C_6$-alkoxy, $C_1-C_6$-haloalkoxy, $C_1-C_6$-alkylthio, $C_1-C_6$-haloalkylthio, $C_1-C_6$-alkylsulfinyl, $C_1-C_6$-haloalkylsulfinyl, $C_1-C_6$-alkylsulfonyl, $C_1-C_6$-haloalkylsulfonyl, $C_1-C_6$-alkoxycarbonyl, —Si$(R^f)_2R^g$, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1-C_6$-alkyl, $C_1-C_6$-haloalkyl, $C_1-C_6$-alkoxy, $C_1-C_6$ haloalkoxy and $C_1-C_6$-alkoxycarbonyl; where in the case of more than one $R^e$, $R^e$ can be identical or different;

$R^f$, $R^g$ are, independently of each other and independently of each occurrence, selected from the group consisting of $C_1-C_4$-alkyl, $C_3-C_6$-cycloalkyl, $C_1-C_4$-alkoxy-$C_1$-$C_4$-alkyl, $C_3-C_8$-cycloalkyl-$C_1-C_4$-alkyl, phenyl and benzyl;

$R^h$, $R^k$ are, independently from one another, selected from the group consisting of hydrogen, halogen, cyano, azido, nitro, —SCN, $SF_5$, $C_1-C_6$-alkyl, $C_2-C_6$-alkenyl, $C_2-C_6$-alkynyl and $C_3-C_8$-cycloalkyl, where the four last mentioned radicals may be unsubstituted, partially or fully halogenated and/or oxgenated, and/or may carry 1 or 2 radicals selected from $C_1-C_4$-alkyl; $C_1-C_4$-haloalkyl; $C_1-C_6$-alkoxy, $C_1-C_6$-haloalkoxy, $C_1-C_6$-alkylthio, $C_1-C_6$-alkylsulfinyl, $C_1-C_6$-alkylsulfonyl, $C_1-C_6$-haloalkylthio, —Si$(R^f)_2R^g$, —OH, —SH, phenyl, benzyl, pyridyl and phenoxy, it being possible for phenyl, benzyl, pyridyl and phenoxy to be unsubstituted, partially or fully halogenated and/or to carry 1 to 3 substituents selected from the group consisting of $C_1-C_6$-alkyl, $C_1-C_6$-haloalkyl, $C_1-C_6$-alkoxy, $C_1-C_6$ haloalkoxy; ($C_1-C_6$-alkoxy)carbonyl, ($C_1-C_6$-alkyl)amino, di-($C_1-C_6$-alkyl)amino;

or $R^h$ and $R^k$ together form a group =C($C_1-C_4$-alkyl)$_2$, =N($C_1-C_6$-alkyl), =NO($C_1-C_6$-alkyl), or =O;

$R^x$ is selected from the group consisting of halogen, cyano, $C_1-C_6$-alkyl, $C_1-C_6$-haloalkyl, $C_1-C_6$-alkoxy, $C_1-C_6$-haloalkoxy, $C_1-C_6$-alkylthio, $C_1-C_6$-haloalkylthio, $C_3-C_8$-cycloalkyl, $C_3-C_8$-halocycloalkyl, $C_2-C_6$-alkenyl, $C_2-C_6$-haloalkenyl, $C_2-C_6$-alkynyl and $C_2-C_6$-haloalkynyl, said substituents $R^x$ being identical or different from one another if more than one substituent $R^x$ is present;

$R^y$ is selected from the group consisting of hydrogen, cyano, $C_1-C_6$-alkyl, $C_1-C_6$-haloalkyl, $C_1-C_6$-alkoxy, $C_1-C_6$-haloalkoxy, $C_3-C_8$-cycloalkyl, $C_3-C_8$-halocycloalkyl, $C_2-C_6$-alkenyl, $C_2-C_6$-haloalkenyl, $C_2-C_6$-alkynyl, $C_2-C_6$-haloalkynyl and $C_3-C_8$-cycloalkyl-$C_1$-$C_4$-alkyl;

m is 1 or 2, wherein, in the case of several occurrences, m may be identical or different.

n is 0, 1 or 2; wherein, in the case of several occurrences, n may be identical or different;

and the salts thereof.

The compounds of the formula I are valuable key intermediates in the preparation of pesticide compounds of the formula V. Moreover, they surprisingly possess a pesticidal activity on their part, in particular a herbicidal activity or an insecticidal activity. Moreover, the compounds of formula I are easily accessible on large scale and allow the introduction to the sulf(ox)iminocarbonyl moiety at an earlier stage of the synthesis of compounds V than the processes according to prior art.

In a second aspect, the invention relates to a process for preparing a compound of the formula I, which comprises reacting a compound of the formula II

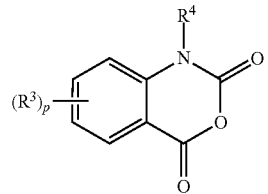

where p, $R^3$ and $R^4$ are as defined herein and in the claims with a compound of the formulae III or IV, (III)
$$HN=S(=O)_t \begin{matrix} R^1 \\ | \\ | \\ R^2 \end{matrix}$$

(IV)
$$H_2N-\overset{+}{S}(=O)_t \begin{matrix} R^1 \\ | \\ | \\ R^2 \end{matrix} \quad A^-$$

where t, $R^1$ and $R^2$ are as defined herein and in the claims and where $A^-$ is an equivalent of an anion having a $pK_B$ of at least 10, as determined under standard conditions (298 K; 1.013 bar) in water.

In a third aspect, the invention relates to a process for preparing a compound of the formula V, (V)

which process comprises the steps of i) providing a compound of the formula I or a salt thereof as described herein and in the claims, and;

ii) reacting the compound of the formula I with a compound of the formula VI:

(VI)

where t, p, $R^1$ $R^3$, $R^3$ and $R^4$ in formulae V and VI are as defined herein and in the claims, and where r is 0, 1, 2, 3 or 4;
X is a leaving group;
Q is N or CH;
$R^5$ is hydrogen, halogen, cyano, azido, nitro, —SCN, —SF$_5$, C$_1$-C$_8$-alkyl, C$_1$-C$_8$-haloalkyl, C$_3$-C$_8$-cycloalkyl, C$_3$-C$_8$-halocycloalkyl, C$_2$-C$_8$-alkenyl, C$_2$-C$_8$-haloalkenyl, C$_2$-C$_8$-alkynyl, C$_2$-C$_8$-haloalkynyl, wherein the eight last radicals may optionally be substituted by one or more radicals $R^a$, —Si(R$^f$)$_2$R$^g$, —OR$^b$, —OS(O)$_n$R$^b$, SR$^b$, —S(O)$_m$R$^b$, —S(O)$_n$N(R$^c$)R$^d$, —N(R)R$^d$, —N(R$^c$)C(=O)R$^b$, —C(=O)R$^b$, —C(=O)OR$^b$, —C(=S)R$^b$, —C(=S)OR$^b$, —C(=NR$^c$)R$^b$, —C(=O)N(R$^c$)R$^d$, —C(=S)N(R$^c$)R$^d$, phenyl which may be substituted by 1, 2, 3, 4 or 5 radicals $R^e$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^e$;
$R^6$ is selected from the group consisting of halogen, cyano, azido, nitro, —SCN, SF$_5$, C$_1$-C$_8$-alkyl, C$_1$-C$_8$-haloalkyl, C$_3$-C$_8$-cycloalkyl, C$_3$-C$_8$-halocycloalkyl, C$_2$-C$_8$-alkenyl, C$_2$-C$_8$-haloalkenyl, C$_2$-C$_8$-alkynyl, C$_2$-C$_8$-haloalkynyl, wherein the eight last radicals may optionally be substituted by one or more radicals $R^a$, —Si(R$^f$)$_2$R$^g$, —OR$^b$, —OS(O)$_n$R$^b$, SR$^b$, —S(O)$_m$R$^b$, —S(O)$_n$N(R$^c$)R$^d$, —N(R)R$^d$, —N(R$^c$)C(=O)R$^b$, —C(=O)R$^b$, —C(=O)OR$^b$, —C(=S)R$^b$, —C(=S)OR$^b$, —C(=NR$^c$)R$^b$, phenyl which may be substituted by 1, 2, 3, 4 or 5 radicals $R^e$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^e$, for r>1 it being possible that $R^6$ are identical or different, and where $R^a$, $R^b$, $R^c$, $R^d$, $R^e$, $R^f$, $R^g$, m and n are as defined herein and in the claims.

Yet, a further aspect of the present invention relates to crystalline form of 2-(3-chloro-2-pyridyl)-N-[2-methyl-4-chloro-6-[(diethyl-λ$^4$-sulfanylidene)carbamoyl]phenyl]-5-(trifluoromethyl)pyrazole-3-carboxamide which, in an X-ray powder diffractogram at 25° C. and Cu-K$_α$ radiation, shows at least four, frequently at least 5, in particular at least 7, especially at least 9 or all of the following 10 reflexes, given as 2θ values: 9.31, 11.22, 15.50, 15.79, 17.16, 18.38, 18.74, 18.98, 26.23, 26.58.

Yet, a further aspect of the present invention relates to crystalline forms I and II of 2-(3-chloro-2-pyridyl)-N-[2-methyl-4-chloro-6-[(bis-2-propyl-λ$^4$-sulfanylidene)-carbamoyl]phenyl]-5-(trifluoromethyl)pyrazole-3-carboxamide where in an X-ray powder diffractogram at 25° C. and Cu—K$_α$ radiation, form I shows at least four, frequently at least 5, in particular at least 7, especially at least 9 or all of the following 10 reflexes, given as 2θ values: 8.64, 10.05, 10.23, 13.09, 13.48, 15.11, 15.89, 16.43, 17.68, 18.35;
and where form II shows at least four, frequently at least 5, in particular at least 7, especially at least 9 or all of the following 10 reflexes, given as 2θ values: 8.96, 9.23, 10.37, 12.40, 13.36, 13.67, 16.00, 17.90, 18.22, 20.80.

DETAILED DESCRIPTION OF THE INVENTION

Depending on the substitution pattern, the compounds of the formula (I) may have one or more centers of chirality, in which case they are present as mixtures of enantiomers or diastereomers. The invention provides both the pure enantiomers or pure diastereomers of the compounds of formula (I), and their mixtures and the use according to the invention of the pure enantiomers or pure diastereomers of the compound of formula (I) or its mixtures. Suitable compounds of the formula (I) also include all possible geometrical stereoisomers (cis/trans isomers) and mixtures thereof. Cis/trans isomers may be present with respect to an alkene, carbon-nitrogen double-bond, nitrogen-sulfur double bond or amide group. The term "stereoisomer(s)" encompasses both optical isomers, such as enantiomers or diastereomers, the latter existing due to more than one center of chirality in the molecule, as well as geometrical isomers (cis/trans isomers).

The compounds of the present invention may be amorphous or may exist in one ore more different crystalline states (polymorphs) which may have different macroscopic properties such as stability or show different biological properties such as activities. The present invention includes both amorphous and crystalline compounds of formula (I), their enantiomers or diastereomers, mixtures of different crystalline states of the respective compound of formula (I), its enantiomers or diastereomers, as well as amorphous or crystalline salts thereof.

Salts of the compounds of the present invention are preferably agriculturally and veterinarily acceptable salts. They can be formed in a customary method, e.g. by reacting the compound with an acid if the compound of the present invention has a basic functionality or by reacting the compound with a suitable base if the compound of the present invention has an acidic functionality.

Suitable salts are especially the salts of those cations or the acid addition salts of those acids whose cations and anions, respectively, do not have any adverse effect on the pesticidal action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium (NH$_4^+$) and substituted ammonium in which one to four of the hydrogen atoms are replaced by C$_1$-C$_4$-alkyl, C$_1$-C$_4$-hydroxyalkyl, C$_1$-C$_4$-alkoxy, C$_1$-C$_4$-alkoxy-C$_1$-C$_4$-alkyl, hydroxy-C$_1$-C$_4$-alkoxy-C$_1$-C$_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyltriethylammonium, furthermore phosphonium ions, sulfonium ions, preferably tri(C$_1$-C$_4$-alkyl)sulfonium, and sulfoxonium ions, preferably tri(C$_1$-C$_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of C$_1$-C$_4$-alkanoic acids, preferably formate, acetate, propionate and butyrate. They can be formed by reacting compounds of the present invention with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix C$_n$-C$_m$ indicates in each case the possible number of carbon atoms in the group.

The term halogen denotes in each case fluorine, bromine, chlorine or iodine, in particular fluorine, chlorine or bromine.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "alkyl" as used herein (and in the alkyl moieties of other groups comprising an alkyl group, e.g. alkoxy, alkylcarbonyl, alkylthio, alkylsulfinyl, alkylsulfonyl and alkoxyalkyl) denotes in each case a straight-chain or branched alkyl group having usually from 1 to 10 carbon atoms, frequently from 1 to 8 or from carbon atoms, preferably 1 to 4 carbon atoms and in particular from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methyloctyl, 2-methylheptyl, 1-ethylhexyl, 2-ethylhexyl, 1,2-dimethylhexyl, 1-propylpentyl and 2-propylpentyl.

The term "haloalkyl" as used herein (and in the haloalkyl moieties of other groups comprising a haloalkyl group, e.g. haloalkoxy and haloalkylthio) denotes in each case a straight-chain or branched alkyl group having usually from 1 to 10 carbon atoms, frequently from 1 to 8 or from 1 to 6 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, more preferably from halomethyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "cycloalkyl" as used herein (and in the cycloalkyl moieties of other groups comprising a cycloalkyl group, e.g. cycloalkoxy and cycloalkylalkyl) denotes in each case a mono- or bicyclic cycloaliphatic radical having usually from 3 to 10 carbon atoms, 3 to 8 carbon atoms or 3 to 6 carbon atoms, such as cyclopropyl, cyclobutyl, cyclopentyl, cyclohexyl, cycloheptyl, cyclooctyl, bicyclo[2.1.1]hexyl, bicyclo[3.1.1]heptyl, bicyclo[2.2.1]heptyl, and bicyclo[2.2.2]octyl.

The term "halocycloalkyl" as used herein (and in the halocycloalkyl moieties of other groups comprising an halocycloalkyl group, e.g. halocycloalkylmethyl) denotes in each case a mono- or bicyclic cycloaliphatic radical having usually from 3 to 10 carbon atoms, 3 to 8 carbon atoms or 3 to 6 carbon atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-, 2- and 3-fluorocyclopentyl, 1,2-, 2,2-, 2,3-, 3,3-, 3,4-, 2,5-difluorocyclopentyl, 1-, 2- and 3-chlorocyclopentyl, 1,2-, 2,2-, 2,3-, 3,3-, 3,4-, 2,5-dichlorocyclopentyl and the like.

The term "alkenyl" as used herein in each case denotes a singly unsaturated hydrocarbon radical having usually 2 to 10, frequently from 2 to 8 or from 2 to 6 carbon atoms, preferably 2 to 4 carbon atoms, e.g. vinyl, allyl(2-propen-1-yl), 1-propen-1-yl, 2-propen-2-yl, methallyl(2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "haloalkenyl" as used herein, which may also be expressed as "alkenyl which may be substituted by halogen", and the haloalkenyl moieties in haloalkenyloxy, haloalkenylcarbonyl and the like refers to unsaturated straight-chain or branched hydrocarbon radicals having 2 to 10 ("$C_2$-$C_{10}$-haloalkenyl") or 2 to 6 ("$C_2$-$C_6$-haloalkenyl") carbon atoms and a double bond in any position, where some or all of the hydrogen atoms in these groups are replaced by halogen atoms as mentioned above, in particular fluorine, chlorine and bromine, for example chlorovinyl, chloroallyl and the like.

The term "alkynyl" as used herein denotes unsaturated straight-chain or branched hydrocarbon radicals having usually 2 to 10, frequently 2 to 8 or 2 to 6 carbon atoms, preferably 2 to 4 carbon atoms and one or two triple bonds in any position, e.g. ethynyl, propargyl(2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term haloalkynyl as used herein, which is also expressed as "alkynyl which may be substituted by halogen", refers to unsaturated straight-chain or branched hydrocarbon radicals having usually 3 to 10 carbon atoms, frequently 2 to 6, preferably 2 to 4 carbon atoms, and one or two triple bonds in any position (as mentioned above), where some or all of the hydrogen atoms in these groups are replaced by halogen atoms as mentioned above, in particular fluorine, chlorine and bromine.

The term "cycloalkyl-alkyl" used herein denotes a cycloalkyl group, as defined above, which is bound to the remainder of the molecule via an alkylene group having preferably from 1 to 4 carbon atoms. Examples are cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, and the like.

The term "alkylene" (or alkanediyl) as used herein in each case denotes an alkyl radical as defined above having usually from 2 to 9 or from 3 to 7 or from 3 to 5 carbon atoms, wherein one hydrogen atom at any position of the alkyl group is replaced by one further binding site, thus forming a bivalent moiety.

The term "alkenylene" (or alkenediyl) as used herein in each case denotes an alkenyl radical as defined above having usually from 2 to 9 or from 3 to 7 or from 3 to 5 carbon atoms, wherein one hydrogen atom at any position of the carbon backbone is replaced by one further binding site, thus forming a bivalent moiety.

The term "alkynylene" (or alkynediyl) as used herein in each case denotes an alkynyl radical as defined above having usually from 3 to 9 or from 3 to 7 or from 3 to 5 carbon atoms, wherein one hydrogen atom at any position of the carbon backbone is replaced by one further binding site, thus forming a bivalent moiety.

The term "alkoxy" as used herein denotes in each case a straight-chain or branched alkyl group usually having from 1 to 10 carbon atoms, frequently from 1 to 6 carbon atoms, preferably 1 to 4 carbon atoms, which is bound to the remainder of the molecule via an oxygen atom. Examples of an alkoxy group are methoxy, ethoxy, n-propoxy, iso-propoxy, n-butyloxy, 2-butyloxy, iso-butyloxy, tert-butyloxy, and the like.

The term "haloalkoxy" as used herein denotes in each case a straight-chain or branched alkoxy group, as defined above, having from 1 to 10 carbon atoms, frequently from 1 to 6 carbon atoms, preferably 1 to 4 carbon atoms, preferably 1 to 3 carbon atoms, wherein the hydrogen atoms of this group are partially or totally replaced with halogen atoms, in particular fluorine atoms. Preferred haloalkoxy moieties include $C_1$-$C_4$-haloalkoxy, in particular halomethoxy, and also in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2-dichloro-2-fluorethoxy, 2,2,2-trichloroethoxy, pentafluoroethoxy and the like.

The term "alkoxy-alkyl" as used herein denotes in each case alkyl usually comprising 1 to 6 carbon atoms, preferably 1 to 4 carbon atoms, wherein 1 carbon atom carries an alkoxy radical usually comprising 1 to 10, frequently 1 to 6, in particular 1 to 4, carbon atoms as defined above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methyl-propoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)-butyl, 3-(2-methylpropoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "alkylthio" (also alkylsulfanyl or alkyl-S—)" as used herein denotes in each case a straight-chain or branched saturated alkyl group as defined above, usually comprising 1 to 10 carbon atoms, frequently comprising 1 to 6 carbon atoms, preferably 1 to 4 carbon atoms, which is attached via a sulfur atom at any position in the alkyl group. Examples are methylthio, ethylthio, n-propylthio, iso-propylthio, n-butylthio, 2-butylthio, iso-butylthio, tert-butylthio, and the like.

The term "haloalkylthio" as used herein refers to an alkylthio group as defined above wherein the hydrogen atoms are partially or fully substituted by fluorine, chlorine, bromine and/or iodine. Examples are fluoromethylthio, difluoromethylthio, trifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoro-ethylthio, 2,2-dichloro-2-fluorethylthio, 2,2,2-trichloroethylthio, pentafluoroethylthio and the like The terms "alkylsulfinyl" and "$S(O)_n$-alkyl" (wherein n is 1) are equivalent and, as used herein, denote an alkyl group, as defined above, attached via a sulfinyl [S(O)] group. For example, the term "$C_1$-$C_6$-alkylsulfinyl" refers to a $C_1$-$C_6$-alkyl group, as defined above, attached via a sulfinyl [S(O)] group. Examples are methylsulfinyl, ethylsulfinyl, n-propylsulfinyl, 1-methylethylsulfinyl(isopropylsulfinyl), butylsulfinyl, 1-methylpropylsulfinyl(sec-butylsulfinyl), 2-methylpropylsulfinyl(isobutylsulfinyl), 1,1-dimethylethylsulfinyl(tert-butylsulfinyl), pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl.

The terms "alkylsulfonyl" and "$S(O)_n$-alkyl" (wherein n is 2) are equivalent and, as used herein, denote an alkyl group, as defined above, attached via a sulfonyl [$S(O)_2$] group. For example, the term "$C_1$-$C_6$-alkylsulfonyl" refers to a $C_1$-$C_6$-alkyl group, as defined above, attached via a sulfonyl [$S(O)_2$] group. Examples are methylsulfonyl, ethylsulfonyl, n-propylsulfonyl, 1-methylethylsulfonyl(isopropylsulfonyl), butylsulfonyl, 1-methylpropylsulfonyl(sec-butylsulfonyl), 2-methylpropylsulfonyl(isobutylsulfonyl), 1,1-dimethylethylsulfonyl(tert-butylsulfonyl), pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

The term "alkylamino" as used herein denotes in each case a group —NHR, wherein R is a straight-chain or branched alkyl group usually having from 1 to 6 carbon atoms, preferably 1 to 4 carbon atoms. Examples of an alkylamino group are methylamino, ethylamino, n-propylamino, isopropylamino, n-butylamino, 2-butylamino, iso-butylamino, tert-butylamino, and the like.

The term "dialkylamino" as used herein denotes in each case a group-NRR', wherein R and R', independently of each other, are a straight-chain or branched alkyl group each usually having from 1 to 6 carbon atoms, preferably 1 to 4 carbon atoms. Examples of a dialkylamino group are dimethylamino, diethylamino, dipropylamino, dibutylamino, methyl-ethyl-amino, methyl-propyl-amino, methyl-isopropylamino, methyl-butyl-amino, methyl-isobutyl-amino, ethyl-propyl-amino, ethyl-isopropylamino, ethyl-butyl-amino, ethyl-isobutyl-amino, and the like.

The suffix "-carbonyl" in a group denotes in each case that the group is bound to the remainder of the molecule via a carbonyl C=O group. This is the case e.g. in alkylcarbonyl, haloalkylcarbonyl, alkoxycarbonyl and haloalkoxycarbonyl.

The term "3-, 4-, 5-, 6-, 7- or 8-membered saturated, partially unsaturated or completely unsaturated heterocyclic ring containing 1, 2 or 3 heteroatoms or heteroatom groups selected from N, O, S, NO, SO and $SO_2$, as ring members" [wherein "completely/fully unsaturated" includes also "aromatic"] as used herein denotes monocyclic radicals, the monocyclic radicals being saturated, partially unsaturated or fully unsaturated (including aromatic) and which in addition to carbon atoms carry at least one, namely 1, 2 or 3 heteroatoms or heteroatom groups as ring members. The heterocyclic ring may be attached to the remainder of the molecule via a carbon ring member or via a nitrogen ring member. In the latter case, the heterocyclic ring is also termed as an N-heterocyclic ring.

Examples of a 3-, 4-, 5-, 6-, 7- or 8-membered saturated heterocyclic ring include: oxiranyl, aziridinyl, azetidinyl, tetrahydrofuran-2-yl, tetrahydrofuran-3-yl, tetrahydrothien-2-yl, tetrahydrothien-3-yl, pyrrolidin-2-yl, pyrrolidin-3-yl, pyrazolidin-3-yl, pyrazolidin-4-yl, pyrazolidin-5-yl, imidazolidin-2-yl, imidazolidin-4-yl, oxazolidin-2-yl, oxazolidin-4-yl, oxazolidin-5-yl, isoxazolidin-3-yl, isoxazolidin-4-yl, isoxazolidin-5-yl, thiazolidin-2-yl, thiazolidin-4-yl, thiazolidin-5-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-2-yl, 1,3,5-hexahydrotriazin-2-yl and 1,2,4-hexahydrotriazin-3-yl, morpholin-2-yl, morpholin-3-yl, thiomorpholin-2-yl, thiomorpholin-3-yl, 1-oxothiomorpholin-2-yl, 1-oxothiomorpholin-3-yl, 1,1-dioxothiomorpholin-2-yl, 1,1-dioxothiomorpholin-3-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

A 3-, 4-, 5-, 6-, 7- or 8-membered completely unsaturated (including aromatic) heterocyclic ring is e.g. a 5- or 6-membered fully unsaturated (including aromatic) heterocyclic ring. Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 4-isoxazolyl, 2-thiazolyl, 4-thiazolyl, 5-thiazolyl, 4-isothiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The term "3-, 4-, 5-, 6-, 7- or 8-membered saturated carbocyclic ring" as used herein refers to carbocyclic rings, which are monocyclic and fully saturated. Examples of such rings include cyclopropane, cyclobutane, cyclopentane, cyclohexane, cycloheptane, cyclooctane and the like.

The terms "3-, 4-, 5-, 6-, 7- or 8-membered partially unsaturated carbocyclic ring" and "5- or 6-membered partially unsaturated carbocyclic ring" refer to carbocyclic rings, which are monocyclic and have one or more degrees of unsaturation. Examples of such rings include cyclopropene, cyclobutene, cyclopentene, cyclohexene, cycloheptene, cyclooctene and the like.

The term "a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members" as used herein denotes a saturated or unsaturated 3- to 8-membered ring system which optionally contains 1 to 3 heteroatoms selected from N, O, S, NO, SO and $SO_2$, as defined above, with the exception of the completely unsaturated ring systems.

The remarks made below as to preferred embodiments of the variables (substituents) of the compounds of formula (I) are valid on their own as well as preferably in combination with each other, as well as in combination with the stereoisomers, salts, tautomers or N-oxides thereof.

The remarks made below concerning preferred embodiments of the variables further are valid d on their own as well as preferably in combination with each other concerning the compounds of formula I as well as concerning the methods according to the invention and thus, also concerning the compounds of formulae II, III, IV, V and VI.

As a matter of course, the p radicals $R^3$ in formulae I, II and V replace a hydrogen atom on a carbon ring atom. If there is more than one radical $R^3$, i.e. p is 2 or higher, these radicals $R^3$ can be the same or different.

As a matter of course, the r radicals $R^6$ in formulae V and VI replace a hydrogen atom on a carbon ring atom. For instance, if Q is defined to be CH and if this position is to be substituted by a radical $R^6$, then Q is of course C—$R^6$. If there is more than one radical $R^6$, i.e. r is 2 or higher, these can be the same or different.

A preferred compound according to the invention is a compound of formula (I) or salt thereof, wherein the salt is an agriculturally or veterinarily acceptable salt.

In formula I and likewise in formulae III, IV and V, the variable t is preferably 0.

In particular embodiments of the compounds of formula I and likewise in particular embodiments of the compounds of formulae III, IV and V, $R^1$ and $R^2$, independently of each other, are preferably selected from the group consisting of $C_1$-$C_8$-alkyl, $C_1$-$C_8$-haloalkyl, $C_3$-$C_8$-cycloalkyl, $C_3$-$C_8$-halocycloalkyl, $C_2$-$C_8$-alkenyl, $C_2$-$C_8$-haloalkenyl, wherein alkyl, alkenyl and cycloalkyl may optionally be substituted by one or more, e.g. 1 or 2 radicals $R^a$.

In this context $R^a$ is preferably selected from the group consisting of cyano, $SF_5$, $C_3$-$C_8$-cycloalkyl, $C_3$-$C_8$-halocycloalkyl, $-Si(R^f)_2R^g$, $-OR^b$, $-SR^b$, $-S(O)_mR^b$, $-S(O)_nN(R)R^d$, $-N(R^c)R^d$, $-C(=O)N(R)R^d$, and phenyl which is unsubstituted or may be substituted by 1, 2, 3, 4 or 5 radicals $R^e$.

In particular embodiments of the compounds of formula I and likewise in particular embodiments of the compounds of formulae III, IV and V, $R^1$ and $R^2$, independently of each other, are more preferably selected from the group consisting of $C_1$-$C_6$-alkyl, $C_3$-$C_7$-cycloalkyl and $C_3$-$C_8$-cycloalkyl-$C_1$-$C_4$-alkyl.

In other particular embodiments of the compounds of formula I and likewise in particular embodiments of the compounds of formulae III, IV and V, $R^1$ and $R^2$ together represent a $C_3$-$C_7$-alkylene or $C_3$-$C_7$-alkenylene group forming together with the sulfur atom to which they are attached a 4-, 5-, 6-, 7- or 8-membered, in particular a 5-, 6 or 7-membered, saturated or partially unsaturated ring, wherein 1 or 2 of the $CH_2$ groups in the $C_3$-$C_7$-alkylene chain or 1 or 2 of any of the $CH_2$ or CH groups in the $C_3$-$C_7$-alkenylene chain may be replaced may be replaced by 1 or 2 groups independently selected from the group consisting of O, S and $NR^y$, and wherein the carbon atoms in the $C_3$-$C_7$-alkylene or $C_3$-$C_7$-alkenylene chain may be substituted with 1 to 5 identical or different substituents $R^x$, i.e. each of the carbon atoms may be unsubstituted or may carry 1 or 2 substituents $R^x$ with a maximum of 5 substituents $R^x$, in particular with a maximum of 2 substituents $R^x$ per alkylene or alkenylene chain. In these particular embodiments of formulae I, III, IV and V, $R^1$ and $R^2$ together preferably represent a $C_4$-$C_7$-alkylene group forming together with the sulfur atom to which they are attached a 5-, 6-, 7- or 8-membered, in particular a 5-, 6 or 7-membered, saturated ring.

In this context, $R^x$ is preferably selected from the group consisting of halogen and $C_1$-$C_4$-alkyl, in particular from the group consisting of fluorine chlorine and methyl.

In this context, $R^y$ is preferably $C_1$-$C_4$-alkyl, in particular methyl.

In formula I and likewise in formulae II and V, the variable p is preferably 0, 1 or 2, in particular 1 or 2.

If present, i.e. if in formulae I, II and V, the variable p is ≠0, at least one radical $R^3$ is preferably located in ortho- or para position with regard to the group $NHR^4$. If p is 1, the one radical $R^3$ in formulae I and V is preferably located in ortho- or para position with regard to the group $NHR^4$. If p is 2, one radical $R^3$ in formulae I and V is preferably located in ortho position while the other radical $R^3$ is preferably located in para position with regard to the group $NHR^4$.

In formulae I, II and V the radical $R^3$, if present, is preferably selected from the group consisting of halogen, $C_1$-$C_4$-alkyl, $C_1$-$C_4$-haloalkyl and cyano, for p>1 it being possible that $R^3$ are identical or different. In formulae I and V the radical $R^3$, if present, is in particular selected from the group consisting of halogen, in particular chlorine or bromine, methyl, cyano and halomethyl, e.g. trifluoromethyl, difluoromethyl or bromodifluoromethyl, for p>1 it being possible that $R^3$ are identical or different.

In formulae I, II and V the radical $R^4$ is preferably selected from the group consisting of $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl and hydrogen. In formulae I, II and V the radical $R^4$ is in particular hydrogen.

Particular preference is given to compounds of the formula I with t=0, wherein p is 0, 1 or 2 and for p=1, the one radical $R^3$ is located in ortho- or para position with regard to the group $NHR^4$ while for p=2, one radical $R^3$ is located in ortho position while the other radical $R^3$ is located in para position with regard to the group $NHR^4$.

Particular preferred compounds of the formula I are represented by the following formula Ia

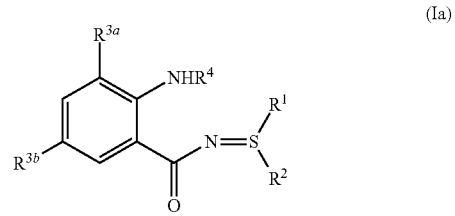

(Ia)

where $R^1$ and $R^2$ and $R^4$ are as defined herein and where $R^{3a}$ is hydrogen or has one of the meanings given herein for $R^3$ and $R^{3b}$ is hydrogen or has one of the meanings given herein for $R^3$.

In formula Ia the radical $R^{3a}$ and $R^{3b}$ are, independently of each other, preferably selected from the group consisting of hydrogen, halogen, $C_1$-$C_4$-alkyl, $C_1$-$C_4$-haloalkyl and cyano, it being possible that $R^{3a}$ and $R^{3b}$ are identical or different. In formula Ia the radical $R^{3a}$ is in particular selected from the group consisting of hydrogen, halogen, in particular chlorine or bromine, methyl, and halomethyl, e.g. trifluoromethyl, difluoromethyl or bromodifluoromethyl. In formula Ia the radical $R^{3b}$ is in particular selected from the group consisting of hydrogen, halogen, in particular chlorine or bromine, cyano, methyl, and halomethyl, e.g. trifluoromethyl, difluoromethyl or bromodifluoromethyl. In formula Ia, $R^4$ is in particular hydrogen.

In particular embodiments of the compounds of formula Ia, $R^1$ and $R^2$, independently of each other, are preferably selected from the group consisting of $C_1$-$C_8$-alkyl, $C_1$-$C_8$-haloalkyl, $C_3$-$C_8$-cycloalkyl, $C_3$-$C_8$-halocycloalkyl, $C_2$-$C_8$-alkenyl, $C_2$-$C_8$-haloalkenyl, wherein alkyl, alkenyl and cycloalkyl may optionally be substituted by one or more, e.g. 1 or 2 radicals $R^a$. In this context $R^a$ is preferably selected from the group consisting of cyano, $SF_5$, $C_3$-$C_8$-cycloalkyl, $C_3$-$C_8$-halocycloalkyl, $-Si(R^f)_2R^g$, $-OR^b$, $-SR^b$, $-S(O)_mR^b$, $-S(O)_nN(R^c)R^d$, $-N(R^c)R^d$, $-C(=O)N(R^c)R^d$, and phenyl which is unsubstituted or may be substituted by 1, 2, 3, 4 or 5 radicals $R^e$.

In particular embodiments of the compounds of formula Ia, $R^1$ and $R^2$, independently of each other, are more preferably selected from the group consisting of $C_1$-$C_6$-alkyl, $C_3$-$C_7$-cycloalkyl and $C_3$-$C_8$-cycloalkyl-$C_1$-$C_4$-alkyl.

In other particular embodiments of the compounds of formula Ia, $R^1$ and $R^2$ together represent a $C_3$-$C_7$-alkylene or $C_3$-$C_7$-alkenylene group forming together with the sulfur atom to which they are attached a 4-, 5-, 6-, 7- or 8-membered, in particular a 5-, 6 or 7-membered, saturated or partially unsaturated ring, wherein 1 or 2 of the $CH_2$ groups in the $C_3$-$C_7$-alkylene chain or 1 or 2 of any of the $CH_2$ or CH groups in the $C_3$-$C_7$-alkenylene chain may be replaced may be replaced by 1 or 2 groups independently selected from the group consisting of O, S and $NR^y$, and wherein the carbon atoms in the $C_3$-$C_7$-alkylene or $C_3$-$C_7$-alkenylene chain may be substituted with 1 to 5 identical or different substituents $R^x$, i.e. each of the carbon atoms may be unsubstituted or may carry 1 or 2 substituents $R^x$ with a maximum of 5 substituents $R^x$, in particular with a maximum of 2 substituents $R^x$ per alkylene or alkenylene chain. In this context, $R^x$ is preferably selected from the group consisting of halogen and $C_1$-$C_4$-alkyl, in particular from the group consisting of fluorine chlorine and methyl. In this context, $R^y$ is preferably $C_1$-$C_4$-alkyl, in particular methyl. In this particular embodiment of formula Ia, $R^1$ and $R^2$ together preferably represent a $C_4$-$C_7$-alkylene group forming together with the sulfur atom to which they are attached a 5-, 6-, 7- or 8-membered, in particular a 5-, 6 or 7-membered, saturated ring.

Apart from that, the variables $R^a$, $R^b$, $R^c$, $R^d$, $R^e$, $R^f$, $R^g$, $R^h$, $R^k$, $R^x$ and $R^y$, irrespectively of their occurrence, preferably have the following meanings, individually or in combination:

$R^a$ selected from the group consisting of cyano, $SF_5$, $C_3$-$C_8$-cycloalkyl, $C_3$-$C_8$-halocycloalkyl, —$Si(R^f)_2R^g$, —$OR^b$, —$SR^b$, —$S(O)_mR^b$, —$S(O)_nN(R^c)R^d$, —$N(R)R^d$, —$C(=O)N(R)R^d$, and phenyl which is unsubstituted or may be substituted by 1, 2, 3, 4 or 5 radicals $R^e$, where $R^b$, $R^c$, $R^d$, $R^e$, $R^f$ and $R^g$ are as defined herein. $R^a$ is preferably selected from the group consisting of cyano, $C_3$-$C_8$-cycloalkyl, $C_1$-$C_4$-alkoxy, $C_1$-$C_4$-alkylcarbonyl, $C_1$-$C_4$-alkoxycarbonyl, $C_1$-$C_4$-alkylthio, $C_1$-$C_4$-alkylsulfonyl, —$S(O)_nN(R^c)R^d$, —$N(R^c)R^d$ and —$C(=O)N(R^c)R^d$;

$R^b$ selected from the group consisting of $C_1$-$C_4$-alkyl, $C_1$-$C_4$-haloalkyl, $C_3$-$C_8$-cycloalkyl, phenyl and benzyl;

$R^c$ selected from the group consisting of hydrogen, $C_1$-$C_4$-alkyl, $C_1$-$C_4$-haloalkyl, $C_1$-$C_4$-alkoxy, $C_3$-$C_8$-cycloalkyl, $C_3$-$C_8$-cycloalkyl-$CH_2$, phenyl and benzyl;

$R^d$ selected from the group consisting of hydrogen, cyano, $C_1$-$C_4$-alkyl, $C_1$-$C_4$-haloalkyl, $C_1$-$C_4$-alkoxy, $C_3$-$C_8$-cycloalkyl, $C_3$-$C_8$-cycloalkyl-$CH_2$, phenyl and benzyl;

$R^c$,$R^d$ together with the nitrogen atom, to which they are bound may form a saturated 5-, 6- or 7-membered N-heterocycle, which may contain 1 or 2 further heteroatoms selected from N, O and S as ring members, where the heterocyclic ring may carry 1, 2, 3 or 4 substituents selected from $C_1$-$C_4$-alkyl;

$R^e$ selected from the group consisting of halogen, in particular fluorine, chlorine or bromine, cyano, $C_1$-$C_4$-alkyl, $C_1$-$C_4$-haloalkyl, $C_1$-$C_4$-alkoxy, $C_1$-$C_4$-haloalkoxy and $C_1$-$C_4$-alkoxycarbonyl, especially from the group consisting of halogen, in particular fluorine, chlorine or bromine, cyano, methyl, methoxy, halomethyl, e.g. trifluoromethyl, difluoromethyl or bromodifluoromethyl, and halomethoxy, e.g. trifluoromethoxy, difluoromethoxy or fluoromethoxy;

$R^f$ $C_1$-$C_4$-alkyl, in particular methyl;

$R^g$ $C_1$-$C_4$-alkyl, in particular methyl, $C_5$-$C_6$-cycloalkyl, $C_1$-$C_4$-alkoxy-$C_1$-$C_4$-alkyl, $C_5$-$C_6$-cycloalkyl-$CH_2$ and phenyl;

$R^h$ selected from the group consisting of hydrogen, halogen, cyano and $C_1$-$C_6$-alkyl;

$R^k$ selected from the group consisting of hydrogen, halogen, cyano and $C_1$-$C_6$-alkyl;

$R^x$ selected from the group consisting of halogen and $C_1$-$C_4$-alkyl, in particular from the group consisting of fluorine chlorine and methyl.

$R^y$ $C_1$-$C_4$-alkyl, in particular methyl.

Particular examples of compounds of the formula I are given in the following tables 1 to 46:

Table 1 Compounds of the formula Ia in which $R^{3a}$ and $R^{3b}$ are hydrogen, and the combination of $R^1$, $R^2$ and $R^4$ for a compound corresponds in each case to one row of Table A;

Table 2 Compounds of the formula Ia in which $R^{3a}$ is methyl, $R^{3b}$ is hydrogen, and the combination of $R^1$, $R^2$ and $R^4$ for a compound corresponds in each case to one row of Table A;

Table 3 Compounds of the formula Ia in which $R^{3a}$ is Cl, $R^{3b}$ is hydrogen, and the combination of $R^1$, $R^2$ and $R^4$ for a compound corresponds in each case to one row of Table A;

Table 4 Compounds of the formula Ia in which $R^{3a}$ is Br, $R^{3b}$ is hydrogen, and the combination of $R^1$, $R^2$ and $R^4$ for a compound corresponds in each case to one row of Table A;

Table 5 Compounds of the formula Ia in which $R^{3a}$ is hydrogen, $R^{3b}$ is methyl, and the combination of $R^1$, $R^2$ and $R^4$ for a compound corresponds in each case to one row of Table A;

Table 6 Compounds of the formula Ia in which $R^{3a}$ is hydrogen, $R^{3b}$ is Cl, and the combination of $R^1$, $R^2$ and $R^4$ for a compound corresponds in each case to one row of Table A;

Table 7 Compounds of the formula Ia in which $R^{3a}$ is hydrogen, $R^{3b}$ is Br, and the combination of $R^1$, $R^2$ and $R^4$ for a compound corresponds in each case to one row of Table A;

Table 8 Compounds of the formula Ia in which $R^{3a}$ is hydrogen, $R^{3b}$ is CN, and the combination of $R^1$, $R^2$ and $R^4$ for a compound corresponds in each case to one row of Table A;

Table 9 Compounds of the formula Ia in which $R^{1a}$ is methyl, $R^{1b}$ is methyl, and the combination of $R^1$, $R^2$ and $R^4$ for a compound corresponds in each case to one row of Table A;

Table 10 Compounds of the formula Ia in which $R^{3a}$ is Cl, $R^{3b}$ is methyl, and the combination of $R^1$, $R^2$ and $R^4$ for a compound corresponds in each case to one row of Table A;

Table 11 Compounds of the formula Ia in which $R^{3a}$ is methyl, $R^{3b}$ is Cl, and the combination of $R^1$, $R^2$ and $R^4$ for a compound corresponds in each case to one row of Table A;

Table 12 Compounds of the formula Ia in which $R^{3a}$ is Br, $R^{3b}$ is methyl, and the combination of $R^1$, $R^2$ and $R^4$ for a compound corresponds in each case to one row of Table A;

Table 13 Compounds of the formula Ia in which $R^{3a}$ is methyl, $R^{3b}$ is Br, and the combination of $R^1$, $R^2$ and $R^4$ for a compound corresponds in each case to one row of Table A;

Table 14 Compounds of the formula Ia in which $R^{3a}$ is methyl, $R^{3b}$ is CN, and the combination of $R^1$, $R^2$ and $R^4$ for a compound corresponds in each case to one row of Table A;

Table 15 Compounds of the formula Ia in which $R^{3a}$ is Cl, $R^{3b}$ is Cl, and the combination of $R^1$, $R^2$ and $R^4$ for a compound corresponds in each case to one row of Table A;

Table 16 Compounds of the formula Ia in which $R^{3a}$ is Br, $R^{3b}$ is Cl, and the combination of $R^1$, $R^2$ and $R^4$ for a compound corresponds in each case to one row of Table A;

Table 17 Compounds of the formula Ia in which $R^{3a}$ is Cl, $R^{3b}$ is Br, and the combination of $R^1$, $R^2$ and $R^4$ for a compound corresponds in each case to one row of Table A;

Table 18 Compounds of the formula Ia in which $R^{3a}$ is Cl, $R^{3b}$ is CN, and the combination of $R^1$, $R^2$ and $R^4$ for a compound corresponds in each case to one row of Table A;

Table 19 Compounds of the formula Ia in which $R^{3a}$ is Br, $R^{3b}$ is Br, and the combination of $R^1$, $R^2$ and $R^4$ for a compound corresponds in each case to one row of Table A;

Table 20 Compounds of the formula Ia in which $R^{3a}$ is Br, $R^{3b}$ is CN, and the combination of $R^1$, $R^2$ and $R^4$ for a compound corresponds in each case to one row of Table A;

Table 21 Compounds of the formula Ia in which $R^{3a}$ is $CF_3$, $R^{3b}$ is hydrogen, and the combination of $R^1$, $R^2$ and $R^4$ for a compound corresponds in each case to one row of Table A;

Table 22 Compounds of the formula Ia in which $R^{3a}$ is $CF_3$, $R^{3b}$ is $CH_3$, and the combination of $R^1$, $R^2$ and $R^4$ for a compound corresponds in each case to one row of Table A;

Table 23 Compounds of the formula Ia in which $R^{3a}$ is $CF_3$, $R^{3b}$ is Cl, and the combination of $R^1$, $R^2$ and $R^4$ for a compound corresponds in each case to one row of Table A;

Table 24 Compounds of the formula Ia in which $R^{3a}$ is $CF_3$, $R^{3b}$ is Br, and the combination of $R^1$, $R^2$ and $R^4$ for a compound corresponds in each case to one row of Table A;

Table 25 Compounds of the formula Ia in which $R^{3a}$ is $CF_3$, $R^{3b}$ is CN, and the combination of $R^1$, $R^2$ and $R^4$ for a compound corresponds in each case to one row of Table A;

Table 26 Compounds of the formula Ia in which $R^{3a}$ is hydrogen, $R^{3b}$ is $CF_3$, and the combination of $R^1$, $R^2$ and $R^4$ for a compound corresponds in each case to one row of Table A;

Table 27 Compounds of the formula Ia in which $R^{3a}$ is Cl, $R^{3b}$ is $CF_3$, and the combination of $R^1$, $R^2$ and $R^4$ for a compound corresponds in each case to one row of Table A;

Table 28 Compounds of the formula Ia in which $R^{3a}$ is Br, $R^{3b}$ is $CF_3$, and the combination of $R^1$, $R^2$ and $R^4$ for a compound corresponds in each case to one row of Table A;

Table 29 Compounds of the formula Ia in which $R^{3a}$ is $CH_3$, $R^{3b}$ is $CF_3$, and the combination of $R^1$, $R^2$ and $R^4$ for a compound corresponds in each case to one row of Table A;

Table 30 Compounds of the formula Ia in which $R^{3a}$ is $CF_3$, $R^{3b}$ is $CF_3$, and the combination of $R^1$, $R^2$ and $R^4$ for a compound corresponds in each case to one row of Table A.

Table 31 Compounds of the formula Ia in which $R^{3a}$ is $CH_3$, $R^{3b}$ is $NO_2$, and the combination of $R^1$, $R^2$ and $R^4$ for a compound corresponds in each case to one row of Table A.

Table 32 Compounds of the formula Ia in which $R^{3a}$ is $CH_3$, $R^{3b}$ is F, and the combination of $R^1$, $R^2$ and $R^4$ for a compound corresponds in each case to one row of Table A.

Table 33 Compounds of the formula Ia in which $R^{3a}$ is $CH_3$, $R^{3b}$ is I, and the combination of $R^1$, $R^2$ and $R^4$ for a compound corresponds in each case to one row of Table A.

Table 34 Compounds of the formula Ia in which $R^{3a}$ is $CH_3$, $R^{3b}$ is 5-chloro-2-thienyl, and the combination of $R^1$, $R^2$ and $R^4$ for a compound corresponds in each case to one row of Table A.

Table 35 Compounds of the formula Ia in which $R^{3a}$ is $CH_3$, $R^{3b}$ is 3-pyrazol-1H-yl, and the combination of $R^1$, $R^2$ and $R^4$ for a compound corresponds in each case to one row of Table A.

Table 36 Compounds of the formula Ia in which $R^{3a}$ is $CH_3$, $R^{3b}$ is 3-isoxazolyl, and the combination of $R^1$, $R^2$ and $R^4$ for a compound corresponds in each case to one row of Table A.

Table 37 Compounds of the formula Ia in which $R^{1a}$ is $OCH_3$, $R^{3b}$ is Cl, and the combination of $R^1$, $R^2$ and $R^4$ for a compound corresponds in each case to one row of Table A.

Table 38 Compounds of the formula Ia in which $R^{1a}$ is $OCH_3$, $R^{1b}$ is CN, and the combination of $R^1$, $R^2$ and $R^4$ for a compound corresponds in each case to one row of Table A.

Table 39 Compounds of the formula Ia in which $R^{3a}$ is cyclopropyl, $R^{3b}$ is Cl, and the combination of $R^1$, $R^2$ and $R^4$ for a compound corresponds in each case to one row of Table A.

Table 40 Compounds of the formula Ia in which $R^{3a}$ is ethyl, $R^{3b}$ is Cl, and the combination of $R^1$, $R^2$ and $R^4$ for a compound corresponds in each case to one row of Table A.

Table 41 Compounds of the formula Ia in which $R^{3a}$ is $OCHF_2$, $R^{3b}$ is CN, and the combination of $R^1$, $R^2$ and $R^4$ for a compound corresponds in each case to one row of Table A.

Table 42 Compounds of the formula Ia in which $R^{3a}$ is $CH_3$, $R^{3b}$ is C=NOH, and the combination of $R^1$, $R^2$ and $R^4$ for a compound corresponds in each case to one row of Table A.

Table 43 Compounds of the formula Ia in which $R^{3a}$ is $CH_3$, $R^{3b}$ is C=NOCH$_3$, and the combination of $R^1$, $R^2$ and $R^4$ for a compound corresponds in each case to one row of Table A.

Table 44 Compounds of the formula Ia in which $R^{3a}$ is $CH_3$, $R^{3b}$ is C=NNHCH$_2$CF$_3$, and the combination of $R^1$, $R^2$ and $R^4$ for a compound corresponds in each case to one row of Table A.

Table 45 Compounds of the formula Ia in which $R^{3a}$ is $CH_3$, $R^{3b}$ is C=NN(CH$_3$)$_2$, and the combination of $R^1$, $R^2$ and $R^4$ for a compound corresponds in each case to one row of Table A.

Table 46 Compounds of the formula Ia in which $R^{3a}$ is Cl, $R^{3b}$ is C=NOH, and the combination of $R^1$, $R^2$ and $R^4$ for a compound corresponds in each case to one row of Table A.

TABLE A

| No. | $R^1$ | $R^2$ | $R^4$ |
|---|---|---|---|
| A-1 | $CH_3$ | $CH_3$ | H |
| A-2 | $CH_3$ | $C_2H_5$ | H |
| A-3 | $CH_3$ | $CH_2CH_2CH_3$ | H |
| A-4 | $CH_3$ | $CH_2CH_2CH_2CH_3$ | H |
| A-5 | $CH_3$ | $CH_2CH_2CH_2CH_2CH_3$ | H |
| A-6 | $CH_3$ | $CH(CH_3)_2$ | H |
| A-7 | $CH_3$ | $CH(CH_3)C_2H_5$ | H |
| A-8 | $CH_3$ | $CH_2CH(CH_3)_2$ | H |
| A-9 | $CH_3$ | $C(CH_3)_3$ | H |
| A-10 | $CH_3$ | $CH_2C(CH_3)_3$ | H |
| A-11 | $CH_3$ | c-$C_3H_5$* | H |
| A-12 | $CH_3$ | c-$C_4H_7$* | H |
| A-13 | $CH_3$ | c-$C_5H_9$* | H |
| A-14 | $CH_3$ | c-$C_6H_{11}$* | H |
| A-15 | $CH_3$ | $CH_2$—c-$C_3H_5$* | H |
| A-16 | $CH_3$ | CH=$CH_2$ | H |
| A-17 | $CH_3$ | $CH_2$CH=$CH_2$ | H |
| A-18 | $CH_3$ | C≡CH | H |
| A-19 | $CH_3$ | $CH_2$C≡CH | H |
| A-20 | $CH_3$ | $CH_2CH_2OH$ | H |
| A-21 | $CH_3$ | $CH_2CH_2CH_2OH$ | H |
| A-22 | $CH_3$ | $CH_2OCH_3$ | H |
| A-23 | $CH_3$ | $CH_2CH_2OCH_3$ | H |
| A-24 | $CH_3$ | $CH_2CH_2CH_2OCH_3$ | H |
| A-25 | $CH_3$ | $CH_2SCH_3$ | H |
| A-26 | $CH_3$ | $CH_2CH_2SCH_3$ | H |
| A-27 | $CH_3$ | $CH_2CH_2CH_2SCH_3$ | H |
| A-28 | $CH_3$ | $CH_2S(O)CH_3$ | H |
| A-29 | $CH_3$ | $CH_2CH_2S(O)CH_3$ | H |
| A-30 | $CH_3$ | $CH_2CH_2CH_2S(O)CH_3$ | H |
| A-31 | $CH_3$ | $CH_2C(O)CH_3$ | H |
| A-32 | $CH_3$ | $CH_2C(O)CH_2CH_3$ | H |
| A-33 | $CH_3$ | $CH_2C(O)OCH_3$ | H |
| A-34 | $CH_3$ | $CH_2C(O)OCH_2CH_3$ | H |
| A-35 | $CH_3$ | $CHF_2$ | H |
| A-36 | $CH_3$ | $CH_2Cl$ | H |
| A-37 | $CH_3$ | $CH_2CH_2Cl$ | H |
| A-38 | $CH_3$ | $CH_2CH_2CN$ | H |
| A-39 | $CH_3$ | $C_6H_5$ | H |
| A-40 | $CH_3$ | 4-F-phenyl | H |
| A-41 | $C_2H_5$ | $C_2H_5$ | H |
| A-42 | $C_2H_5$ | $CH_2CH_2CH_3$ | H |
| A-43 | $C_2H_5$ | $CH_2CH_2CH_2CH_3$ | H |
| A-44 | $C_2H_5$ | $CH_2CH_2CH_2CH_2CH_3$ | H |
| A-45 | $C_2H_5$ | $CH(CH_3)_2$ | H |
| A-46 | $C_2H_5$ | $CH(CH_3)C_2H_5$ | H |
| A-47 | $C_2H_5$ | $CH_2CH(CH_3)_2$ | H |
| A-48 | $C_2H_5$ | $C(CH_3)_3$ | H |
| A-49 | $C_2H_5$ | $CH_2C(CH_3)_3$ | H |
| A-50 | $C_2H_5$ | c-$C_3H_5$* | H |
| A-51 | $C_2H_5$ | c-$C_4H_7$* | H |
| A-52 | $C_2H_5$ | c-$C_5H_9$* | H |
| A-53 | $C_2H_5$ | c-$C_6H_{11}$* | H |
| A-54 | $C_2H_5$ | $CH_2$—c-$C_3H_5$* | H |
| A-55 | $C_2H_5$ | CH=$CH_2$ | H |
| A-56 | $C_2H_5$ | $CH_2$CH=$CH_2$ | H |
| A-57 | $C_2H_5$ | C≡CH | H |
| A-58 | $C_2H_5$ | $CH_2$C≡CH | H |
| A-59 | $C_2H_5$ | $CH_2CH_2OH$ | H |
| A-60 | $C_2H_5$ | $CH_2CH_2CH_2OH$ | H |
| A-61 | $C_2H_5$ | $CH_2OCH_3$ | H |
| A-62 | $C_2H_5$ | $CH_2CH_2OCH_3$ | H |
| A-63 | $C_2H_5$ | $CH_2CH_2CH_2OCH_3$ | H |

TABLE A-continued

| No. | R¹ | R² | R⁴ |
|---|---|---|---|
| A-64 | $C_2H_5$ | $CH_2SCH_3$ | H |
| A-65 | $C_2H_5$ | $CH_2CH_2SCH_3$ | H |
| A-66 | $C_2H_5$ | $CH_2CH_2CH_2SCH_3$ | H |
| A-67 | $C_2H_5$ | $CH_2S(O)CH_3$ | H |
| A-68 | $C_2H_5$ | $CH_2CH_2S(O)CH_3$ | H |
| A-69 | $C_2H_5$ | $CH_2CH_2CH_2S(O)CH_3$ | H |
| A-70 | $C_2H_5$ | $CH_2C(O)CH_3$ | H |
| A-71 | $C_2H_5$ | $CH_2C(O)CH_2CH_3$ | H |
| A-72 | $C_2H_5$ | $CH_2C(O)OCH_3$ | H |
| A-73 | $C_2H_5$ | $CH_2C(O)OCH_2CH_3$ | H |
| A-74 | $C_2H_5$ | $CHF_2$ | H |
| A-75 | $C_2H_5$ | $CH_2Cl$ | H |
| A-76 | $C_2H_5$ | $CH_2CH_2Cl$ | H |
| A-77 | $C_2H_5$ | $CH_2CH_2CN$ | H |
| A-78 | $C_2H_5$ | $C_6H_5$ | H |
| A-79 | $C_2H_5$ | 4-F-phenyl | H |
| A-80 | $CH_2CH_2CH_3$ | $CH_2CH_2CH_3$ | H |
| A-81 | $CH_2CH_2CH_3$ | $CH_2CH_2CH_2CH_3$ | H |
| A-82 | $CH_2CH_2CH_3$ | $CH_2CH_2CH_2CH_2CH_3$ | H |
| A-83 | $CH_2CH_2CH_3$ | $CH(CH_3)_2$ | H |
| A-84 | $CH_2CH_2CH_3$ | $CH(CH_3)C_2H_5$ | H |
| A-85 | $CH_2CH_2CH_3$ | $CH_2CH(CH_3)_2$ | H |
| A-86 | $CH_2CH_2CH_3$ | $C(CH_3)_3$ | H |
| A-87 | $CH_2CH_2CH_3$ | $CH_2C(CH_3)_3$ | H |
| A-88 | $CH_2CH_2CH_3$ | $c\text{-}C_3H_5$* | H |
| A-89 | $CH_2CH_2CH_3$ | $c\text{-}C_4H_7$* | H |
| A-90 | $CH_2CH_2CH_3$ | $c\text{-}C_5H_9$* | H |
| A-91 | $CH_2CH_2CH_3$ | $c\text{-}C_6H_{11}$* | H |
| A-92 | $CH_2CH_2CH_3$ | $CH_2\text{-}c\text{-}C_3H_5$* | H |
| A-93 | $CH_2CH_2CH_3$ | $CH=CH_2$ | H |
| A-94 | $CH_2CH_2CH_3$ | $CH_2CH=CH_2$ | H |
| A-95 | $CH_2CH_2CH_3$ | $C\equiv CH$ | H |
| A-96 | $CH_2CH_2CH_3$ | $CH_2C\equiv CH$ | H |
| A-97 | $CH_2CH_2CH_3$ | $CH_2CH_2OH$ | H |
| A-98 | $CH_2CH_2CH_3$ | $CH_2CH_2CH_2OH$ | H |
| A-99 | $CH_2CH_2CH_3$ | $CH_2OCH_3$ | H |
| A-100 | $CH_2CH_2CH_3$ | $CH_2CH_2OCH_3$ | H |
| A-101 | $CH_2CH_2CH_3$ | $CH_2CH_2CH_2OCH_3$ | H |
| A-102 | $CH_2CH_2CH_3$ | $CH_2SCH_3$ | H |
| A-103 | $CH_2CH_2CH_3$ | $CH_2CH_2SCH_3$ | H |
| A-104 | $CH_2CH_2CH_3$ | $CH_2CH_2CH_2SCH_3$ | H |
| A-105 | $CH_2CH_2CH_3$ | $CH_2S(O)CH_3$ | H |
| A-106 | $CH_2CH_2CH_3$ | $CH_2CH_2S(O)CH_3$ | H |
| A-107 | $CH_2CH_2CH_3$ | $CH_2CH_2CH_2S(O)CH_3$ | H |
| A-108 | $CH_2CH_2CH_3$ | $CH_2C(O)CH_3$ | H |
| A-109 | $CH_2CH_2CH_3$ | $CH_2C(O)CH_2CH_3$ | H |
| A-110 | $CH_2CH_2CH_3$ | $CH_2C(O)OCH_3$ | H |
| A-111 | $CH_2CH_2CH_3$ | $CH_2C(O)OCH_2CH_3$ | H |
| A-112 | $CH_2CH_2CH_3$ | $CHF_2$ | H |
| A-113 | $CH_2CH_2CH_3$ | $CH_2Cl$ | H |
| A-114 | $CH_2CH_2CH_3$ | $CH_2CH_2Cl$ | H |
| A-115 | $CH_2CH_2CH_3$ | $CH_2CH_2CN$ | H |
| A-116 | $CH_2CH_2CH_3$ | $C_6H_5$ | H |
| A-117 | $CH_2CH_2CH_3$ | 4-F-phenyl | H |
| A-118 | $CH(CH_3)_2$ | $CH_2CH_2CH_2CH_3$ | H |
| A-119 | $CH(CH_3)_2$ | $CH_2CH_2CH_2CH_2CH_3$ | H |
| A-120 | $CH(CH_3)_2$ | $CH(CH_3)_2$ | H |
| A-121 | $CH(CH_3)_2$ | $CH(CH_3)C_2H_5$ | H |
| A-122 | $CH(CH_3)_2$ | $CH_2CH(CH_3)_2$ | H |
| A-123 | $CH(CH_3)_2$ | $C(CH_3)_3$ | H |
| A-124 | $CH(CH_3)_2$ | $CH_2C(CH_3)_3$ | H |
| A-125 | $CH(CH_3)_2$ | $c\text{-}C_3H_5$* | H |
| A-126 | $CH(CH_3)_2$ | $c\text{-}C_4H_7$* | H |
| A-127 | $CH(CH_3)_2$ | $c\text{-}C_5H_9$* | H |
| A-128 | $CH(CH_3)_2$ | $c\text{-}C_6H_{11}$* | H |
| A-129 | $CH(CH_3)_2$ | $CH_2\text{-}c\text{-}C_3H_5$* | H |
| A-130 | $CH(CH_3)_2$ | $CH=CH_2$ | H |
| A-131 | $CH(CH_3)_2$ | $CH_2CH=CH_2$ | H |
| A-132 | $CH(CH_3)_2$ | $C\equiv CH$ | H |
| A-133 | $CH(CH_3)_2$ | $CH_2C\equiv CH$ | H |
| A-134 | $CH(CH_3)_2$ | $CH_2CH_2OH$ | H |
| A-135 | $CH(CH_3)_2$ | $CH_2CH_2CH_2OH$ | H |
| A-136 | $CH(CH_3)_2$ | $CH_2OCH_3$ | H |
| A-137 | $CH(CH_3)_2$ | $CH_2CH_2OCH_3$ | H |
| A-138 | $CH(CH_3)_2$ | $CH_2CH_2CH_2OCH_3$ | H |
| A-139 | $CH(CH_3)_2$ | $CH_2SCH_3$ | H |
| A-140 | $CH(CH_3)_2$ | $CH_2CH_2SCH_3$ | H |
| A-141 | $CH(CH_3)_2$ | $CH_2CH_2CH_2SCH_3$ | H |
| A-142 | $CH(CH_3)_2$ | $CH_2S(O)CH_3$ | H |
| A-143 | $CH(CH_3)_2$ | $CH_2CH_2S(O)CH_3$ | H |
| A-144 | $CH(CH_3)_2$ | $CH_2CH_2CH_2S(O)CH_3$ | H |
| A-145 | $CH(CH_3)_2$ | $CH_2C(O)CH_3$ | H |
| A-146 | $CH(CH_3)_2$ | $CH_2C(O)CH_2CH_3$ | H |
| A-147 | $CH(CH_3)_2$ | $CH_2C(O)OCH_3$ | H |
| A-148 | $CH(CH_3)_2$ | $CH_2C(O)OCH_2CH_3$ | H |
| A-149 | $CH(CH_3)_2$ | $CHF_2$ | H |
| A-150 | $CH(CH_3)_2$ | $CH_2Cl$ | H |
| A-151 | $CH(CH_3)_2$ | $CH_2CH_2Cl$ | H |
| A-152 | $CH(CH_3)_2$ | $CH_2CH_2CN$ | H |
| A-153 | $CH(CH_3)_2$ | $C_6H_5$ | H |
| A-154 | $CH(CH_3)_2$ | 4-F-phenyl | H |
| A-155 | —$CH_2$—$CH_2$— | | H |
| A-156 | —$CH_2$—$CH_2$—$CH_2$— | | H |
| A-157 | —$CH_2$—$CH_2$—$CH_2$—$CH_2$— | | H |
| A-158 | —$CH_2$—$CH_2$—$CH_2$—$CH_2$—$CH_2$— | | H |
| A-159 | —$CH=CH$—$CH=CH$— | | H |
| A-160 | —$CH_2$—S—$CH_2$—$CH_2$— | | H |
| A-161 | —$CH(CH_3)$—S—$CH_2$—$CH_2$— | | H |
| A-162 | —$CH_2$—S—$CH_2$—$CH_2$—$CH_2$— | | H |
| A-163 | —$CH(CH_3)$—S—$CH_2$—$CH_2$—$CH_2$— | | H |
| A-164 | —$CH_2$—$CH_2$—S—$CH_2$—$CH_2$— | | H |
| A-165 | —$CH_2$—$CH_2$—O—$CH_2$—$CH_2$— | | H |
| A-166 | —$CH_2$—$CH_2$—C(O)—$CH_2$—$CH_2$— | | H |
| A-167 | —$CH_2$—$CH_2$—CH(OH)—$CH_2$—$CH_2$— | | H |
| A-168 | —$CH_2$—S(O)—$CH_2$—$CH_2$— | | H |
| A-169 | —$CH_2$—S(O)—$CH_2$—$CH_2$—$CH_2$— | | H |
| A-170 | —$CH_2$—$CH_2$—S(O)—$CH_2$—$CH_2$— | | H |
| A-171 | $CH_3$ | $CH_2CH_2\text{-}c\text{-}C_3H_5$* | H |
| A-172 | $CH_3$ | $CH(CH_3)\text{-}c\text{-}C_3H_5$* | H |
| A-173 | $CH_3$ | $CH_2\text{-}c\text{-}C_4H_7$* | H |
| A-174 | $CH_3$ | $CH_2\text{-}c\text{-}C_5H_9$* | H |
| A-175 | $CH_3$ | $CH(CH_3)CH(CH_3)_2$ | H |
| A-176 | $CH_3$ | $(CH_2)_5CH_3$ | H |
| A-177 | $CH_3$ | 2-EtHex** | H |
| A-178 | $C_2H_5$ | $CH_2CH_2\text{-}c\text{-}C_3H_5$* | H |
| A-179 | $C_2H_5$ | $CH(CH_3)\text{-}c\text{-}C_3H_5$* | H |
| A-180 | $C_2H_5$ | $CH_2\text{-}c\text{-}C_4H_7$* | H |
| A-181 | $C_2H_5$ | $CH_2\text{-}c\text{-}C_5H_9$* | H |
| A-182 | $C_2H_5$ | $CH(CH_3)CH(CH_3)_2$ | H |
| A-183 | $C_2H_5$ | $(CH_2)_5CH_3$ | H |
| A-184 | $C_2H_5$ | 2-EtHex** | H |
| A-185 | $(CH_2)_2CH_3$ | $CH_2CH_2\text{-}c\text{-}C_3H_5$* | H |
| A-186 | $(CH_2)_2CH_3$ | $CH(CH_3)\text{-}c\text{-}C_3H_5$* | H |
| A-187 | $(CH_2)_2CH_3$ | $CH_2\text{-}c\text{-}C_4H_7$* | H |
| A-188 | $(CH_2)_2CH_3$ | $CH_2\text{-}c\text{-}C_5H_9$* | H |
| A-189 | $(CH_2)_2CH_3$ | $CH(CH_3)CH(CH_3)_2$ | H |
| A-190 | $(CH_2)_2CH_3$ | $(CH_2)_5CH_3$ | H |
| A-191 | $(CH_2)_2CH_3$ | 2-EtHex** | H |
| A-192 | $CH(CH_3)_2$ | $CH_2CH_2\text{-}c\text{-}C_3H_5$* | H |
| A-193 | $CH(CH_3)_2$ | $CH(CH_3)\text{-}c\text{-}C_3H_5$* | H |
| A-194 | $CH(CH_3)_2$ | $CH_2\text{-}c\text{-}C_4H_7$* | H |
| A-195 | $CH(CH_3)_2$ | $CH_2\text{-}c\text{-}C_5H_9$* | H |
| A-196 | $CH(CH_3)_2$ | $CH(CH_3)CH(CH_3)_2$ | H |
| A-197 | $CH(CH_3)_2$ | $(CH_2)_4CH_3$ | H |
| A-198 | $CH(CH_3)_2$ | $(CH_2)_5CH_3$ | H |
| A-199 | $(CH_2)_2CH_3$ | 2-EtHex** | H |
| A-200 | $CH_2CH_2OH$ | $(CH_2)_4CH_3$ | H |
| A-201 | $CH_2\text{-}c\text{-}C_3H_5$* | $CH_2\text{-}c\text{-}C_3H_5$* | H |
| A-202 | $CH_2CH_2\text{-}c\text{-}C_3H_5$* | $CH_2CH_2\text{-}c\text{-}C_3H_5$* | H |
| A-203 | $CH(CH_3)\text{-}c\text{-}C_3H_5$* | $CH(CH_3)\text{-}c\text{-}C_3H_5$* | H |
| A-204 | $CH_2\text{-}c\text{-}C_4H_7$* | $CH_2\text{-}c\text{-}C_4H_7$* | H |
| A-205 | $CH_2\text{-}c\text{-}C_5H_9$* | $CH_2\text{-}c\text{-}C_5H_9$* | H |
| A-206 | $CH(CH_3)CH(CH_3)_2$ | $CH(CH_3)CH(CH_3)_2$ | H |
| A-207 | $(CH_2)_5CH_3$ | $(CH_2)_5CH_3$ | H |
| A-208 | 2-EtHex** | 2-EtHex** | H |
| A-209 | $(CH_2)_3CH_3$ | $(CH_2)_3CH_3$ | H |
| A-210 | $CH(CH_3)CH_2CH_3$ | $CH(CH_3)CH_2CH_3$ | H |

*c-$C_nH_{2n-1}$: n membered cycloalkyl
**2-EtHex: $CH_2CH(C_2H_5)(CH_2)_3CH_3$

According to a further aspect, the invention relates to a process for preparing a compound of the formula I. This process is hereinafter termed "process A". According to a first embodiment, process A comprises reacting a compound of the formula II with a compound of formula III. According to a second embodiment, process A comprises reacting a compound of the formula II with a compound of formula IV.

In formula II, p, $R^3$ and $R^4$ are as defined above and in the claims. In particular, p, $R^3$ and $R^4$ have the meanings which are given above as preferred or particular meanings.

Particular preference is given to compounds of the formula II, wherein p is 0, 1 or 2. Preference is given to compounds II, where p=1 and where the one radical $R^3$ is located in ortho- or para position with regard to the group $NR^4$. Preference is also given to compounds II, where p=2 and where, one radical $R^3$ is located in ortho position while the other radical $R^3$ is located in para position with regard to the group $NR^4$. Particular preferred compounds of the formula II are represented by the following formula IIa

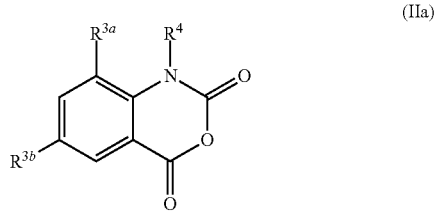

(IIa)

where $R^4$ are as defined herein and where $R^{3a}$ is hydrogen or has one of the meanings given herein for $R^3$ and $R^{3b}$ is hydrogen or has one of the meanings given herein for $R^3$.

In formula IIa the radical $R^{3a}$ and $R^{3b}$ are, independently of each other, preferably selected from the group consisting of hydrogen, halogen, $C_1$-$C_4$-alkyl, $C_1$-$C_4$-haloalkyl and cyano, it being possible that $R^{3a}$ and $R^{3b}$ are identical or different. In formula IIa the radical $R^{3a}$ is in particular selected from the group consisting of hydrogen, halogen, in particular chlorine or bromine, methyl, and halomethyl, e.g. trifluoromethyl, difluoromethyl or bromodifluoromethyl. In formula IIa the radical $R^{3b}$ is in particular selected from the group consisting of hydrogen, halogen, in particular chlorine or bromine, cyano, methyl, and halomethyl, e.g. trifluoromethyl, difluoromethyl or bromodifluoromethyl.

In formula IIa, $R^4$ is in particular hydrogen.

Particular examples of compounds of the formula II are the compounds of formula IIa, wherein $R^4$ is hydrogen and where $R^{3a}$ and $R^{3b}$ are as defined in tables 1 to 46 above.

In the process A of the present invention, preference is given to compounds of the formulae III and IV, where the variable t is 0 and where $R^1$ and $R^2$, independently of each other, are selected from the group consisting of $C_1$-$C_6$-alkyl, $C_1$-$C_8$-haloalkyl, $C_3$-$C_8$-cycloalkyl, $C_3$-$C_8$-halocycloalkyl, $C_2$-$C_8$-alkenyl, $C_2$-$C_8$-haloalkenyl, wherein alkyl, alkenyl and cycloalkyl may optionally be substituted by one or more, e.g. 1 or 2 radicals $R^a$, where $R^a$ is as defined above and in particular has one of the preferred meanings given above for $R^a$. Particular preference is given to compounds of the formulae III and IV, where the variable t is 0 and where $R^1$ and $R^2$, independently of each other, are more preferably selected from the group consisting of $C_1$-$C_6$-alkyl, $C_3$-$C_7$-cycloalkyl and $C_3$-$C_8$-cycloalkyl-$C_1$-$C_4$-alkyl.

Likewise, preference is given to compounds of the formulae III and IV, where the variable t is 0 and where $R^1$ and $R^2$ together represent a $C_3$-$C_7$-alkylene or $C_3$-$C_7$-alkenylene group forming together with the sulfur atom to which they are attached a 4-, 5-, 6-, 7- or 8-membered, in particular a 5-, 6 or 7-membered, saturated or partially unsaturated ring, wherein 1 or 2 of the $CH_2$ groups in the $C_3$-$C_7$-alkylene chain or 1 or 2 of any of the $CH_2$ or CH groups in the $C_3$-$C_7$-alkenylene chain may be replaced may be replaced by 1 or 2 groups independently selected from the group consisting of O, S and $NR^y$, and wherein the carbon atoms in the $C_3$-$C_7$-alkylene or $C_3$-$C_7$-alkenylene chain may be substituted with 1 to 5 identical or different substituents $R^x$, i.e. each of the carbon atoms may be unsubstituted or may carry 1 or 2 substituents $R^x$ with a maximum of 5 substituents $R^x$, in particular with a maximum of 2 substituents $R^x$ per alkylene or alkenylene chain. In this context $R^x$ and $R^y$ are as defined above and in particular have one of the preferred meanings given above for $R^x$ and $R^y$, respectively. Particular preference is also given to compounds of the formulae III and IV, where the variable t is 0 and where $R^1$ and $R^2$ together preferably represent a $C_4$-$C_7$-alkylene group forming together with the sulfur atom to which they are attached a 5-, 6-, 7- or 8-membered, in particular a 5-, 6 or 7-membered, saturated ring.

In the compounds of formula IV, $A^-$ is an equivalent of an anion having a $pK_B$ of at least 10, as determined under standard conditions (298 K; 1.013 bar) in water. In this context "equivalent means" the amount of anion required to achieve electroneutrality. For example, if the anion carries one negative charge the equivalent is 1, while if the anione carries two negative charges the equivalent is ½. Suitable anions are those, which have a basicity constant $pK_B$ of at least 10, in particular at least 12 as determined under standard conditions (298 K; 1.013 bar) in water. Suitable anions include inorganic ions such as $SO_4^{2-}$, $HSO_4^-$, $Cl^-$, $ClO_4^-$, $BF_4^-$, $PF_6^-$, $HPO_4^-$, and organic anions such as methylsulfonate, trifluoromethylsulfonate, trifluoroacetate, phenylsulfonate, toluenesulfonate, mesitylene sulfonate and the like.

Examples of compounds III are those, wherein the variable t is 0 and where $R^1$ and $R^2$ are defined in rows A.1 to A.210 of table A. Further examples of compounds III are those, wherein the variable t is 1 and where $R^1$ and $R^2$ are defined in rows A.1 to A.210 of table A. Examples of compounds IV are those, wherein the variable t is 0, $A^-$ is ½$SO_4^{2-}$ or $HSO_4^-$, and where $R^1$ and $R^2$ are defined in rows A.1 to A.210 of table A. Further examples of compounds III and IV are those, wherein the variable t is 1, $A^-$ is ½$SO_4^{2-}$ or $HSO_4^-$, and where $R^1$ and $R^2$ are defined in rows A.1 to A.210 of table A.

In process A, the compounds of formulae III or IV, respectively, are typically employed in an amount of from 0.9 to 2 mol, preferably from 0.9 to 1.5 mol, more preferably from 0.9 to 1.2 mol and in particular from 0.95 to 1.1 mol per mol of the compound of formula II used in process A.

It has been found advantageous to carry out the reaction of process A in the presence of a base. Suitable bases include bases which are soluble or insoluble in the reaction medium. The base may be used in catalytic or stoichiometric amounts. The amount of base may preferably be in the range from 0.1 to 2 mol, in particular from 0.9 to 1.5 mol per mol of compound II or in the range from 0.1 to 2 mol, in particular from 0.9 to 1.5 mol per mol of compound III or IV. In a particular embodiment the base is used in an amount of at least 0.9 mol, in particular at least 1 mol, e.g. from 0.9 to 2 mol, in particular from 1 to 1.5 mol per mol of compound II, in particular, if a compound of formula IV is used.

Suitable bases include but are not limited to oxo bases and amine bases. Suitable oxo bases include but are not limited to hydroxides, in particular alkalimetal hydroxides such as lithium, sodium or potassium hydroxide, carbonates, in particular alkalimetal carbonates, such as lithium, sodium or potassium carbonates, hydrogen carbonates, in particular alkalimetal hydrogen carbonates, such as lithium, sodium or potassium hydrogen carbonates, phosphates or hydrogenphosphates, in particular alkalimetal phosphates or hydrogenphosphates, such as lithium, sodium or potassium phosphate, or lithium, sodium or potassium hydrogen phosphate, alkoxides, in particular alkalimetal alkoxides such as sodium or potassium methoxide, sodium or potassium ethoxide or sodium or potassium tert-butanolate, carboxylates, in particular alkalimetal carboxylates, such as lithium, sodium or potassium formiate, lithium, sodium or potassium acetate or lithium, sodium or potassium propionate. Suitable amine bases include but are not limited to organic amines, preferably secondary and more preferably tertiary amines, in particular aliphatic or cycloaliphatic amines, e.g. di-$C_1$-$C_4$-alkylamines, tri-$C_1$-$C_4$-alkylamines, $C_3$-$C_6$-cycloalkylamines, $C_3$-$C_6$-cycloalkyl-di-$C_1$-$C_4$-alkylamines or cyclic amines such as dimethylamine, diethylamine, diisopropylamine, cyclohexylamine, dimethylcyclohexylamine, trimethylamine, diethylamine or triethylamine, piperidine and N-methylpiperidine. Preferred bases are oxo bases, in particular alkalimetal alkoxides, which are also termed alkalimetal alkanolates, especially sodium and potassium alkanolates such as sodium methoxides, potassium methoxide, sodium ethoxide, potassium ethoxide, sodium tert-butanolate or potassium tert-butanolate. Mixtures of oxo bases and amine bases may also be used. Likewise preferred are bases which are selected from the aforementioned amine bases, in particular from the aforementioned tertiary amines, especially tri-$C_1$-$C_4$-alkylamines, $C_3$-$C_6$-cycloalkyl-di-$C_1$-$C_4$-alkylamines and N—$C_1$-$C_4$-alkyl-substituted cyclic amines such as dimethylcyclohexylamine, trimethylamine, diisopropylethylamine or triethylamine, piperidine and N-methylpiperidine.

In particular embodiments of the invention, the reaction of process A is carried out in an organic solvent or a mixture of organic solvents. Suitable solvents for carrying out reaction A may be protic or aprotic solvents and mixtures thereof, with aprotic solvents being preferred. Examples of aprotic solvents are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride, chloroform or 1,2-dichlorethane, aromatic hydrocarbons, such as benzene, toluene, the xylenes or chlorobenzene, open-chained ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, esters, such as ethyl acetate or ethyl propionate, aliphatic or alicyclic carbonates such as diethyl carbonate, ethylene carbonate (1,3-dioxolan-2-on) or propylene carbonate (4-methyl-1,2-dioxolan-2-on). Suitable aprotic solvents may also be pyridines such as pyridine, 2,6-dimethylpyridine or 2,4,6-trimethylpyridine, N,N-di-$C_1$-$C_4$-alkylamides of aliphatic carboxylic acids such as N,N-dimethyl formamide, N,N-dimethyl acetamide, N—$C_1$-$C_4$-alkyl lactames such as N-methyl pyrrolidinone and aliphatic or alicyclic sulfones and sulfoxides such as sulfolane and dimethylsulfoxide (DMSO). Examples for polar protic solvents are $C_1$-$C_4$-alkanols such as methanol, ethanol, propanol and isopropanol, $C_2$-$C_4$-alkandiols, such as ethylene glycol or propylene glycol, and ether alkanols such as diethylene glycol, and mixtures thereof. Preferably the reaction is carried out in an aprotic solvent or a mixture of aprotic solvents.

In a particular embodiment, the reaction of process A is carried out in a polar aprotic solvent containing or essentially comprising dimethylsulfoxide (DMSO). The use of DMSO or an aprotic solvent containing or essentially comprising DMSO results in high yield and high purity of the compound of formula I. If the aprotic solvent used in process A contains DMSO the amount of DMSO will generally be at least 20% by weight, in particular at least 50% by weight, based on the total amount of aprotic organic solvent used in process A. If the aprotic solvent used in process A essentially comprises DMSO the amount of DMSO will generally be at least 90% by weight, in particular at least 95% by weight, based on the total amount of aprotic organic solvent used in process A. In this particular embodiment DMSO is especially the sole solvent.

In another particular embodiment, the reaction of process A is carried out in a polar aprotic solvent containing or essentially comprising an aliphatic or alicyclic carbonate with particular preference given to propylene carbonate. The use of an aliphatic or alicyclic carbonate or an aprotic solvent containing or essentially comprising aliphatic or alicyclic carbonate, especially propylene carbonate, results in good yield and purity of the compound of formula I and allows to use the reaction mixture containing the compound of formula I in the preparation or the compound of formula V according to the process B without further purification or isolation of I. If the aprotic solvent used in process A contains an aliphatic or alicyclic carbonate, especially propylene carbonate, the amount of the aliphatic or alicyclic carbonate will generally be at least 20% by weight, in particular at least 50% by weight, based on the total amount of aprotic organic solvent used in process A. If the aprotic solvent used in process A essentially comprises an aliphatic or alicyclic carbonate, especially propylene carbonate, the amount of the aliphatic or alicyclic carbonate will generally be at least 90% by weight, in particular at least 95% by weight, based on the total amount of aprotic organic solvent used in process A. In this particular embodiment the aliphatic or alicyclic carbonate, especially propylene carbonate, is preferably the sole solvent.

The reaction according to process A is generally performed at a temperature in the range of from −40 to +150° C., preferably from 0 to 110° C. and more preferably from 0 to 80° C. In principle the reaction temperature can be as high as the boiling point of the reaction mixture at the given reaction pressure, but is preferably kept at the indicated lower values. The reaction pressure is generally not critical and may range from 0.9 to 2 bar, in particular from 0.9 to 1.5 bar and especially from 0.9 to 1.1 bar.

The reaction of process A is carried out by reacting compound II with a suitable amount of a compound of formulae III or IV under the above reaction conditions. The reaction can be performed for example in the following manner: a solution or a suspension of a compound of formula II in a suitable organic solvent is added to a suitable reaction vessel. To this mixture, the compound of formulae III or IV is added, preferably as a solution or suspension in an organic solvent. Addition of compound III or IV may be done as a single portion or preferably continuously or in several portions. To the resulting mixture, the base may be added, if desired. The base may be added either neat, in solution or as a suspension in a suitable organic solvent. Addition of the base may be done as a single portion or preferably continuously or in several portions. It is also possible to add the compound and, if desired, the base at the same time.

The compound of formula I formed in reaction of process A can be isolated from the reaction mixture by customary methods, e.g. by the addition of water and subsequent extraction with a suitable solvent, followed by concentration by distilling off the solvent. Suitable solvents for extraction purposes are essentially immiscible with water and capable of dissolving the compound of formula I. Examples are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride or chloroform, aromatic hydrocarbons, such as benzene, toluene, the xylenes or chlorobenzene, open-chained ethers, such as diethylether, methyl-tert-butyl ether or methyl-isobutyl ether, or esters, such as ethyl acetate or ethyl propionate.

The isolated product can be further purified, e.g. by crystallization or by chromatography or combined measures. However, frequently, the product is already obtained in a purity which does not require further purification steps.

The compounds of formulae III and IV are known from prior art, e.g. from WO 2007/006670; WO 2008/141843; Y. Tamura et al, Tetrahedron, 1975, 31, 3035-3040; Fujii et al., Heteroatom Chemistry (2004), 15(3), 246-250; Johnson et al., J. Org. Chem., 1989, (54), 986-988; Yoshimura et al., J. Org. Chem., 1976, (41), 1728-1733; Appel et al., Chem. Ber., 1962 (95), 849-854 and Chem. Ber., 1966 (99), 3108-3117 or from Young et al, J. Org. Chem., 1987, (52), 2695-2699 or they can be prepared by analogy to the methods described therein or by analogy to the methods described in WO 2008/141843, U.S. Pat. No. 6,136,983 and the literature cited therein.

A particular suitable method for preparing the compounds of formulae IV is described scheme 1 below.

Scheme 1:

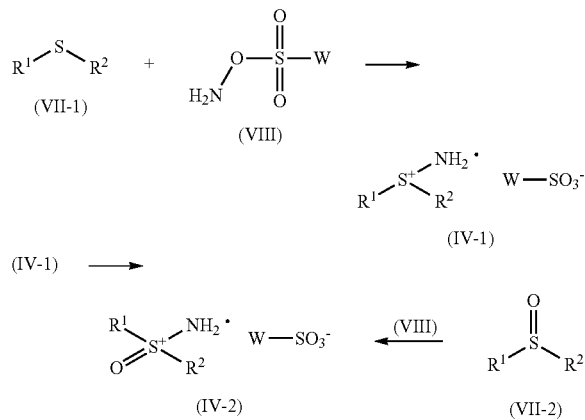

In scheme 1, $R^1$ and $R^2$ are as defined above. W can be any group which does not disturb the reaction, such as OH, $NH_2$, $C_1$-$C_4$-alkyl, $C_1$-$C_4$-haloalkyl, aryl or hetaryl, where the last two radicals are unsubstituted or substituted by 1, 2 or 3 radicals $R^e$, which are preferably selected from halogen and $C_1$-$C_4$-alkyl. W is preferably OH or preferably an aromatic group such as phenyl, optionally substituted with one or more radicals selected from halogen and $C_1$-$C_4$-alkyl, for example phenyl, 4-methylphenyl or 2,4,6-trimethylphenyl. In a particular embodiment W is OH.

According to the first reaction depicted in scheme 1, a sulfonyl hydroxylamine of formula (VIII) is reacted with a sulfide of formula (VII-1), yielding a compound of formula IV-1 which corresponds to a compound of formula IV, where t=0. The reaction can be performed by contacting the compounds of formula VII and VIII.

The compound of formula VIII is preferably employed in an amount of from 0.7 to 1.1 mol, preferably from 0.8 to 1.0 mol and in particular from 0.85 to 0.99 mol per mol of the compound of formula VII-1.

It has been found advantageous to carry out the first reaction of scheme 1 in the presence of a base. The base may be used in catalytic or stoichiometric amounts. The amount of base may preferably be in the range from 0.9 to 2 mol, in particular from 0.9 to 1.5 mol per mol of compound II or in the range from 1.0 to 1.2 mol per mol of compound VIII.

Suitable bases include in particular oxo bases. Suitable oxo bases include but are not limited to those mentioned in context with the reaction of process A. Preferred bases alkalimetal alkoxides, especially sodium and potassium alkanolates such as sodium methoxide, potassium methoxide, sodium ethoxide, potassium ethoxide, sodium tert-butanolate or potassium tert-butanolate.

In particular embodiments of the invention, the first reaction depicted in scheme 1 is carried out in an organic solvent or a mixture of organic solvents. Suitable solvents include but are not limited to polar protic or aprotic solvents and mixtures thereof, with protic solvents being preferred. Examples of polar aprotic solvents are halogenated alkanes, such as methylene chloride, chloroform or 1,2-dichlorethane, halogenated aromatic hydrocarbons, such as chlorobenzene, open-chained ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, or esters, such as ethyl acetate or ethyl propionate, N,N-di-$C_1$-$C_4$-alkylamides of aliphatic carboxylic acids such as N,N-dimethyl formamide, N,N-dimethyl acetamide, and N—$C_1$-$C_4$-alkyl lactames such as N-methyl pyrrolidinone. Examples for polar protic solvents are $C_1$-$C_4$-alkanols such as methanol, ethanol, propanol and isopropanol, $C_2$-$C_4$-alkandiols, such as ethylene glycol or propylene glycol, and ether alkanols such as diethylene glycol, and mixtures thereof. Preferably the reaction is carried out in a protic solvent or a mixture thereof with an aprotic solvent. In particular, the solvent is a $C_1$-$C_4$-alkanol or a mixture of $C_1$-$C_4$-alkanols.

The reaction according to the first reaction depicted in scheme 1 is generally performed at a temperature in the range of from −50 to +20° C., preferably from −40 to 10° C. and more preferably from −40 to +5° C. The reaction pressure is generally not critical and may range from 0.9 to 2 bar, in particular from 0.9 to 1.5 bar and especially from 0.9 to 1.1 bar.

The first reaction of scheme 1 is carried out by reacting compound VII-1 with a suitable amount of a compound of formulae VIII under the above reaction conditions. The reaction can be performed for example in the following manner: a solution or a suspension of a compound of formula VII-1, optionally containing a base, in a suitable organic solvent is charged to a suitable reaction vessel. To this mixture the compound VIII, preferably as a solution or suspension in an organic solvent is added at the above temperatures. Addition of compound VIII may be done as a single portion or preferably continuously or in several portions.

The compound of formula IV-1 formed in this reaction can be isolated from the reaction mixture by customary methods, e.g. by crystallization or precipitation from the reaction mixture, preferably after having removed insoluble by products. Precipitation or crystallization may be achieved by concentration of the reaction mixture, cooling the reaction mixture or addition of an "anti-solvent" to the reaction mixture. Anti-solvents are organic solvents, wherein the compound IV-1 is insoluble or only sparingly soluble. Suitable anti-solvents include but are not limited to aliphatic hydrocarbons, such as alkanes, e.g. pentane, hexane or heptane, cycloaliphatic hydrocarbons, such as cycloalkanes, e.g. cyclopentane or cyclohexane, aromatic hydrocarbons, such as benzene, toluene, the xylenes or chlorobenzene and open-chained ethers, such as diethylether, methyl-tert-butyl ether or methyl-isobutyl ether.

The isolated product can be further purified, e.g. by crystallization or tituration with a solvent, e.g. with acetonitrile.

However, frequently, the product is already obtained in a purity which does not require further purification steps.

Compounds of formula IV, in which t is 1 (compounds IV-2), may be prepared from compounds of formula (IV-1) by oxidation with an appropriate oxidant, in analogy to described methods as described by, for example, Dillard et al, Journal of Medicinal Chemistry (1980), 23, 717-722. The compounds of formula (IV-2) may also be prepared by reacting a sulfoxide VII-2 with an amination agent, such as a compound VIII, in particular aminoxysulfonic acid $NH_2OSO_3H$, under similar conditions as described for the reaction of VII-1 with VIII.

The compounds of formula II are known from prior art, e.g. from WO 2003/016284 and Coppola, Synthesis 1980, pp. 505-536 or they can be prepared by analogy to the methods described therein. The compounds II can also be prepared by reacting an anthranilic acid derivative IX with carbonic ester or an equivalent thereof such as phosgene, diphosgene (trichloromethyl chloroformate), triphosgene (bis(trichloromethyl)carbonate), dialkyl carbonates, carbonyl diimidazole or alkyl chloroformiates as depicted in scheme 2.

Scheme 2:

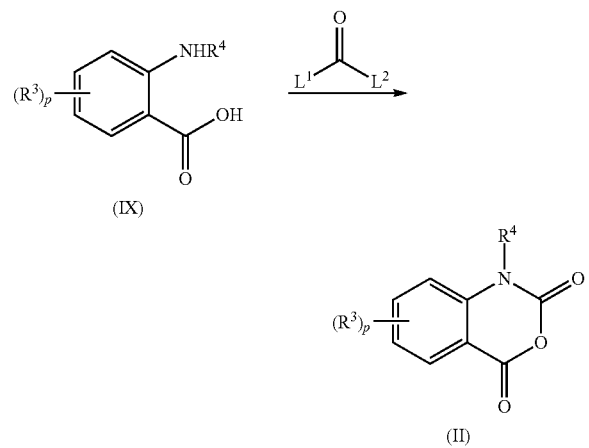

In scheme 2, p, $R^3$ and $R^4$ are as defined above. $L^1$ is halogen, in particular chlorine, imidazole, $C_1$-$C_4$-alkoxy, in particular methoxy or ethoxy, or trichloromethoxy. $L^2$ is halogen, in particular chlorine, imidazole, trichloromethoxy, O—C(O)—Cl or $C_1$-$C_4$-alkoxy, in particular methoxy or ethoxy. Examples of suitable compounds of the formula C(O)$L^1L^2$ are phosgene, diphosgene, triphosgene, methyl or ethyl chloroformiate, dimethylcarbonate, diethylcarbonate and carbonyldiimidazole. The reaction of IX with C(O)$L^1L^2$ can be achieved by analogy to the processes described in WO 2007/43677.

According to a further aspect, the invention relates to a process for preparing a compound of the formula V. This process is hereinafter termed "process B". Process B comprises reacting a compound of the formula I as described above with a compound of formula VI.

In formulae V and VI, the variables p, r, t, Q, $R^1$, $R^2$, $R^3$, $R^4$, $R^5$ and $R^6$ are as defined above and in the claims. In particular, p, t, $R^1$, $R^2$, $R^3$ and $R^4$ have the meanings which are give above as preferred or particular meanings in context with formula I.

In formulae V and VI, the variables r, Q, $R^5$ and $R^6$, alone or in combination, preferably have the following meanings:

r is 1;
Q is N;
$R^5$ is selected from the group consisting of halogen, $C_1$-$C_4$-fluoroalkyl, $CBrF_2$, $C_1$-$C_4$-alkoxy and $C_1$-$C_4$-fluoroalkoxyalkyl, such as $CH_2OCHF_2$, and in particular selected from the group consisting of halogen, such as chlorine or bromine, $CF_3$, $CHF_2$, $CBrF_2$ and methoxy.
$R^6$ is selected from the group consisting of halogen and $C_1$-$C_4$-fluoroalkyl, in particular selected from the group consisting of halogen and $CF_3$.

Particular preference is given to compounds of the formulae V and VI, wherein r is 1 and where $R^6$ is located in the ortho position with regard to the point of attachment of the pyrazole nitrogen. In this case, $R^6$ is in particular selected from the group of halogen and $C_1$-$C_4$-fluoroalkyl, especially selected from the group consisting of halogen and $CF_3$, and more particularly $R^6$ is chlorine.

Suitable leaving groups X in formula VI are halogen, in particular chlorine, OH, and radicals which are derived from activated ester groups such as 4-nitrophenoxy, pentafluorophenoxy, tosylate, mesylate or triflate.

Particular preference is given to compounds of the formula V, wherein p is 0, 1 or 2. Preference is given to compounds V, where p=1 and where the one radical $R^3$ is located in ortho- or para position with regard to the group $NR^4$. Preference is also given to compounds V, where p=2 and where, one radical $R^3$ is located in ortho position while the other radical $R^3$ is located in para position with regard to the group $NR^4$.

Particular preferred compounds of the formulae V and VI are represented by the following formulae Va and VIa:

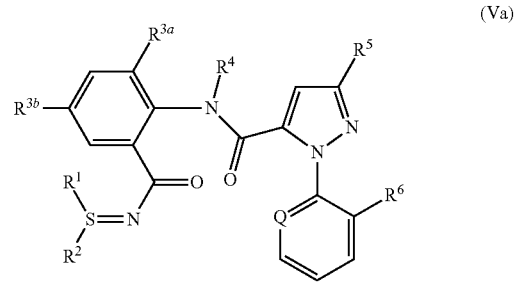

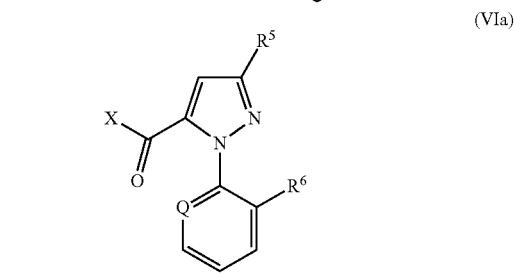

where Q, X, $R^1$, $R^2$, $R^4$, $R^5$ and $R^6$ are as defined herein and where $R^{3a}$ is hydrogen or has one of the meanings given herein for $R^3$ and $R^{3b}$ is hydrogen or has one of the meanings given herein for $R^3$.

In formula Va the radicals $R^{3a}$ and $R^{3b}$ are, independently of each other, preferably selected from the group consisting of hydrogen, halogen, $C_1$-$C_4$-alkyl, $C_1$-$C_4$-haloalkyl and cyano, it being possible that $R^{3a}$ and $R^{3b}$ are identical or different. In formula IIa the radical $R^{3a}$ is in particular selected from the group consisting of hydrogen, halogen, in particular chlorine or bromine, methyl, and halomethyl, e.g. trifluoromethyl, difluoromethyl or bromodifluoromethyl. In formula IIa the radical $R^{3b}$ is in particular selected from the group consisting of hydrogen, halogen, in particular chlorine or bromine, cyano, methyl, and halomethyl, e.g. trifluoromethyl, difluoromethyl or bromodifluoromethyl.

In formula Va, $R^4$ is in particular hydrogen.

Particular examples of compounds of the formula V, which can be prepared by process B are the compounds of formula Va as defined in the following tables 47 to 414:

Tables 47 to 92: Compounds of formula Va, wherein Q is N, $R^6$ is chlorine, $R^5$ is methoxy, and where $R^1$, $R^2$, $R^4$, $R^{3a}$ and $R^{3b}$ are as defined in tables 1 to 46 above.

Tables 93 to 138: Compounds of formula Va, wherein Q is N, $R^6$ is chlorine, $R^5$ is chlorine, and where $R^1$, $R^2$, $R^4$, $R^{3a}$ and $R^{3b}$ are as defined in tables 1 to 46 above.

Tables 139 to 184: Compounds of formula Va, wherein Q is N, $R^6$ is chlorine, $R^5$ is bromine, and where $R^1$, $R^2$, $R^4$, $R^{3a}$ and $R^{3b}$ are as defined in tables 1 to 46 above.

Tables 185 to 230: Compounds of formula Va, wherein Q is N, $R^6$ is chlorine, $R^5$ is difluoromethyl, and where $R^1$, $R^2$, $R^4$, $R^{3a}$ and $R^{3b}$ are as defined in tables 1 to 46 above.

Tables 231 to 276: Compounds of formula Va, wherein Q is N, $R^6$ is chlorine, $R^5$ is trifluoromethyl, and where $R^1$, $R^2$, $R^4$, $R^{3a}$ and $R^{3b}$ are as defined in tables 1 to 46 above.

Tables 277 to 322: Compounds of formula Va, wherein Q is N, $R^6$ is chlorine, $R^5$ is cyano, and where $R^1$, $R^2$, $R^4$, $R^{3a}$ and $R^{3b}$ are as defined in tables 1 to 46 above.

Tables 323 to 368: Compounds of formula Va, wherein Q is N, $R^6$ is chlorine, $R^5$ is bromodifluoromethyl, and where $R^1$, $R^2$, $R^4$, $R^{3a}$ and $R^{3b}$ are as defined in tables 1 to 46 above.

Tables 369 to 414: Compounds of formula Va, wherein Q is N, $R^6$ is chlorine, $R^5$ is $CH_2OCHF_2$, and where $R^1$, $R^2$, $R^4$, $R^{3a}$ and $R^{3b}$ are as defined in tables 1 to 46 above.

Examples of compounds VI are those of formula VIa, wherein X is Cl, Q is N, $R^6$ is Cl and where $R^5$ is selected from the group consisting of chlorine, bromine, methoxy, trifluoromethyl, difluoromethyl, bromodifluoromethyl and $CH_2OCHF_2$. Further examples of compounds VI are those of formula VIa, wherein X is OH, Q is N, $R^6$ is Cl and where $R^5$ is selected from the group consisting of chlorine, bromine, methoxy, trifluoromethyl, difluoromethyl, bromodifluoromethyl and $CH_2OCHF_2$.

In process B, a compound of formula I or Ia is reacted with a pyrazole compound of formula VI or VIa to yield a compound of formula V or Va, respectively. The reaction of process B can be carried out by analogy to conventional amidation reactions of carboxylic acids, activated carboxylic acids or carboxylic acid chlorides with aromatic amines as described e.g. in WO 2003/015519, WO 2006/062978, WO 2008/07158 or WO 2009/111553. Surprisingly, the group $N=S(O)_xR^1R^2$ does not interfere with the amidation reaction. Rather, the compounds of formula V or Va, respectively, can be obtained in high yields with high purity. In a preferred embodiment of process B, a pyrazole compound VI or VIa is reacted, where X is halogen, in particular chlorine.

Usually, the compounds of formulae I or Ia and the compounds of formulae VI or Via are preferably employed in stoichiometric or almost stoichiometric amount. Generally, the relative molar ratio of the compounds of formulae I or Ia to the compounds of formulae VI or VIa will be in a range from 1.1:1 to 1:2, preferably from 1.1:1 to 1:1.2 and in particular from 1.05:1 to 1:1.1.

It has been found advantageous to carry out the reaction of process B in the presence of a base, in particular if X is halogen, in particular if X is chlorine. Suitable bases include bases which are soluble or insoluble in the reaction medium. The base may be used in catalytic or stoichiometric amounts. The amount of base may preferably be in the range from 0.9 to 2 mol, in particular from 1 to 1.8 mol per mol of compound VI.

Suitable bases include but are not limited to oxo bases and amine bases. Suitable oxo bases include but are not limited to carbonates, in particular alkalimetal carbonates, such as lithium, sodium or potassium carbonates, phosphates, in particular alkalimetal phosphates, such as lithium, sodium or potassium phosphate. Suitable amine bases include but are not limited to tertiary organic amines, in particular aliphatic or cycloaliphatic tertiary amines, e.g. tri-$C_1$-$C_4$-alkylamines, $C_3$-$C_6$-cycloalkyl-di-$C_1$-$C_4$-alkylamines, tertiary cyclic amines and pyridines such as dimethylcyclohexylamine, trimethylamine, triethylamine, N-methylpiperidine, N-methylmorpholine, pyridine, 2,6-dimethylpyridine, 2,4,6-trimethylpyridine or quinoline. Preferred bases are alkalimetal carbonates, such as lithium, sodium or potassium carbonates and tertiary amines in particular triethylamine, pyridine, 2,6-dimethylpyridine or 2,4,6-trimethylpyridine.

In addition to or instead of the base, an amidation catalyst can be used, in particular if X in formulae VI or VIa is halogen. Suitable amidation catalysts are dialkylaminopyridines such as 4-(N,N-dimethylamino)pyridine (4-DMAP). The catalyst is usually employed in amounts from 0.001 to 1 mol, in particular from 0.005 to 0.2 mol, especially from 0.01 to 0.1 mol per mol of compound of formulae V or Va.

In particular embodiments of the invention, the reaction of process B is carried out in an organic solvent or a mixture of organic solvents. Suitable solvents for carrying out reaction of process B are preferably aprotic solvents and mixtures thereof. Examples of aprotic solvents are aliphatic hydrocarbons, such as alkanes, e.g. pentane, hexane or heptane, octane, cycloaliphatic hydrocarbons, such as cycloalkanes, e.g. cyclopentane or cyclohexane, halogenated alkanes, such as methylene chloride, chloroform or 1,2-dichlorethane, aromatic hydrocarbons, such as benzene, toluene, the xylenes, mesitylene or chlorobenzene, open-chained ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, the aforementioned carbonates, in particular cyclic carbonates such as propylene carbonate, nitriles, such as acetonitrile or propionitrile, the aforementioned pyridines such as pyridine, 2,6-dimethylpyridine or 2,4,6-trimethylpyridine, N,N-di-$C_1$-$C_4$-alkylamides of aliphatic carboxylic acids such as N,N-dimethylformamide, N,N-dimethylacetamide, and N—$C_1$-$C_4$-alkyl lactames such as N-methyl pyrrolidinone. Particular preferred solvents for carrying out reaction of process B are cyclohexane, dichloromethane, chlorobenzene, toluene, pyridine, tetrahydrofuran, propylene carbonate and N,N-dimethyl formamide, and mixtures thereof.

The reaction according to process B is generally performed at a temperature in the range of from −40 to +150° C., preferably from 0 to 110° C. and more preferably from 30 to 80° C. In principle the reaction temperature can be as high as the boiling point of the reaction mixture at the given reaction pressure, but is preferably kept at the indicated lower values. The reaction pressure is generally not critical and may range from 0.9 to 2 bar, in particular from 0.9 to 1.5 bar and especially from 0.9 to 1.1 bar.

The reaction of process B is carried out by reacting a compound of formulae I or Ia with a suitable amount of a compound of formulae VI or VIa under the above reaction conditions. The reaction can be performed for example in the following manner: a solution or a suspension of the base and of the compound of formulae I or Ia in a suitable organic solvent is charged to a suitable reaction vessel. To this mixture, the compound of formulae VI or VIa is added, preferably as a solution or suspension in an organic solvent. Addition of the compound of formulae VI or VIa may be done as a single portion or preferably continuously or in several portions. To the resulting mixture, the catalyst may be added, if desired.

The catalyst may be added either neat, in solution or as a suspension in a suitable organic solvent.

The compound of formulae V or Va formed in reaction of process B can be isolated from the reaction mixture by customary methods, e.g. by removal of the base from the reaction mixture by either filtration or extraction with water, followed by concentration by distilling off the solvent. Alternatively, the reaction mixture can be diluted with water and cooled to a temperature between −30 and +30° C. to precipitate the amide compound from the solvent or solvent mixture. The precipitated amide compound V or Va can be separated from the liquid reaction mixture by conventional means, e.g. by filtration, centrifugation etc. The amide compound of formula V can also be isolated from the reaction mixture by addition of water to the reaction mixture and extracting the thus obtained mixtures with a suitable solvent. Suitable solvents for extraction purposes are essentially immiscible with water and are capable of dissolving sufficient amounts of compound V. It is also possible to concentrate the reaction mixture by distilling of the solvent, mixing the thus obtained residue with water and extracting the thus obtained mixture with a suitable solvent. Examples of suitable solvents are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride or chloroform, aromatic hydrocarbons, such as benzene, toluene, the xylenes or chlorobenzene, open-chained ethers, such as diethylether, methyl-tert-butyl ether or methyl-isobutyl ether, or esters, such as ethyl acetate or ethyl propionate.

The thus obtained compound of formulae V or Va can be further purified, e.g. by crystallization or by chromatography or combined measures. However, frequently, the product is already obtained in a purity which does not require further purification steps.

The compounds of formulae VI or VIa are known from prior art, e.g. from WO 2003/015519 or they can be prepared by analogy to the methods described therein.

The compounds of formulae VI or VIa, where X is Cl, may also be prepared in-situ by reacting a compound of formulae VI or VIa, where X is OH with a sulfonyl chloride, such as $SOCl_2$, oxalyl chloride, an alkylsulfonylchloride, e.g. a methanesulfonylchloride, or an arylsulfonylchloride, e.g. tosylchloride or benzenesulfonyl chloride, as described in WO 2006/062978, WO 2008/07158 or WO 2009/111553.

It has been found advantageous to prepare compounds of the formulae VI or VIa, respectively, wherein X is Cl (hereinafter compounds VI-1 or VIa-1, respectively), by the reaction depicted in scheme 3:

Scheme 3:

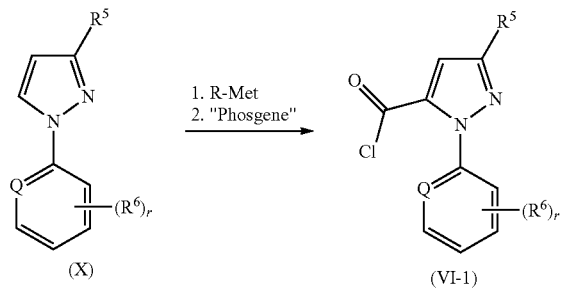

In scheme 3, the variables r, Q, $R^5$ and $R^6$ are as defined above. The reaction of scheme 3 is particularly successful, if Q is N. R-Met indicates a metal organic compound selected from lithium-organic base having a carbon or nitrogen bound lithium and magnesium-organic base having a carbon bound magnesium. "Phosgene" indicates phosgene itself and phosgene equivalents. Thus, the process of scheme 3 comprises:

i) deprotonating a compound of the formula X with a base selected from lithium-organic base having a carbon or nitrogen bound lithium or with a magnesium-organic base having a carbon bound magnesium; and ii) subjecting the product obtained in step (i) to a chlorocarbonylation by reacting it with a reagent selected from the group consisting of phosgene or a phosgene equivalent, to obtain a compound of formula VI-1.

The process according to scheme 3 is associated with a series of advantages as it overcomes several shortcomings of the prior art processes. For instance, the process of scheme 3 allows for the preparation of N-substituted 1H-pyrazole-5-carbonylchloride compounds of the formula VI-1 de facto in one process step, since the deprotonated intermediate obtained after reaction step i) is converted in-situ without prior work-up or purification into the product of formula VI-1. Also, after completion of the conversion the acid chloride VI-1 can be readily isolated and purified by means of a simple protocol including crystallization and solvent evaporation to remove unwanted byproducts. Furthermore, the deprotonation step is preferably carried out with an inexpensive Grignard reagent, which allows for selective and high-yielding conversions at moderate temperatures that can safely and smoothly carried out on an industrial scale.

The conversion in step (i) of the process according to scheme 3 is a deprotonation of the carbon atom in position 3 of the pyrazole ring of compound X, i.e. an abstraction of a proton in said position. This transformation is effected by contacting the starting compounds including a compound X with the base, preferably in a solvent, under suitable reaction conditions.

For the deprotonation reaction in step (i), bases selected from lithium-organic base having a carbon or nitrogen bound lithium and magnesium-organic base having a carbon bound magnesium, such as alkyl lithium, in particular n-butyl lithium, lithium dialkyl amide, in particular lithium diisopropylamide, and alkyl and cycloalkyl magnesium halides have to be used.

According to a preferred embodiment the base is selected from $C_1$-$C_6$-alkyl magnesium halides and $C_5$-$C_6$-cycloalkyl magnesium halides, more preferably selected from $C_1$-$C_4$-alkyl magnesium chlorides, $C_1$-$C_4$-alkyl magnesium bromides, $C_5$-$C_6$-cycloalkyl magnesium chlorides and $C_5$-$C_6$-cycloalkyl magnesium bromides, and in particular selected from methyl magnesium chloride, ethyl magnesium chloride, n-propyl magnesium chloride, isopropyl magnesium chloride, methyl magnesium bromide, ethyl magnesium bromide, n-propyl magnesium bromide and isopropyl magnesium bromide.

The base is generally used in an amount of 0.8 to 3.5 mol, preferably of 1.0 to 3.0 mol, in particular of 1.01 to 2.5 mol and especially of 1.1 to 2.2 mol, based in each case on 1 mol of the compound of the formula X. In case a lithium-organic base is employed for the conversion in step (i) it is used in an amount of typically 0.8 to 1.5 mol, more preferably of 0.95 to 1.4 mol and in particular of 1.0 to 1.3 mol, based in each case on 1 mol of the compound of the formula X. If a magnesium-organic base is employed, it is used in an amount of typically 1.0 to 3.5 mol, more preferably of 1.3 to 3.0 mol, in particular of 1.5 to 2.5 mol and especially of 1.7 to 2.2 mol, based in each case on 1 mol of the compound of the formula X.

If a magnesium-organic base such as $C_1$-$C_6$-alkyl magnesium halides and $C_5$-$C_6$-cycloalkyl magnesium halides is used as a base, it has been found advantageous to perform step (i) in the presence of an inert lithium salt. Suitable inert lithium salts are in particular lithium halides such as lithium chloride or lithium bromide but also, lithium sulphate, lithium carbonate and lithium alkoxides such as lithium methoxide or lithium ethoxide. In this embodiment, the amount of lithium salt will generally be from 0.8 to 1.5 mol, in particular from 0.9 to 1.1 mol, calculated as lithium, per mol of magnesium in the base.

The deprotonation of step (i) is usually performed in an aprotic organic solvent. Suitable aprotic organic solvents here include, for example, aliphatic $C_3$-$C_6$ ethers, such as dimethoxyethane, diethylene glycol dimethyl ether, dipropyl ether, methyl isobutyl ether, tert-butyl methyl ether and tert-butyl ethyl ether, alicyclic $C_3$-$C_6$ ethers, such as tetrahydrofuran (THF), tetrahydropyran, 2-methyltetrahydrofuran, 3-methyltetrahydrofuran and dioxane, aliphatic hydrocarbons, such as pentane, hexane, heptane and octane, and also petroleum ether, cycloaliphatic hydrocarbons, such as cyclopentane and cyclohexane, aromatic hydrocarbons, such as benzene, toluene, the xylenes and mesitylene, or mixtures of these solvents.

The solvent for the conversion in step (i) is preferably selected from aliphatic and alicyclic ethers, especially form $C_3$-$C_6$-aliphatic ethers and $C_4$-$C_6$ alicyclic ethers, or a mixture thereof. Particular preferably 1,2-dimethoxyethane or THF is used as solvent. If compound X is initially present in the reaction vessel in a solvent and also the base is added in a solvent, preferably the same solvent, in particular 1,2-dimethoxyethane or THF, is used in each case.

The total amount of the solvent used in step (i) of the process according to the invention is typically in the range from 500 to 6000 g and preferably in the range from 1000 to 5000 g, based on 1 mol of the compound X.

For the reaction of scheme 3, preference is given to solvents which are essentially anhydrous, i.e. have a water content of less than 1000 ppm and especially not more than 100 ppm.

In general, the reaction of step (i) is performed under temperature control employing a closed or unclosed reaction vessel with stirring and a cooling device.

A suitable temperature profile for the reaction in step (i) is determined by several factors, for example the reactivity of the compound X used and the type of base selected, and can be determined by the person skilled in the art in the individual case, for example by simple preliminary tests. Generally the deprotonation of step (i) will be performed at a temperature in the range from $-70$ to $+100°$ C., in particular from $-50$ to $+50°$ C.

The reactants can in principle be contacted with one another in any desired sequence. For example, the compound X, optionally dissolved in a solvent or in dispersed form, can be initially charged and then the base, optionally in dissolved or dispersed form, is added, or, conversely, the base, optionally dissolved or dispersed in a solvent, can be initially charged and admixed with the compound X. Alternatively, the two reactants can also be added simultaneously to the reaction vessel.

It has been found to be appropriate to initially charge the compound X, preferably in a solvent, and then adjust the reaction mixture to a temperature in the range of $-70$ to $30°$ C., preferably in the range of $-50$ to $25°$ C., depending on the reaction conditions of the individual case and in particular depending on the specific base to be used.

Afterwards the base, optionally in a solvent, is added either stepwise, continuously or in one portion and the reaction is allowed to continue for a period of time, possibly at the same temperature, at an elevated temperature or at a gradually rising temperature.

If, according to particular preferred embodiment of the invention, a magnesium-organic base is used for the conversion in step (i), compound X and the base are brought into contact at a set temperature typically in the range of $-30$ to $35°$ C., preferably of $-20$ to $30°$ C. and in particular of $-10$ to $25°$ C. or ambient temperature. Afterwards the conversion is usually continued either at the set temperature or by applying a temperature gradient with the set temperature as the lower limit and an upper limit in the range of $-20$ to $35°$ C., preferably of $-15$ to $30°$ C. and in particular of $-5$ to $25°$ C. or ambient temperature.

The reaction product obtained from the conversion in step (i) of the process of scheme 3 is usually subjected without preceding work-up to the conversion in step (ii) of the process according to the first aspect the invention. To this end, typically the reaction mixture obtained after the completion of the conversion in step (i) is directly introduced to the conversion in step (ii).

The conversion in step (ii) of the process according to the process of scheme 3 is a chlorocarbonylation of the intermediate product obtained in step (i) of the process. This conversion comprises an electrophilic attack of a chlorocarbonyl moiety $ClC(O)^+$ on the deprotonated carbon atom in position 5 of the pyrazole ring of the intermediate derived from compound X. Said electrophilic attack results in the covalent attachment of the chlorocarbonyl group and, as a consequence, in the formation of the N-substituted 1H-pyrazole-5-carbonylchloride compound VI. This reaction is effected by contacting the intermediate obtained in step (i) with phosgene or a phosgene equivalent, preferably in a solvent, under suitable reaction conditions.

Suitable phosgene equivalents are compounds which have a chlorocarbonyl moiety, such as in particular diphosgene (i.e. trichloromethyl chloroformate). However, phosgene is preferred as chlorocarbonylation reagent in step (ii).

The reactants can in principle be contacted with one another in any desired sequence. For example, the reaction mixture obtained from step (i) that contains the intermediate product resulting from the deprotonation in step (i), optionally mixed with additional solvent, can be initially charged and then a reagent selected from phosgene and phosgene equivalents, optionally in dissolved or dispersed form, is added, or, conversely, the reagent, optionally dissolved or dispersed in a solvent, can be initially charged and admixed with said intermediate. Alternatively, the two reactants can also be added simultaneously to the reaction vessel.

In case the reaction mixture of step (i) is admixed with additional solvent before the chlorocarbonylation in step (ii) is initiated, said additional solvent is an aprotic solvent which in particular is selected from the aprotic organic solvents mentioned herein before, especially from those mentioned as preferred. Preferably, the additional solvent is essentially anhydrous, i.e. it has a water content of less than 1000 ppm and especially not more than 100 ppm.

Typically the phosgene or phosgene equivalent is introduced into the reaction of step (ii) dissolved or dispersed in a suitable solvent that is generally selected from the apolar aprotic organic solvents mentioned before.

According to a preferred embodiment of the invention the chlorocarbonylation in step (ii) is effected with a solution of phosgene or phosgene equivalent in an aromatic hydrocarbon solvent, such as benzene, toluene, the xylenes or mesitylene, in particular toluene. The phosgene solution usually has a concentration of 3 to 40% by weight, preferably 10 to 30% by weight and specifically of about 20% by weight.

The chlorocarbonylation reagent, i.e. phosgene or phosgene equivalent, is usually employed in step (ii) in an amount of 0.5 to 5 mol, preferably of 0.8 to 4.0 mol, more preferably of 0.95 to 2.5 mol and in particular of 1.0 to 2.2 mol, based in each case on 1 mol of the compound of the formula (X) as originally introduced in step (i).

In general, the conversion in step (ii) is performed under temperature control employing a closed or unclosed reaction vessel with stirring and a cooling device.

A suitable temperature profile for the reaction in step (ii) is determined by several factors, in particular the type of base that was used in the deprotonation of step (i), the reactivity of the intermediate obtained in step (i) and the chlorocarbonylation reagent selected, and can be determined by the person skilled in the art for each individual case by conventional measures, such as preliminary tests. Generally the reaction will be performed at temperatures ranging from −70 to +100° C., in particular from −50 to +50° C.

Frequently, the reaction mixture obtained after completion of step (i) is adjusted to a temperature in the range of −30 to 50° C., preferably in the range of −10 to 25° C., if required, and then the chlorocarbonylating reagent, optionally dissolved in a solvent is added. The reaction is allowed to continue for a period of time, possibly at the same temperature, or alternatively at an elevated or gradually rising temperature.

If a magnesium-organic base has been used for the conversion in step (i), the intermediate from step (i) and the reagent are brought into contact in step (ii) at a set temperature typically in the range of −30 to 35° C., preferably of −10 to 30° C. and in particular of −5 to 25° C. or ambient temperature. Afterwards the conversion is usually continued either at the set temperature or by applying a temperature gradient with the set temperature as the lower limit and an upper limit in the range of −10 to 50°, preferably of −5 to 40° C. and in particular of 0 to 25° C. or ambient temperature, and then optionally allow the reaction to proceed at the upper limit temperature.

The reaction mixture obtained after the conversion in step (ii), that contains the N compound of the formula VI as product, is usually subjected to a workup procedure before introducing it to a subsequent reaction step. The workup is typically effected by non-aqueous means known in the art to be applicable for similar reactions. Preferably, the reaction mixture, optionally after mixing it with an apolar aprotic solvent, that usually is an aliphatic ether, an acyclic ether, an aromatic hydrocarbon, in particular diethyl ether or toluene and specifically toluene, is worked-up by filtering off solids that may be present. The filtered solids, if present, are washed with the solvent, the combined filtrate is concentrated by evaporation and the residue is extracted with an apolar aprotic solvent that typically is the same as used before. Undissolved solids are again filtered off, washed with the solvent and the product is isolated from the resulting filtrate by removing solvents via evaporation. The raw compound VI thus obtained can be used directly in the process B or sent to other uses. Alternatively, it can be retained for a later use or further purified beforehand. For further purification, it is possible to use one or more methods known to those skilled in the art, for example recrystallization, distillation, sublimation, zone melting, melt crystallization or chromatography. It is however preferred to subject compound VI to a subsequent synthetic step in the form of the raw material obtained directly after the workup procedure.

The compounds of formula X are known e.g. from WO 2003/015519 or WO 2003/106427 or they can be prepared by analogy to the methods described therein or in WO 2008/126858, WO 2008/126933, WO 2008/130021, WO 2007/043677 and Bioorganic and Medicinal Chemistry Letters 2005, 15, 4898-4906. The compounds of formula X, wherein $R^5$ is a C-bound radical $R^{5a}$ as defined below (Compounds X') can e.g. prepared by the reaction sequence depicted in the following scheme 4.

Scheme 4:

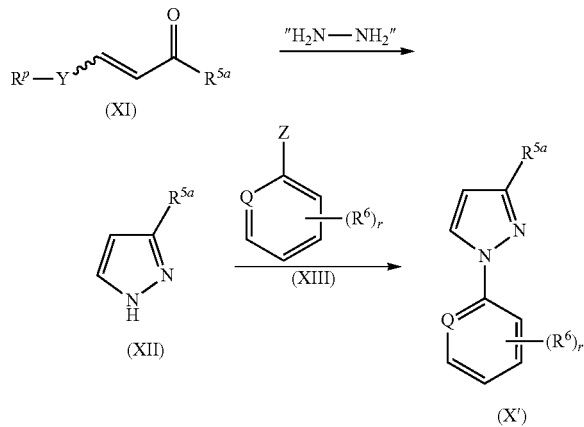

In scheme 4, the variables r, Q and $R^6$ are as defined above. The variables Y, Z, $R^{5a}$ and $R^p$ have the following meanings:

Y is O or S;

Z is a suitable leaving group such as halogen, $C_1$-$C_3$-alkoxy, $C_1$-$C_3$-alkylthio, $C_1$-$C_3$-haloalkoxy, $C_1$-$C_3$-haloalkylthio, —S(O)$R^{bb}$, —S(O)$_2R^{bb}$, —OS(O)$R^{bb}$, —OS(O)$_2R^{bb}$ and —NO$_2$, where $R^{bb}$ has one of the meanings given for $R^b$ above, and where $R^{bb}$ is in particular $C_1$-$C_4$-alkyl, $C_1$-$C_4$-haloalkyl or phenyl, which is unsubstituted or which carries 1, 2 or 3 radicals selected from halogen and $C_1$-$C_4$-alkyl;

$R^{5a}$ is $C_1$-$C_8$-alkyl, $C_1$-$C_8$-haloalkyl, $C_3$-$C_8$-cycloalkyl, $C_3$-$C_8$-halocycloalkyl, $C_2$-$C_8$-alkenyl, $C_2$-$C_8$-haloalkenyl, $C_2$-$C_8$-alkynyl, $C_2$-$C_8$-haloalkynyl, wherein the eight last radicals may optionally be substituted by one or more radicals $R^a$, phenyl which may be substituted by 1, 2, 3, 4 or 5 radicals $R^e$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals $R^e$;

$R^p$ is selected from the group consisting of $C_1$-$C_6$-alkyl, $C_1$-$C_6$-cycloalkyl, $C_1$-$C_6$-haloalkyl and $C_1$-$C_6$-halocycloalkyl;

The reaction of scheme 4 is particularly successful, if Q is N. Apart from that, the variables r, Q, Y, Z, $R^p$, $R^{5a}$ and $R^6$ on their own and in particular in combination have the following meanings:

r is 1;

Q is N;

Y is O;

Z is halogen, —S(O)$_2R^{bb}$ or —OS(O)$R^{bb}$, where $R^{bb}$ is as defined above, and where $R^{bb}$ is in particular $C_1$-$C_4$-alkyl;

$R^p$ is $C_1$-$C_6$-alkyl;

$R^{5a}$ is selected from the group consisting of $C_1$-$C_4$-fluoroalkyl, CBrF$_2$ and $C_1$-$C_4$-fluoroalkoxyalkyl, such as $CH_2OCHF_2$, and in particular selected from the group consisting of $CF_3$, $CHF_2$, $CBrF_2$ and $CH_2OCHF_2$;

$R^6$ is selected from the group consisting of halogen and $C_1$-$C_4$-fluoroalkyl, in particular selected from the group consisting of halogen and $CF_3$, with particular preference given to compounds of the formula X', wherein r is 1 and where $R^6$ is located in the ortho position with regard to the point of attachment of the pyrazole nitrogen. In this case, $R^6$ is in particular selected from the group of halogen and $C_1$-$C_4$-fluoroalkyl, especially selected from the group consisting of halogen and $CF_3$, and more particularly $R^6$ is chlorine.

Thus, in a first step the process of scheme 4 comprises reacting a compound of formula XI with hydrazine or hydrazine hydrate or a salt thereof. In a second step the thus obtained pyrazole compound of formula XII is reacted with a phenyl compound (XIII; Q=CH) or a pyridine compound (XIII; Q=N) to yield the compound of formula X'. The reactions of the first and the second step can be performed by analogy to the methods described in WO 2008/126858, WO 2008/126933, WO 2008/130021, WO 2007/043677 and Bioorganic and Medicinal Chemistry Letters 2005, 15, 4898-4906.

According to the first reaction depicted in scheme 4, a compound of formula XI is reacted with hydrazine or hydrazine hydrate or a salt thereof. The reaction is usually achieved by contacting the compound of formula XI with hydrazine or hydrazine hydrate or a salt thereof in a solvent.

Suitable solvents include water and polar protic organic solvents and mixtures thereof. Examples of suitable polar protic solvents, which can be used in step 1 of scheme 4 are in particular alcohols, such as $C_1$-$C_4$-alkanols, $C_2$-$C_4$-alkandiols, e.g. ethylene glycol or propylene glycol, di- and tri-$C_2$-$C_3$-alkylene ethers, such as diethylene glycol or triethylene glycol, mono-$C_1$-$C_4$-alkylethers, in particular monomethylethers of $C_2$-$C_4$-alkandiols, e.g. ethylene glycol monomethyl ether, or mono-$C_1$-$C_4$-alkylethers, in particular monomethylethers of di- or tri-$C_2$-$C_3$-alkylene ethers and mixtures thereof. Preferred organic solvents are selected from the group of $C_1$-$C_4$-alkanols with particular preference given to ethanol.

The hydrazine or hydrazine salt is preferably employed in an amount of from 0.7 to 10 mol, preferably from 0.9 to 5 mol and in particular from 1 to 3 mol per mol of the compound of formula XI.

It has been found advantageous to carry out the first reaction of scheme 4 in the presence of an acid. The acid may be used in catalytic or stoichiometric amounts. The amount of base may preferably be used in catalytic amounts, e.g. in an amount from 0.001 to 0.2 mol, in particular in an amount from 0.01 to 0.1 mol per mol of compound XI. Suitable acids are in particular strong acids such as hydrochloric acid, sulphuric acid, nitric acid, or organic sulfonic acids such as alkylsulfonic acids or arylsulfonic acids.

The reaction according to the first reaction depicted in scheme 4 is generally performed at a temperature in the range of from 0 to 150° C., preferably from 10 to 120° C. In principle the reaction temperature can be as high as the boiling point of the reaction mixture at the given reaction pressure. The reaction pressure is generally not critical and may range from 0.9 to 2 bar, in particular from 0.9 to 1.5 bar and especially from 0.9 to 1.1 bar.

The thus obtained pyrazole can be isolated from the reaction mixture by conventional techniques, e.g. by distillation or extraction. Generally, the acid, if present, is neutralized prior to isolation of the pyrazole compound.

According to the second reaction depicted in scheme 4, a compound of formula XIII is reacted with the pyrazole compound XII. The amount of compound XII is generally from 0.8 to 1.2 mol, in particular from 0.9 to 1.1 mol per mol of compound XIII.

The reaction is usually achieved by contacting the compound of formula XII with the compound XIII in a solvent. In particular embodiments of the invention, the second reaction depicted in scheme 4 is carried out in an aprotic organic solvent or a mixture of aprotic organic solvents. Examples of suitable aprotic solvents are halogenated alkanes, such as methylene chloride, chloroform or 1,2-dichlorethane, aromatic hydrocarbons, such as toluene, xylenes or chlorobenzene, open-chained ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, N,N-di-$C_1$-$C_4$-alkylamides of aliphatic carboxylic acids such as N,N-dimethyl formamide, N,N-dimethyl acetamide, N—$C_1$-$C_4$-alkyl lactames such as N-methyl pyrrolidinone, sulfoxides such as dimethylsulfoxide, nitriles such as acetonitrile or propionitrile and pyridines such as pyridine, 2,6-dimethylpyridine or 2,4,6-trimethylpyridine. Preferably the reaction is carried out a polar aprotic solvent, in particular in a solvent selected from N,N-di-$C_1$-$C_4$-alkylamides of aliphatic carboxylic acids such as N,N-dimethyl formamide or N,N-dimethyl acetamide, and N—$C_1$-$C_4$-alkyl lactames such as N-methyl pyrrolidinone.

It has been found advantageous to carry out the second reaction of scheme 4 in the presence of a base. The base may be used in catalytic or stoichiometric amounts. The amount of base may preferably be used in at least almost stoichiometric amounts, e.g. in an amount from 0.9 to 5 mol, in particular in an amount from 1 to 2 mol per mol of compound XII. Suitable bases are in particular oxo bases. Suitable oxo bases include but are not limited to those mentioned in context with the reaction of process A. Preferred bases are alkalimetal carbonates, especially sodium, potassium and cesium carbonate.

The reaction according to the first reaction depicted in scheme 4 is generally performed at a temperature in the range of from 50 to 200° C., preferably from 100 to 180° C. In principle the reaction temperature can be as high as the boiling point of the reaction mixture at the given reaction pressure. The reaction pressure is generally not critical and may range from 0.9 to 2 bar, in particular from 0.9 to 1.5 bar and especially from 0.9 to 1.1 bar.

The compound of formula X' formed in this reaction can be isolated from the reaction mixture by customary methods, e.g. by distillation or by crystallization or precipitation from the reaction mixture, preferably after having removed insoluble by products. The compound of formula X' can also be isolated from the reaction mixture by addition of water to the reaction mixture and extracting the thus obtained mixtures with a suitable solvent. Suitable solvents for extraction purposes are essentially immiscible with water and are capable of dissolving sufficient amounts of compound X'. It is also possible to concentrate the reaction mixture by distilling of the solvent, mixing the thus obtained residue with water and extracting the thus obtained mixture with a suitable solvent. Examples of suitable solvents are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride or chloroform, aromatic hydrocarbons, such as benzene, toluene, the xylenes or chlorobenzene, open-chained ethers, such as diethylether, methyl-tert-butyl ether or methyl-isobutyl ether, or esters, such as ethyl acetate or ethyl propionate.

The isolated product X' can be further purified, e.g. by crystallization or destillation. However, frequently, the product is already obtained in a purity which does not require further purification steps.

Vinyl(thio)ether compounds of formula XI are either commercially available on a large scale or easily produced using standard methods of organic chemistry, a skilled person is familiar with. Likewise, the compounds of formula XIII are readily available or can be prepared by analogy to routine methods of organic chemistry.

The reactions described herein are carried out in reaction vessels customary for such reactions, the reaction being configurable continuously, semicontinuously or batchwise.

The compounds of the formula I as described herein are particularly useful, as they allow an efficient synthesis of the pesticide carboxamide compounds of the formula V in high overall yields and high purity.

The compounds of formula I and their salts, however, themselves show pesticidal activity, in particular herbicidal activity. Thus, they can be used for controlling/combating undesired plant growth.

Therefore, further objects of the present invention relate to the use of the compounds of formula I for controlling/combating undesired plant growth and to a method for combating undesired plant growth, wherein a compound of formula I or a salt thereof is applied to plants to be controlled or to their habitat and/or on seeds.

The invention thus also relates to plant protection agents containing a compound of formula I or a salt thereof and additives usual for the formulation of plant protection agents.

The compounds of formula I and the salts thereof as well as plant protection agents which contain a compound of formula I or a salt thereof combat plant growth, in particular monocotyledonous weed species such as *Avena, Lolium, Alopecurus, Phalaris, Echinochloa, Digitaria, Setaria, Cyperus* species, *Agropyron, Cynodon, Imparato* and *Sorghum*, and dicotyledonous weed species such as *Galium, Viola, Veronica, Lamium, Stellaria, Amaranthus, Sinapsis, Ipomoea, Matricaria, Abutilon, Sida, Convolvulus, Cirsium, Rumex* and *Artemisia* on non-cultivated areas very well, particularly at high application levels. In crops such as wheat, barley, rye, rice, maize, sugar beet, soya and cotton, they are active against weeds and noxious grasses, without harming the crop plants significantly. This effect occurs above all at low application levels.

Moreover, the compounds of the formula I and their salts are particularly useful for controlling invertebrate pests, in particular for controlling arthropods and nematodes and especially insects. Therefore, the invention relates to the use of the compounds of the formula I and their salts as pesticides for controlling invertebrate pests, in particular for controlling arthropods and nematodes and especially insects.

Moreover, the present invention also relates to and includes the following embodiments:

an agricultural or veterinary composition comprising at least one compound of formula (I) or a salt, in particular an agriculturally or veterinarily acceptable salt thereof, and at least one liquid and/or solid carrier.

a method for combating or controlling invertebrate pests, which method comprises contacting said pest or its food supply, habitat or breeding grounds with a pesticidally effective amount of at least one compound of formula (I) or a salt, in particular an agriculturally or veterinarily acceptable salt thereof, or a composition as defined herein.

a method for protecting growing plants from attack or infestation by invertebrate pests, which method comprises contacting a plant, or soil or water in which the plant is growing, with a pesticidally effective amount of at least one compound of formula (I) or a salt, in particular an agriculturally or veterinarily acceptable salt thereof, or a composition as defined herein.

a method for the protection of plant propagation material, especially seeds, from soil insects and of the seedlings' roots and shoots from soil and foliar insects comprising contacting the plant propagation material respectively seeds before sowing and/or after pregermination with at least one compound of formula (I) or a salt, in particular an agriculturally or veterinarily acceptable salt thereof, or a composition as defined herein.

seed comprising a compound of formula (I) or a salt, in particular an agriculturally or veterinarily acceptable salt thereof, preferably in an amount of from 0.1 g to 10 kg per 100 kg of the plant propagation material.

use of a compound of formula (I) or a salt, in particular an agriculturally or veterinarily acceptable salt thereof, or a composition as defined herein for combating or controlling invertebrate pests of the group of insects, arachnids or nematodes.

use of a compound of formula (I) or a stereoisomer or agriculturally or veterinarily acceptable salt thereof, or a composition as defined herein for protecting growing plants from attack or infestation by invertebrate pests.

use of a compound of formula (I) or a salt, in particular a veterinarily acceptable salt thereof or a composition as defined herein for combating or controlling invertebrate parasites in and on animals.

a method for treating a non-human animal infested or infected by parasites or for preventing a non-human animal from getting infested or infected by parasites or for protecting a non-human animal against infestation or infection by parasites which comprises orally, topically or parenterally administering or applying to the non-human animal a parasiticidally effective amount of a compound of formula (I) or a salt, in particular a veterinarily acceptable salt thereof or a composition as defined in claim herein.

a compound of formula (I) or a salt, in particular a veterinarily acceptable salt thereof for use as a medicament.

a compound of formula (I) or a salt, in particular a veterinarily acceptable salt thereof for use in the treatment, control, prevention or protection of animals against infestation or infection by parasites.

The compounds of the formula I, and their stereoisomers, N-oxides and salts, are in particular suitable for efficiently controlling arthropodal pests such as arachnids, myriapedes and insects as well as nematodes. The compounds of the formula I are especially suitable for efficiently combating the following pests:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella,*

*Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Putella xyostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyillobius pyri, Phyllotreta chrysocephala, Phyllophaga* sp., *Phyllopertha horticola, Phyillotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa,* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis;* bugs, aphids, leafhoppers, whiteflies, scale insects, cicadas (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantii* and, *Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina,* arachnoidea, such as arachnids (Acarina), e.g. of the families Argasidae, Ixodidae and Sarcoptidae, such as *Amblyo-*

*mma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Orithonyssus bacoti, Otobius megnin, Dermanyssus gallinae, Psoroptes ovis, Rhipicephalus sanguineus, Rhipicephalus appendiculatus, Rhipicephalus evertsi, Sarcoptes scabiei* and Eriophyidae spp. such as *Aculus schlechtendai, Phyllocoptrata oleivora* and *Eriophyes sheldoni*, Tarsonemidae spp. such as *Phytonemus pallidus* and *Polyphagotarsonemus latus*; Tenuipalpidae spp. such as *Brevipalpus phoenicis*, Tetranychidae spp. such as *Tetranychus cinnabarinus, Tetranychus kanzawai, Tetranychus pacificus, Tetranychus telarius* and *Tetranychus urticae, Panonychus ulmi, Panonychus citri*, and *Oligonychus pratensis*; Araneida, e.g. *Latrodectus mactans*, and *Loxosceles reclusa;* fleas (Siphonaptera), e.g. *Ctenocephalides felis, Ctenocephalides canis, Xenopsylla cheopis, Pulex irritans, Tunga penetrans*, and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

The compounds of the present invention, including their salts, N-oxides and stereoisomers are also suitable for controlling nematodes, especially plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species, *Heterodera avenae, Heterodera glycines, Heterodera schachtii, Heterodera trifolii*, and other *Heterodera* species; Seed gall nematodes, *Anguina* species; Stem and foliar nematodes, Aphelenchoides species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, Criconemoides species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, Hemicycliophora species and Hemicriconemoides species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of the present invention, including their salts, N-oxides and stereoisomers are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei*, and Eriophyidae spp. such as *Aculus schlechtendali, Phyllocoptrata oleivora* and *Eriophyes sheldoni*; Tarsonemidae spp. such as *Phytonemus pallidus* and *Polyphagotarsonemus latus*; Tenuipalpidae spp. such as *Brevipalpus phoenicis*; Tetranychidae spp. such as *Tetranychus cinnabarinus, Tetranychus kanzawai, Tetranychus pacificus, Tetranychus telarius* and *Tetranychus urticae, Panonychus ulmi, Panonychus citri*, and *Oligonychus pratensis*.

Compounds of the formula I are particularly useful for controlling insects, preferably sucking or piercing insects such as insects from the genera Thysanoptera, Diptera and Hemiptera, and chewing-biting pests such as insects from the genera of Lepidoptera, in particular the following species:

Thysanoptera: *Frankliniella fusca, Frankliniella occidentalis, Frankliniella tritici Scirtothrips citri, Thrips oryzae, Thrips palmi* and *Thrips tabaci,*

Diptera, e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola*, and *Tabanus similis, Tipula oleracea*, and *Tipula paludosa,*

Hemiptera, in particular aphids: *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae,*

*Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand*, and *Viteus vitifolii*.

Lepidoptera, in particular: *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Putella xyostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*.

The invention also relates to agrochemical compositions comprising an auxiliary and at least one compound I according to the invention.

An agrochemical composition comprises a pesticidally effective amount of a compound I. The term "effective amount" denotes an amount of the composition or of the compounds I, which is sufficient for controlling invertebrate pests on cultivated plants or in the protection of materials and which does not result in a substantial damage to the treated plants or material. Such an amount can vary in a broad range and is dependent on various factors, such as the invertebrate (e.g. insect) species to be controlled, the treated cultivated plant or material, the climatic conditions and the specific compound I used.

The compounds I, their stereoisomers, N-oxides and salts can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides.

Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones. Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)

5-25 wt % of a compound I according to the invention and 1-10 wt % dispersant (e.g. polyvinylpyrrolidone) are dissolved in up to 100 wt % organic solvent (e.g. cyclohexanone). Dilution with water gives a dispersion.

iii) Emulsifiable Concentrates (EC)

15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)

5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

iv) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

iv) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.

ix) Dustable Powders (DP, DS)

1-10 wt % of a compound I according to the invention are ground finely and mixed intimately with up to 100 wt % solid carrier, e.g. finely divided kaolin.

x) Granules (GR, FG)

0.5-30 wt % of a compound I according to the invention is ground finely and associated with up to 100 wt % solid carrier (e.g. silicate). Granulation is achieved by extrusion, spray-drying or the fluidized bed.

xi) Ultra-low volume liquids (UL)

1-50 wt % of a compound I according to the invention are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.001 to 1 kg per ha, more preferably from 0.005 to 0.9 kg per ha, in particular from 0.005 to 0.5 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially pre-mixed components, e. g. components comprising compounds I and/or active substances from the groups A) to O), may be mixed by the user in a spray tank and further auxiliaries and additives may be added, if appropriate.

In a further embodiment, either individual components of the composition according to the invention or partially pre-mixed components, e. g. components comprising compounds I and/or active substances from the groups A) to O), can be applied jointly (e.g. after tank mix) or consecutively.

The application of the compounds of formula I or the salts thereof or the herbicidal agents or pesticidal agents containing them is effected, if the formulation is not already ready for use, in the form of aqueous spray fluids. These are prepared by dilution of the aforesaid formulations containing the compound of formula I or a salt thereof with water. The spray fluids can also contain other components in dissolved, emulsified or suspended form, for example fertilizers, active substances of other herbicidal or growth-regulating active substance groups, other active substances, for example active substances for combating animal pests or phyto-pathogenic fungi or bacteria, and also mineral salts which are used for the elimination of nutritional and trace element deficiencies, and non-phytotoxic oils and oil concentrates. As a rule, these components are added to the spray fluid before, during or after the dilution of the formulations according to the invention.

For herbicide treatment, the application of the compound of formula I or a salt thereof or of the plant protection agents containing them can be effected in a pre-emergence or in a post-emergence method. If the compound of formula I or a salt thereof is less tolerable for certain crop plants, application techniques can be used wherein the herbicidal agents are sprayed using the spraying equipment in such a manner that the leaves of the sensitive crop plants are as far as possible not hit, while the active substances reach the leaves of undesired plants growing under them or the uncovered soil surface (post-directed, lay-by).

The compounds of the formula I or their salts may be used together with one or more further active ingredients, including herbicides, growth regulators, safeners, fertilizers, agents for combating invertebrate pests, such as insecticides or nematicides, agents for combating phytopathogenic fungi, i.e. fungicides, or agents for combating bacteria.

For herbicide treatment, the quantities of the compound of formula I or a salt thereof applied are 0.001 to 3.0 kg active substance per hectare, preferably 0.01 to 1.0 kg active substance (a·S)/ha, depending on the treatment aim, season, target plants and growth stage.

To broaden the spectrum of action and to achieve synergistic effects in the herbicide treatment, the compound of formula I or a salt thereof can be mixed and applied together with many members of other herbicidal or growth regulating active substance groups. In addition, it can be advantageous to formulate or apply the compounds of formula I or their salts together with safeners.

In addition, it can be of value to apply the compound of formula I or a salt thereof alone or in combination with other herbicides also mixed with still further plant protection agents, together for example with agents for combating invertebrate pests, such as insecticides or nematicides, or agents for combating phytopathogenic fungi, i.e. fungicides, or agents for combating bacteria. Also of interest is the miscibility with mineral salt solutions which are used for the elimination of nutritional and trace element deficiencies, i.e. fertilizers such as ammonium nitrate, urea, potash, and superphosphate. Additives such as non-phytotoxic oils and oil concentrates can also be added.

These additional active compounds or fertilizers may be used sequentially or in combination with the above-described compositions, if appropriate also added only immediately prior to use (tank mix). For example, the plant(s) may be sprayed with a composition of this invention either before or after being treated with other active ingredients.

Therefore, the present invention also relates to a mixture or composition comprising at least one compound of formula (I), or a salt, in particular an agriculturally or veterinarily acceptable salt thereof, and at least one further pesticide.

The following categorized list M of pesticides represents insecticidal mixture partners, which are, whenever possible, classified according to the Insecticide Resistance Action Committee (IRAC), and together with which the compounds according to the present invention may be used. The combined use of the compounds of the present invention with the following pesticides may result in potential synergistic effects. The following examples of insecticidal mixing partners are provided with the intention to illustrate the possible combinations, but not to impose any limitation to the obtainable mixtures:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, ometboate, oxydemetonmethyl, parathion, parathion-methyl, phenthoate, phorate, phosalone, phosmet, phosphamidon, phoxim, pirimiphosmethyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb, or M.7C pyriproxyfen;

M.8 miscellaneous non-specific (multi-site) inhibitors, for example

M.8A alkyl halides as methyl bromide and other alkyl halides, or

M.8B chloropicrin, or

M.8C sulfuryl fluoride, or

M.8D borax, or

M.8E tartar emetic;

M.9 Selective homopteran feeding blockers, for example

M.9B pymetrozine, or

M.9C flonicamid;

M.10 Mite growth inhibitors, for example

M.10A clofentezine, hexythiazox and diflovidazin, or

M.10B etoxazole;

M.11 Microbial disruptors of insect midgut membranes, for example *Bacillus thuringiensis* or *Bacillus sphaericus* and the insecticidal proteins they produce such as *Bacillus thuringiensis* subsp. *israelensis, Bacillus sphaericus, Bacillus thuringiensis* subsp. *aizawai, Bacillus thuringiensis* subsp. *kurstaki* and *Bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example

M.12A diafenthiuron, or

M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example
  M.20A hydramethylnon, or
  M.20B acequinocyl, or
  M.20C fluacrypyrim;

M.21 Mitochondrial complex I electron transport inhibitors, for example
  M.21A METI acaricides and insecticides such as fenazaquin, fenpyroximate, pyrimidifen, pyridaben, tebufenpyrad or tolfenpyrad, or
  M.21B rotenone;

M.22 Voltage-dependent sodium channel blockers, for example
  M.22A indoxacarb, or
  M.22B metaflumizone;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example
  M.24A phosphine such as aluminium phosphide, calcium phosphide, phosphine or
  zinc phosphide, or
  M.24B cyanide.

M.25 Mitochondrial complex II electron transport inhibitors, such as beta-ketonitrile derivatives, for example cyenopyrafen or cyflumetofen;

M.26 Ryanodine receptor-modulators from the class of diamides, as
  for example flubendiamide, chloranthraniliprole (Rynaxypyr®), cyanthraniliprole (Cyazypyr®), or
  the phthalamide compounds
    M.26.1: (R)-3-Chlor-N1-{2-methyl-4-[1,2,2,2-tetrafluor-1-(trifluormethyl)ethyl]phenyl}-N2-(1-methylsulfonylethyl)phthalamid and
    M.26.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound
    M.26.3: 3-bromo-N-{2-bromo-4-chloro-6-[(1-cyclopropylethyl)carbamoyl]phenyl}-1-(3-chlorpyridin-2-yl)-1H-pyrazole-5-carboxamide, or the compound
    M.26.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate;

M.X insecticidal active compounds of unknown or uncertain mode of action, as for example azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, or the compound M.X.1: 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide, or the compound M.X.2: cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a, 12b-trimethyl-11-oxo-9-(3-pyridinyl)-2H, 11H-naphtho[2,1-b]pyrano[3,4-e]pyran-3,6-diyl]ester, or the compound M.X.3: 11-(4-chloro-2,6-dimethylphenyl)-12-hydroxy-1,4-dioxa-9-azadispiro[4.2.4.2]-tetradec-11-en-10-one, or the compound M.X.4: 3-(4'-fluoro-2,4-dimethylbiphenyl-3-yl)-4-hydroxy-8-oxa-1-azaspiro[4.5]dec-3-en-2-one, or the compound M.X.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *Bacillus firmus* (Votivo, 1-1582).

The commercially available compounds of the group M listed above may be found in The Pesticide Manual, 15th Edition, C. D. S. Tomlin, British Crop Protection Council (2011) among other publications.

The phthalamides M.26.1 and M.26.2 are both known from WO 2007/101540. The anthranilamide M.26.3 has been described in WO2005/077943. The hydrazide compound M.26.4 has been described in WO 2007/043677. The quinoline derivative flometoquin is shown in WO2006/013896. The aminofuranone compounds flupyradifurone is known from WO 2007/115644. The sulfoximine compound sulfoxaflor is known from WO2007/149134. The isoxazoline compound M.X.1 has been described in WO2005/085216. The pyripyropene derivative M.X.2 has been described in WO 2006/129714. The spiroketal-substituted cyclic ketoenol derivative M.X.3 is known from WO2006/089633 and the biphenyl-substituted spirocyclic ketoenol derivative M.X.4 from WO2008/067911. Finally triazoylphenylsulfide like M.X.5 have been described in WO2006/043635 and biological control agents on basis of *bacillus firmus* in WO2009/124707.

The following list F of active substances, in conjunction with which the compounds according to the invention can be used, is intended to illustrate the possible combinations but does not limit them:

F.I) Respiration Inhibitors

F.I-1) Inhibitors of complex III at Qo site:
  strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxyacrylic acid methyl ester and 2 (2-(3-(2,6-dichlorophenyl)-1-methyl-allylideneaminooxymethyl)-phenyl)-2-methoxyimino-N methyl-acetamide;
  oxazolidinediones and imidazolinones: famoxadone, fenamidone;

F.I-2) Inhibitors of complex II (e.g. carboxamides):
  carboxanilides: benodanil, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide, N-(4'-trifluoromethylthiobiphenyl-2-yl)-3 difluoromethyl-1-methyl-1H pyrazole-4-carboxamide, N-(2-(1,3,3-trimethyl-butyl)-phenyl)-1,3-dimethyl-5 fluoro-1H-pyrazole-4 carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide and 1,3,5-trimethyl-N-(1,1,3-trimethylindan-4-yl)pyrazole-4-carboxamide;

F.I-3) Inhibitors of complex III at Qi site: cyazofamid, amisulbrom, 3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

F.I-4) Other respiration inhibitors (complex I, uncouplers) diflumetorim; tecnazen; ferimzone; ametoctradin; silthiofam; nitrophenyl derivates: binapacryl, dinobuton, dinocap, fluazinam, nitrthal-isopropyl, organometal compounds: fentin salts, such as fentin-acetate, fentin chloride or fentin hydroxide;

F.II) Sterol biosynthesis inhibitors (SBI fungicides)

F.II-1) C14 demethylase inhibitors (DMI fungicides, e.g. triazoles, imidazoles)

triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole;

imidazoles: imazalil, pefurazoate, oxpoconazole, prochloraz, triflumizole;

pyrimidines, pyridines and piperazines: fenarimol, nuarimol, pyrifenox, triforine, 1-[rel-(2 S; 3R)-3-(2-chlorophenyl)-2-(2,4-difluorophenyl)-oxiranylmethyl]-5-thiocyanato-1 H-[1,2,4]triazole, 2-[rel-(2S; 3R)-3-(2-chlorophenyl)-2-(2,4-difluorophenyl)-oxiranylmethyl]-2H-[1,2,4]triazole-3-thiol;

F.II-2) Delta14-reductase inhitors (Amines, e.g. morpholines, piperidines)

morpholines: aldimorph, dodemorph, dodemorph-acetate, fenpropimorph, tridemorph; piperidines: fenpropidin, piperalin; spiroketalamines: spiroxamine;

F.II-3) Inhibitors of 3-keto reductase: hydroxyanilides: fenhexamid;

F.III) Nucleic acid synthesis inhibitors

F.III-1) RNA, DNA synthesis phenylamides or acyl amino acid fungicides: benalaxyl, benalaxyl-M, kiralaxyl, metalaxyl, metalaxyl-M (mefenoxam), ofurace, oxadixyl;

isoxazoles and iosothiazolones: hymexazole, octhilinone;

F.-2) DNA topisomerase inhibitors: oxolinic acid;

F.III-3) Nucleotide metabolism (e.g. adenosin-deaminase), hydroxy(2-amino)-pyrimidines: bupirimate;

F.IV) Inhibitors of cell division and or cytoskeleton

F.IV-1) Tubulin inhibitors: benzimidazoles and thiophanates: benomyl, carbendazim, fuberidazole, thiabendazole, thiophanate-methyl;

triazolopyrimidines: 5-chloro-7 (4-methylpiperidin-1-yl)-6-(2,4,6-trifluorophenyl)-[1,2,4]triazolo[1,5 a]pyrimidine;

F.IV-2) Other cell division inhibitors benzamides and phenyl acetamides: diethofencarb, ethaboxam, pencycuron, fluopicolide, zoxamide;

F.IV-3) Actin inhibitors: benzophenones: metrafenone;

F.V) Inhibitors of amino acid and protein synthesis

F.V-1) Methionine synthesis inhibitors (anilino-pyrimidines)

anilino-pyrimidines: cyprodinil, mepanipyrim, nitrapyrin, pyrimethanil;

F.V-2) Protein synthesis inhibitors (anilino-pyrimidines) antibiotics: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI-1) MAP/Histidine kinase inhibitors (e.g. anilino-pyrimidines)

dicarboximides: fluoroimid, iprodione, procymidone, vinclozolin;

phenylpyrroles: fenpiclonil, fludioxonil;

F.VI-2) G protein inhibitors: quinolines: quinoxyfen;

F.VII) Lipid and membrane synthesis inhibitors

F.VII-1) Phospholipid biosynthesis inhibitors organophosphorus compounds: edifenphos, iprobenfos, pyrazophos;

dithiolanes: isoprothiolane;

F.VII-2) Lipid peroxidation: aromatic hydrocarbons: dicloran, quintozene, tecnazene, tolclofos-methyl, biphenyl, chloroneb, etridiazole;

F.VII-3) Carboxyl acid amides (CAA fungicides)

cinnamic or mandelic acid amides: dimethomorph, flumorph, mandiproamid, pyrimorph;

valinamide carbamates: benthiavalicarb, iprovalicarb, pyribencarb, valifenalate and N-(1-(1-(4-cyano-phenyl)ethanesulfonyl)-but-2-yl) carbamic acid-(4-fluorophenyl) ester;

F.VII-4) Compounds affecting cell membrane permeability and fatty acids:

1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, carbamates: propamocarb, propamocarb-hydrochlorid, F.VIII) Inhibitors with Multi Site Action F.VIII-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles):

anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

F.VIII-4) Guanidines and other: guanidine, dodine, dodine free base, guazatine, guazatine-acetate, iminoctadine, iminoctadine-triacetate, iminoctadine-tris(albesilate), 2,6-dimethyl-1H,5H-[1,4]dithiino[2,3-c:5,6-c']dipyrrole-1,3,5,7 (2H,6H)-tetraone;

F.VIII-5) Ahtraquinones: dithianon;

F.IX) Cell wall synthesis inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant defence inducers

F.X-1) Salicylic acid pathway: acibenzolar-S-methyl;

F.X-2) Others: probenazole, isotianil, tiadinil, prohexadione-calcium;

phosphonates: fosetyl, fosetyl-aluminum, phosphorous acid and its salts;

F.XI) Unknown mode of action:bronopol, chinomethionat, cyflufenamid, cymoxanil, dazomet, debacarb, diclomezine, difenzoquat, difenzoquat-methylsulfate, diphenylamin, flumetover, flusulfamide, flutianil, methasulfocarb, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N'(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydro-pyrazole-1 carbothioic acid S-allyl ester, N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide.

F.XI) Growth regulators: abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6-benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XII) Biological control agents
antifungal biocontrol agents: *Bacillus substilis* strain with NRRL No. B-21661 (e.g. Rhapsody®, Serenade® MAX and Serenade® ASO from AgraQuest, Inc., USA.), *Bacillus pumilus* strain with NRRL No. B-30087 (e.g. Sonata® and Ballad® Plus from AgraQuest, Inc., USA), *Ulocladium oudemansii* (e.g. the product Botry-Zen from BotriZen Ltd., New Zealand), Chitosan (e.g. Armour-Zen from BotriZen Ltd., New Zealand).

Due to their activity, the compounds of the present invention may be used for controlling invertebrate pests.

The invertebrate pest (also referred to as "animal pest"), in particular the arthropod pest such as insects and arachnids, and nematodes, the plant, soil or water in which the plant is growing can be contacted with the present compounds of formula I or salts thereof or composition(s) comprising them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I, or their salts or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the invertebrate pests, in particular insects, or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

The present invention also includes a method of combating invertebrate pests which comprises contacting the invertebrate pests, their habitat, breeding ground, food supply, cultivated plants, seed, soil, area, material or environment in which the animal pests are growing or may grow, or the materials, plants, seeds, soils, surfaces or spaces to be protected from invertebrate pest attack or infestation with a pesticidally effective amount of a mixture of at least one active compound I or a salt thereof. Moreover, invertebrate pests may be controlled by contacting the target pest, its food supply, habitat, breeding ground or its locus with a pesticidally effective amount of compounds of formula I or a salt thereof. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by invertebrate pests by contacting the plant with a pesticidally effective amount of compounds of formula I. As such, "contacting" includes both direct contact (applying the compounds/compositions directly on the pest and/or plant —typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, the genetic material of which has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(s) (oligo- or polypeptides) for example by glycosylation or polymer additions such as prenylated, acetylated or farnesylated moieties or PEG moieties (e.g. as disclosed in Biotechnol Prog. 2001 July-August; 17(4):720-8, Protein Eng Des Sel. 2004 January; 17(1):57-66, Nat Protoc. 2007; 2(5): 1225-35, Curr Opin Chem Biol. 2006 October; 10(5): 487-91. Epub 2006 Aug. 28, Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e. g. EP-A-0242236, EP-A-242246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e. g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 und WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e. g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e. g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e. g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 1 g to 600 g per hectare, more desirably from 5 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitos, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of formula I as aerosols (e.g. in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds of formula I as well as their salts are also suitable for the treatment of seeds in order to protect the seed from insect pest, in particular from soil-living insect pests and the resulting plant's roots and shoots against soil pests and foliar insects.

The compounds of formula I as well as their salts are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected from piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment of seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing *Bacillus thuringiensis* toxins (Bt toxins) which make the plants resistant to certain pests (EP-A 142 924, EP-A 193 259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The compounds of formula I or the stereoisomers or veterinarily acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions comprising a parasiticidally effective amount of compounds of formula I or the stereoisomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the stereoisomers or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formula I or the stereoisomers or veterinarily acceptable salts thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or the stereoisomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the stereoisomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the stereoisomers or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus,* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Omithodorus hermsi, Omithodorus turicata* and parasitic mites (Mesostigmata), e.g. *Omithonyssus bacoti* and *Dermanyssus gallinae,*

Actinedida (Prostigmata) und Acaridida (Astigmata) e.g. *Acarapis* spp., *Cheyletiella* spp., *Omithocheyletia* spp., *Myobia* spp., Psorergates spp., *Demodex* spp., *Trombicula* spp., *Listrophorus* spp., *Acarus* spp., *Tyrophagus* spp., *Caloglyphus* spp., Hypodectes spp., *Pterolichus* spp., *Psoroptes* spp., Chorioptes spp., Otodectes spp., *Sarcoptes* spp., Notoedres spp., Knemidocoptes spp., Cytodites spp., and Laminosioptes spp, Bugs (Heteropterida): *Cimex lectularius, Cimex hemipterus, Reduvius senilis, Triatoma* spp., *Rhodnius ssp., Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and Nanocyetes spp, Cercomeromorpha, in particular Cestoda (Tapeworms), e.g. *Diphyllobothrium* spp., *Tenia* spp., *Echinococcus* spp., *Dipylidium* caninum, *Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin;

anionic surfactants, such as sodium lauryl sulfate, fatty alcohol ether sulfates, mono/dialkyl polyglycol ether orthophosphoric acid ester monoethanolamine salt;

cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 per cent by weight, preferably from 0.1 to 65 per cent by weight, more preferably from 1 to 50 per cent by weight, most preferably from 5 to 40 per cent by weight.

Preparations which are diluted before use contain the compounds acting against ectoparasites in concentrations of 0.5 to 90 per cent by weight, preferably of 1 to 50 per cent by weight.

Furthermore, the preparations comprise the compounds of formula I against endoparasites in concentrations of 10 ppm to 2 per cent by weight, preferably of 0.05 to 0.9 per cent by weight, very particularly preferably of 0.005 to 0.25 per cent by weight.

In a preferred embodiment of the present invention, the compositions comprising the compounds of formula I them are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

As pointed out above, a further aspect of the present invention relates to a crystalline form of 2-(3-chloro-2-pyridyl)-N-[2-methyl-4-chloro-6-[(diethyl-$\lambda^4$-sulfanylidene)carbamoyl]phenyl]-5-(trifluoromethyl)pyrazole-3-carboxamide. 2-(3-chloro-2-pyridyl)-N-[2-methyl-4-chloro-6-[(diethyl-$\lambda^4$-sulfanylidene)carbamoyl]phenyl]-5-(trifluoromethyl)pyrazole-3-carboxamide is a compound of formula Va, where both $R^1$ and $R^2$ are ethyl, $R^{3a}$ is methyl, $R^{3b}$ is chloro, $R^4$ is hydrogen, $R^5$ is trifluoromethyl, $R^6$ is chloro and Q is N. This compound is hereinafter also termed as compound Va-1. This compound has been described for the first time in WO 2007/006670. However, the procedure described therein only yield amorphous material, which is hereinafter termed as amorphous Va-1, while the herein described crystalline form of the compound Va-1 is termed form A of Va-1.

It was surprisingly found that reacting the compound of formula Ia, where both $R^1$ and $R^2$ are ethyl, $R^{3a}$ is methyl, $R^{3b}$ is chloro and $R^4$ is hydrogen, with 2-(3-chloro-2-pyridyl)-5-trifluoromethyl-3-carbonylchloride (compound of the formula VIa, where X=Cl, $R^5$=$CF_3$, Q=N and $R^6$=Cl) according to the process B yields the compound Va-1 in highly pure form, which allows for crystallization of the compound Va-1 from suitable aprotic organic solvents such as toluene, xylene, diethyl ether, diisopropyl ether, methyl tert-butyl ether or acetonitrile. Thereby the above described crystalline form A of the compound Va-1 can be obtained.

Form A of Va-1 is a stable crystalline form, which forms rhombic crystals and thus allows a much easier handling than amorphous Va-1. Form A of Va-1 is a stable crystalline anhydrate, which is essentially free from solvent in the crystal lattice. Form A of Va-1 has generally a purity with regard to the compound Va-1 of at least 95% by weight.

Referring to form A of Va-1, the term "essentially free from solvent" means that the inventive form A of Va-1 comprises no detectable amounts of solvents incorporated into the crystal lattice, i.e. the amount of solvent in the crystal lattice is less than 10 mol %, in particular not more than 5 mol %, based on the compound Va-1.

The inventive form A of Va-1 can be identified by means of X-ray powder diffractometry on the basis of its diffraction diagram. Thus, an X-ray powder diffractogram recorded at 25° C. using Cu—$K_\alpha$ radiation (1.54178 Å) shows at least 2, as a rule at least 4, frequently at least 5, in particular at least 7, especially at least 9 and specifically all of the 10 reflexes detailed in the table hereinbelow as 2θ values, or as interplanar spacings d:

X-Ray Powder Data of Form A of Va-1

| 2θ | d [Å] |
|---|---|
| 9.30 ± 0.2 | 9.50 ± 0.3 |
| 11.22 ± 0.2 | 7.88 ± 0.3 |
| 15.50 ± 0.2 | 5.72 ± 0.3 |
| 15.79 ± 0.2 | 5.61 ± 0.3 |
| 17.17 ± 0.2 | 5.17 ± 0.3 |
| 18.38 ± 0.2 | 4.83 ± 0.3 |
| 18.74 ± 0.2 | 4.74 ± 0.3 |
| 18.98 ± 0.2 | 4.68 ± 0.3 |
| 26.23 ± 0.2 | 3.49 ± 0.3 |
| 26.58 ± 0.2 | 3.35 ± 0.3 |

Besides X-ray powder diffractometry, differential scanning calorimetry (DSC) may also be employed for identifying form A of Va-1. Form A of Va-1 shows a thermogram with a characteristic melting peak in the range between 186 to 190° C. The peak maximum is typically in the range of approximately 188-189° C. The melting points indicated herein refer to data determined by means of differential scanning calorimetry (DSC, crucible material aluminum, heating rate 10 K/min).

Crystallization of form A of Va-1 can be achieved by conventional techniques such as evaporation crystallization or crystallization from a hot solution of Va-1 in a suitable aprotic organic solvent such as toluene, xylene or acetonitrile. For crystallization from hot solvent or evaporation crystallization, the compound Va-1 is dissolved in a suitable aprotic organic solvents such as toluene, xylene, diethyl ether, diisopropyl ether, methyl tert-butyl ether or acetonitrile. Crystallization can be effected by cooling. Alternatively, crystallization can be effected by removing solvent, e.g. by evaporation. Addition of seed crystals will help to achieve quantitative conversion of the compound Va-1 into its crystalline form. Preferably, crystallization is performed at temperatures in the range from −10 to 100° C., in particular from 0 to 50° C.

A further aspect of the present invention relates to a crystalline form I of 2-(3-chloro-2-pyridyl)-N-[2-methyl-4-chloro-6-[(bis-2-propyl-$\lambda^4$-sulfanylidene)carbamoyl]-phenyl]-5-(trifluoromethyl)pyrazole-3-carboxamide. 2-(3-Chloro-2-pyridyl)-N-[2-methyl-4-chloro-6-[(bis-2-propyl-$\lambda^4$-sulfanylidene)carbamoyl]phenyl]-5-(trifluoromethyl)-pyrazole-3-carboxamide is a compound of formula Va, where both $R^1$ and $R^2$ are 2-propyl, $R^{3a}$ is methyl, $R^{3b}$ is chloro, $R^4$ is hydrogen, $R^5$ is trifluoromethyl, $R^6$ is chloro and Q is N. This compound is hereinafter also termed as compound Va-2. This compound has also been described for the first time in WO 2007/006670. However, the procedure described therein only yield amorphous material, which is hereinafter termed as amorphous Va-2, while the herein described crystalline form I of the compound Va-2 is termed form I of Va-2.

It was surprisingly found that reacting the compound of formula Ia, where both $R^1$ and $R^2$ are 2-propyl, $R^{3a}$ is methyl, $R^{3b}$ is chloro and $R^4$ is hydrogen, with 2-(3-chloro-2-pyridyl)-5-trifluoromethyl-3-carbonylchloride (compound of the formula VIa, where X=Cl, $R^5$=$CF_3$, Q=N and $R^6$=Cl) according to the process B yields the compound Va-2 in highly pure form, which allows for crystallization of the compound Va-2 from suitable aprotic organic solvents such as toluene, xylene or acetonitrile. Thereby the above described crystalline form I of the compound Va-2 can be obtained.

Form I of Va-2 is a stable crystalline form, which forms crystals having irregular shape. The crystallinity of Va-2 allows a much easier handling than amorphous Va-2. Form I of Va-2 is a stable crystalline anhydrate, which is essentially free from solvent in the crystal lattice. Form I of Va-2 has generally a purity with regard to the compound Va-2 of at least 95% by weight.

Heating form I of Va-2 at temperatures in the range of 190 to 220° C. yields another crystalline form II of the compound Va-2.

Form II of Va-2 is a stable crystalline form, which forms crystals having the shape of needles The crystallinity of Va-2 allows a much easier handling than amorphous Va-2. Form II of Va-2 is a stable crystalline anhydrate, which is essentially free from solvent in the crystal lattice. Form II of Va-2 has generally a purity with regard to the compound Va-2 of at least 95% by weight.

Referring to forms I and II of Va-2, the term "essentially free from solvent" means that the inventive forms I and II of Va-2 comprise no detectable amounts of solvents incorporated into the crystal lattice, i.e. the amount of solvent in the crystal lattice is less than 10 mol %, in particular not more than 5 mol %, based on the compound Va-2.

The inventive forms I and II of Va-2 can be identified by means of X-ray powder diffractometry on the basis of its diffraction diagram. Thus, an X-ray powder diffractogram of form I, recorded at 25° C. using Cu—$K_\alpha$ radiation (1.54178 Å) shows at least 2, as a rule at least 4, frequently at least 5, in particular at least 7, especially at least 9 and specifically all of the reflexes detailed in the table hereinbelow as 2θ values, or as interplanar spacings d:

X-Ray Powder Data of Form I of Va-2

| 2θ | d [Å] |
|---|---|
| 8.64 ± 0.2 | 10.24 ± 0.3 |
| 10.05 ± 0.2 | 8.80 ± 0.3 |
| 10.23 ± 0.2 | 8.65 ± 0.3 |
| 13.09 ± 0.2 | 6.76 ± 0.3 |
| 13.48 ± 0.2 | 6.57 ± 0.3 |
| 15.11 ± 0.2 | 5.86 ± 0.3 |
| 15.89 ± 0.2 | 5.58 ± 0.3 |
| 16.42 ± 0.2 | 5.40 ± 0.3 |
| 17.67 ± 0.2 | 5.02 ± 0.3 |
| 18.35 ± 0.2 | 4.84 ± 0.3 |

An X-ray powder diffractogram of form II of Va-2, recorded at 25° C. using Cu—$K_\alpha$ radiation (1.54178 Å) shows at least 2, as a rule at least 4, frequently at least 5, in particular at least 7, especially at least 9 and specifically all of the reflexes detailed in the table hereinbelow as 2θ values, or as interplanar spacings d:

X-Ray Powder Data of Form II of Va-2

| 2θ | d [Å] |
|---|---|
| 8.96 ± 0.2 | 9.87 ± 0.3 |
| 9.23 ± 0.2 | 9.58 ± 0.3 |
| 10.37 ± 0.2 | 8.53 ± 0.3 |
| 12.41 ± 0.2 | 7.13 ± 0.3 |
| 13.36 ± 0.2 | 6.63 ± 0.3 |
| 13.67 ± 0.2 | 6.48 ± 0.3 |
| 16.00 ± 0.2 | 5.54 ± 0.3 |
| 17.90 ± 0.2 | 4.96 ± 0.3 |
| 18.22 ± 0.2 | 4.87 ± 0.3 |
| 20.84 ± 0.2 | 4.27 ± 0.3 |

Besides X-ray powder diffractometry, differential scanning calorimetry (DSC) may also be employed for identifying form I of Va-2. Form I of Va-2 shows a thermogram with a characteristic melting peak in the range between 165 and 170° C. The peak maximum is typically in the range of approximately 168° C. An exothermic peak at temperatures above the melting peak can be observed at higher temperatures indicating the formation of another crystalline form which shows a melting peak above 215° C. with a peak maximum of approximately 221° C. The melting melting peak above 215° C. with a peak maximum of approximately 221° C. is also observed in a thermogramm of form II of Va-2. The melting points indicated herein refer to data determined by means of differential scanning calorimetry (DSC, crucible material aluminum, heating rate 10 K/min).

Crystallization of form I of Va-2 can be achieved by conventional techniques such as evaporation crystallization or crystallization from a hot solution of Va-2 in a suitable aprotic organic solvent such as toluene, xylene or acetonitrile. For crystallization from hot solvent or evaporation crystallization, the compound Va-2 is dissolved in a suitable aprotic organic solvents such as toluene, xylene or acetonitrile. Crystallization can be effected by cooling. Alternatively, crystallization can be effected by removing solvent, e.g. by evaporation. Addition of seed crystals will help to achieve quantitative conversion of the compound Va-2 into its crystalline form. Preferably, crystallization is performed at temperatures in the range from −10 to 100° C., in particular from 0 to 50° C.

Heating form I of Va-2 to a temperature in the range of 190 to 220° C. leads to quantitative conversion into form II II of the compound Va-2.

Besides easier handling, form A of Va-1 as well as forms I and II of Va-2 have beneficial formulation properties, in particular in formulations, which contain solid active ingredients, such as aqueous and non-aqueous suspension concentrate formulations and powder or granule formulations.

The following figures and examples further illustrate the present invention:

FIG. 1: X-ray Powder Diffractogramm (XRPD) of crystalline form A of Va-1, obtained from the example 4b.

Figure 2:
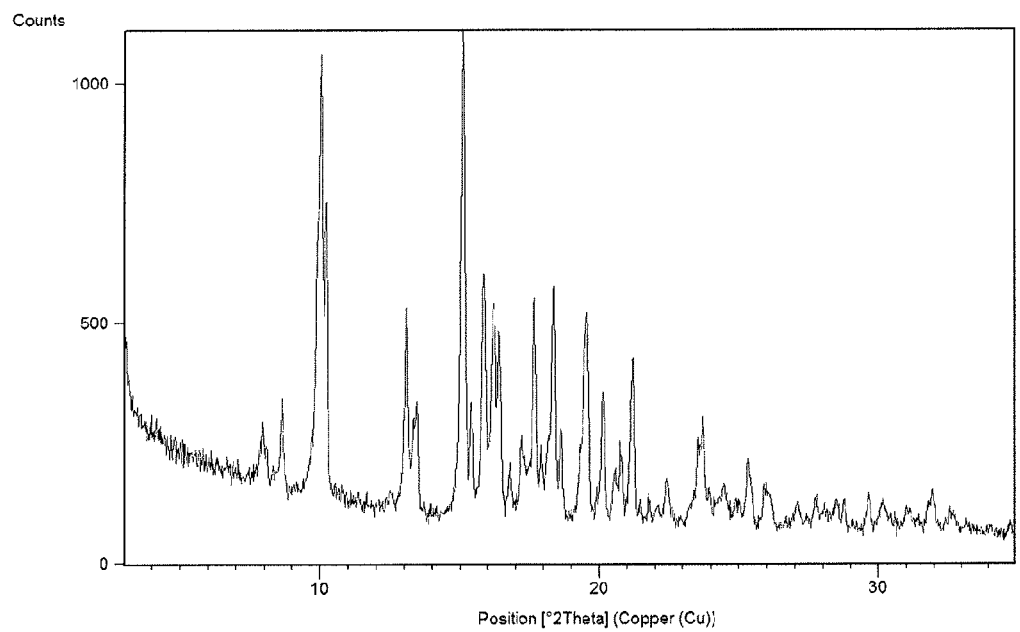

FIG. 2: X-ray Powder Diffractogramm (XRPD) of crystalline form I of Va-2, obtained from the example 5.

Figure 3:
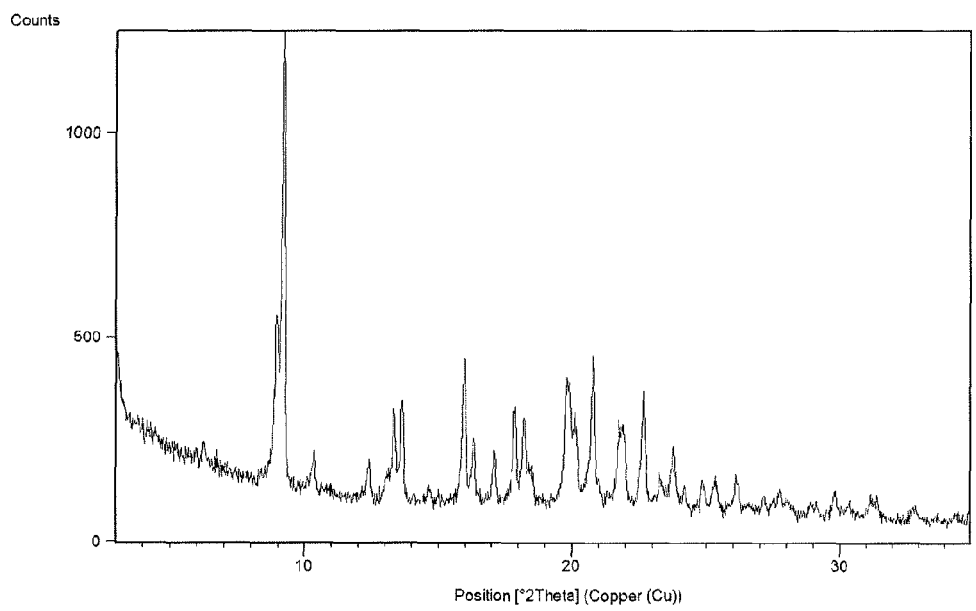

FIG. 3: X-ray Powder Diffractogramm (XRPD) of crystalline form I of Va-2, obtained by heating form I of Va-2 for 3 hours at 200° C.

EXAMPLES

The compounds can be characterized e.g. by coupled High Performance Liquid Chromatography/mass spectrometry (HPLC/MS), by $^1$H-NMR and/or by their melting points. The following analytical procedures were employed:

Method A: Analytical HPLC column: RP-18 column Chromolith Speed ROD from Merck KgaA (Germany). Elution: acetonitrile+0.1% trifluoroacetic acid (TFA)/water+0.1% trifluoroacetic acid (TFA) in a ratio of from 5:95 to 95:5 in 5 minutes at 40° C.

Method B: Analytical UPLC column: Phenomenex Kinetex 1.7 μm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0.8-1.0 mL/min in 1.50 minutes at 60° C.

MS-method: ESI positive.

$^1$H-NMR. The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singulett.

log P determinations were performed via capillary electrophorese on a cePro9600™ from CombiSep.

The X-ray powder diffractograms (XRPD) reported herein and displayed in FIGS. 1, 2 and 3 were recorded using a Panalytical X'Pert Pro diffractometer (manufacturer: Panalytical) in reflection geometry in the range from 2θ=3°-35° C. with increments of 0.0167° C. using Cu—Kα radiation (at 25° C.). The recorded 2θ values were used to calculate the stated interplanar spacings d. The intensity of the peaks (y-axis: linear intensity counts) is plotted versus the 2θ angle (x-axis in degrees 2θ).

DSC was performed on a Mettler Toledo DSC 822e module. Tha samples were placed in crimped but vented aluminium pans. The samples size in each case was 5 to 10 mg. The thermal behaviour was analized in the range 30-300° C. The heating rate was 10° C./min. The samples were purged with a stream of nitrogen flowing at 150 ml/during the experiment. Melting points values were confirmed by a Mettler Hot Stage in combination with a light microscope.

Preparation Examples

Starting Materials 6,8-dichloro-1H-benzo[d][1,3]oxazine-2,4-dione and 6-chloro-8-methyl-1H-3,1-benzoxazine-2,4-dione were prepared according to WO 2007/43677.

S,S-Diisopropyl-S-aminosulfonium 2,4,6-trimethylphenylsulfonat was prepared according to Y. Tamura et al, Tetrahedron 1975, 31, 3035-3040.

2-(3-Chloropyridin-2-yl)-5-bromo-2H-pyrazole-3-carbonyl chloride was prepared according to WO 2007/24833.

Preparation Examples P.1 to P.7

Example P.1

S,S-Dimethyl sulfinium sulfate (Compound IV-1 with $R^1=R^2$=methyl, $A^-=\frac{1}{2}SO_4^{2-}$)

To a solution of sodium methylate (15.76 g of a 30% solution in methanol, 87.54 mmol, 1.100 equiv.) in methanol (60 mL) was added dimethyl sulphide (5.44 g, 6.40 mL, 87.6 mmol, 1.10 equiv.) at −5-0° C. To this mixture was added a pre-cooled solution (−20° C.) of hydroxylamine-O-sulfonic acid (9.00 g, 79.6 mmol) in methanol (60 mL) and the internal temperature was maintained at −5-0° C. After stirring at room temperature overnight, all solids were removed by filtration. The filtrate was concentrated in vacuo and the residue was triturated with acetonitrile (50 mL) to yield the title compound (7.88 g, 39%).

The following compounds were prepared by analogy to example P.1:

S,S-diethyl sulfinium sulfate (Compound IV-1 with $R^1=R^2$=ethyl, $A^-=\frac{1}{2}SO_4^{2-}$), S-ethyl-S-isopropyl sulfinium sulfate (Compound IV-1 with $R^1$=ethyl, $R^2$=isopropyl, $A^-=\frac{1}{2}SO_4^{2-}$), S,S-diisopropyl sulfinium sulfate (Compound IV-1 with $R^1=R^2$=2-propyl, $A^-=\frac{1}{2}SO_4^{2-}$), tetrahydro-$\lambda^4$-thiophen-1-ylamin mesitylsulfonate (Compound IV-1 with $R^1$—$R^2$=1,4-butandiyl, $A^-$=2,4,6-trimethylphenylsulfonate) was prepared according to Y. Tamura et al, Tetrahedron, 1975, 31, 3035-3040, tetrahydro-$\lambda^4$-thiophen-1-ylamin sulfate (Compound IV-1 with $R^1$—$R^2$=1,4-butandiyl, $A^-=\frac{1}{2}SO_4^{2-}$), $\lambda^4$-1,3-dithiolan-1-ylamin sulfate (Compound IV-1 with $R^1$—$R^2$=2-thiabutan-1,4-diyl, $A^-=\frac{1}{2}SO_4^{2-}$), $\lambda^4$-thian-1-ylamin sulfate (Compound IV-1 with $R^1$—$R^2$=pentan-1,5-diyl, $A^-=\frac{1}{2}SO_4^{2-}$), S,S-bis(cyclopropylmethyl) sulfinium sulfate (Compound IV-1 with $R^1=R^2$=cyclopropylmethyl, $A^-$=½$SO_4^{2-}$),
S,S-bis(2-cyclopropylethyl) sulfinium sulfate (Compound IV-1 with $R^1=R^2$=2-cyclopropylethyl, $A^-$=½$SO_4^{2-}$),
S,S-bis(cyclobutylmethyl) sulfinium sulfate (Compound IV-1 with $R^1=R^2$=cyclobutylmethyl, $A^-$=½$SO_4^{2-}$),
S,S-bis(cyclopentylmethyl) sulfinium sulfate (Compound IV-1 with $R^1=R^2$=cyclopentylmethyl, $A^-$=½$SO_4^{2-}$),
S-cyclopropylmethyl-S-ethyl sulfinium sulfate (Compound IV-1 with $R^1$=ethyl, $R^2$=cyclopropylmethyl, $A^-$=½$SO_4^{2-}$),
S-(2-cyclopropylethyl)-S-ethyl sulfinium sulfate (Compound IV-1 with $R^1$=ethyl, $R^2$=2-cyclopropylethyl, $A^-$=½$SO_4^{2-}$),
S-(2-cyclopropylethyl)-S-isopropyl sulfinium sulfate (Compound IV-1 with $R^1$=2-propyl, $R^2$=2-cyclopropylethyl, $A^-$=½$SO_4^{2-}$),
S-(1-cyclopropylethyl)-S-isopropyl sulfinium sulfate (Compound IV-1 with $R^1$=2-propyl, $R^2$=1-cyclopropylethyl, $A^-$=½$SO_4^{2-}$),
S-cyclobutylmethyl-S-ethyl sulfinium sulfate (Compound IV-1 with $R^1$=ethyl, $R^2$=cyclobutylmethyl, $A^-$=½$SO_4^{2-}$),
S-cyclopentylmethyl-S-ethyl sulfinium sulfate (Compound IV-1 with $R^1$=ethyl, $R^2$=cyclopentylmethyl, $A^-$=½$SO_4^{2-}$),
S-cyclopropylmethyl-S-isopropyl sulfinium sulfate (Compound IV-1 with $R^1$=2-propyl, $R^2$=cyclopropylmethyl, $A^-$=½$SO_4^{2-}$),
S-cyclobutylmethyl-S-isopropyl sulfinium sulfate (Compound IV-1 with $R^1$=2-propyl, $R^2$=cyclobutylmethyl, $A^-$=½$SO_4^{2-}$),
S-cyclopentylmethyl-S-isopropyl sulfinium sulfate (Compound IV-1 with $R^1$=2-propyl, $R^2$=cyclopentylmethyl, $A^-$=½$SO_4^{2-}$),
S,S-di-n-propyl sulfinium sulfate (Compound IV-1 with $R^1=R^2$=n-propyl, $A^-$=½$SO_4^{2-}$),
S-vinyl-S-ethyl sulfinium sulfate (Compound IV-1 with $R^1$=ethyl, $R^2$=vinyl, $A^-$=½$SO_4^{2-}$),
S,S-di-n-butyl sulfinium sulfate (Compound IV-1 with $R^1=R^2$=n-butyl, $A^-$=½$SO_4^{2-}$),
S,S-di-n-pentyl sulfinium sulfate (Compound IV-1 with $R^1=R^2$=n-pentyl, $A^-$=½$SO_4^{2-}$),
S,S-di-n-hexyl sulfinium sulfate (Compound IV-1 with $R^1=R^2$=n-hexyl, $A^-$=½$SO_4^{2-}$),
S,S-bis(2-ethylhexyl) sulfinium sulfate (Compound IV-1 with $R^1=R^2$=2-ethylhexyl, $A^-$=½$SO_4^{2-}$),
S,S-bis(3-methyl-2-butyl) sulfinium sulfate (Compound IV-1 with $R^1=R^2$=3-methyl-2-butyl, $A^-$=½$SO_4^{2-}$),
S,S-bis(3-methyl-1-butyl) sulfinium sulfate (Compound IV-1 with $R^1=R^2$=3-methyl-1-butyl, $A^-$=½$SO_4^{2-}$),
S,S-bis(2-methylpropyl) sulfinium sulfate (Compound IV-1 with $R^1=R^2$=2-methylpropyl, $A^-$=½$SO_4^{2-}$),
S-isopropyl-S-methyl sulfinium sulfate (Compound IV-1 with $R^1$=methyl, $R^2$=isopropyl $A^-$=½$SO_4^{2-}$),
S-2-butyl-S-methyl sulfinium sulfate (Compound IV-1 with $R^1$=methyl, $R^2$=2-butyl, $A^-$=½$SO_4^{2-}$),
S-3-Methyl-2-butyl-S-methyl sulfinium sulfate (Compound IV-1 with $R^1$=methyl, $R^2$=3-Methyl-2-butyl $A^-$=½$SO_4^{2-}$),
S-3-Methyl-2-butyl-S-ethyl sulfinium sulfate (Compound IV-1 with $R^1$=ethyl, $R^2$=3-Methyl-2-butyl $A^-$=½$SO_4^{2-}$),
S-3-Methyl-2-butyl-S-isopropyl sulfinium sulfate (Compound IV-1 with $R^1$=2-propyl, $R^2$=3-Methyl-2-butyl $A^-$=½$SO_4^{2-}$),
S,S-bis(2-hydroxyethyl) sulfinium sulfate (Compound IV-1 with $R^1=R^2$=2-hydroxyethyl, $A^-$=½$SO_4^{2-}$),
S-(4-Fluorophenyl)-S-methyl sulfinium sulfate (Compound IV-1 with $R^1$=methyl, $R^2$=4-fluorophenyl, $A^-$=½$SO_4^{2-}$),
S-n-pentyl-S-2-hydroxyethyl sulfinium sulfate (Compound IV-1 with $R^1$=n-pentyl, $R^2$=2-hydroxyethyl, $A^-$=½$SO_4^{2-}$),
S-ethyl-S-cyclopropyl sulfinium sulfate (Compound IV-1 with $R^1$=ethyl, $R^2$=cyclopropyl, $A^-$=½$SO_4^{2-}$),
S-2-propyl-S-cyclopropyl sulfinium sulfate (Compound IV-1 with $R^1$=2-propyl, $R^2$=cyclopropyl, $A^-$=½$SO_4^{2-}$),
S-methyl-S-ethyl sulfinium sulfate (Compound IV-1 with $R^1$=methyl, $R^2$=ethyl, $A^-$=½$SO_4^{2-}$),
S-methyl-S-n-propyl sulfinium sulfate (Compound IV-1 with $R^1$=methyl, $R^2$=n-propyl, $A^-$=½$SO_4^{2-}$),
S-(2-chloroethyl)-S-ethyl sulfinium sulfate (Compound IV-1 with $R^1$=2-chloroethyl, $R^2$=ethyl, $A^-$=½$SO_4^{2-}$).

Example P.2

8-Bromo-6-chloro-1H-benzo[d][1,3]oxazine-2,4-dione

To a solution of 2-amino-3-bromo-5-chlorobenzoic acid (10.0 g, 39.9 mmol) in dioxane (170 mL) was added phosgene (20% in toluene, 42.0 mL, 79.9 mmol) over a period of 15 mins. The reaction was stirred at ambient temperature for 48 h and then concentrated in vacuo. The resulting solid was crushed and further dried in vacuo to yield the desired product (12.6 g, 114%) which was used in the subsequent step without further purification.

The following compounds were prepared by analogy to example P.2:
6,8-dichloro-1H-benzo[d][1,3]oxazine-2,4-dione,
6,8-dibromo-1H-benzo[d][1,3]oxazine-2,4-dione,
6-Bromo-8-chloro-1H-benzo[d][1,3]oxazine-2,4-dione,
8-Bromo-6-chloro-1H-benzo[d][1,3]oxazine-2,4-dione,
6-chloro-8-methyl-1H-benzo[d][1,3]oxazine-2,4-dione,
6-bromo-8-methyl-1H-benzo[d][1,3]oxazine-2,4-dione,
6-cyano-8-methyl-1H-benzo[d][1,3]oxazine-2,4-dione,
6-chloro-8-trifluoromethyl-1H-benzo[d][1,3]oxazine-2,4-dione,
8-chloro-6-trifluoromethyl-1H-benzo[d][1,3]oxazine-2,4-dione,
6-bromo-8-trifluoromethyl-1H-benzo[d][1,3]oxazine-2,4-dione,
8-bromo-6-trifluoromethyl-1H-benzo[d][1,3]oxazine-2,4-dione,
8-chloro-6-cyano-1H-benzo[d][1,3]oxazine-2,4-dione,
6-chloro-8-methoxy-1H-benzo[d][1,3]oxazine-2,4-dione,
6-chloro-8-cyclopropyl-1H-benzo[d][1,3]oxazine-2,4-dione,
6-chloro-8-ethyl-1H-benzo[d][1,3]oxazine-2,4-dione,
6-difluoromethoxy-8-methyl-1H-benzo[d][1,3]oxazine-2,4-dione,
6-cyano-8-methoxy-1H-benzo[d][1,3]oxazine-2,4-dione,
6-fluoro-8-methyl-1H-benzo[d][1,3]oxazine-2,4-dione,
6-iodo-8-methyl-1H-benzo[d][1,3]oxazine-2,4-dione,
6-nitro-8-methyl-1H-benzo[d][1,3]oxazine-2,4-dione,
6-(5-chloro-2-thienyl)-8-methyl-1H-benzo[d][1,3]oxazine-2,4-dione,
6-(3-pyrazol-1H-yl)-8-methyl-1H-benzo[d][1,3]oxazine-2,4-dione,
6-(3-isoxazolyl)-8-methyl-1H-benzo[d][1,3]oxazine-2,4-dione,
6-(hydroxyiminomethyl)-8-methyl-1H-benzo[d][1,3]oxazine-2,4-dione,
6-(methoxyiminomethyl)-8-methyl-1H-benzo[d][1,3]oxazine-2,4-dione,
6-(dimethylhydrazonomethyl)-8-methyl-1H-benzo[d][1,3]oxazine-2,4-dione and 6-(2,2,2-trifluoroethylhydrazonomethyl)-8-methyl-1H-benzo[d][1,3]oxazine-2,4-dione.

Example P.3

1-(3-chloro-2-pyridyl)-3-trifluoromethyl-1H-pyrazol a) 2.71 kg of 1,1,1-trifluoro-4-methoxy-but-3-en-2-on, 2.44 kg of ethanol and 3.10 kg of water were charged into a reaction vessel. 20 ml of concentrated hydrochloric acid and 0.80 kg of hydrazine hydrate were successively added and the mixture was heated to reflux for 4 h. The mixtures was allowed to cool and neutralized by addition of 10% aqueous NaOH to about pH 4-5. Then the mixture was evaporated. Toluene was added and the mixture was again evaporated to yield 2 kg of raw 3-trifluoromethyl-pyrazole with a purity of >85%.

b) 1.72 kg (10.75 mol) of the raw 3-trifluoromethylpyrazole obtained in step a), 1.75 kg (11.83 mol) of 2,3-dichloropyridine and 4.73 kg of dimethyl formamide were charged to a reaction vessel. 2.97 kg (21.50 mol) of potassium carbonate were added, the mixture was heated to 120° C. with stirring and kept at 120-125° C. for further 3 h. The reaction mixtures was cooled to 25° C. and poured into 20 l of water. The thus obtained mixture was extracted twice with 5 L of tert.-butyl-methyl ether. The combined organic phases were washed with 4 l of water and then evaporated to dryness.

Toluene was added and the mixture was again evaporated to dryness. Thereby, the 2.7 kg of the title compound was obtained (purity>75% as determined by GC; yield 81.5%). The product can be purified by distillation.

$^1$H-NMR (400 MHz, CDCl$_3$): δ [delta]=6.73 (d, 1H), 7.38 (d, 1H), 7.95 (m, 1H), 8.14 (m, 1H), 8.46 (m, 1H).

Preparation of the Compounds of Formula (VI) (Examples P.4 to P.7)

Example P.4

2-(3-Chloropyridin-2-yl)-5-trifluoromethyl-2H-pyrazole-3-carbonyl chloride

In a reaction vessel equipped with a thermometer, septum, nitrogen inlet and stirring bar, 500 mg (2.02 mmol) of 1-(3-chloro-2-pyridyl)-3-trifloromethyl-1H-pyrazole were dissolved in 3 ml of dry tetrahydrofuran. By means of a syringe, 2.0 ml of a 2 M solution of isopropyl magnesium chloride in tetrahydrofuran were added dropwise with stirring, while cooling the vessel with an ice bath and keeping the internal temperature at about 20° C. The ice bath was removed and the mixture was stirred for further 20 minutes at 23° C. Then the mixture was cooled again to −5° C. and 4.25 ml of a 20% (w/w) solution of phosgene in toluene were added dropwise with stirring. The mixture was allowed to war at 23° C. and stirred for further 1 h at 23° C. The thus obtained reaction mixture was evaporated to dryness, redissolved in toluene and stirred for further 30 min. at 50° C. Solids were removed by filtration and washed with toluene. The combined filtrates were evaporated to dryness to yield 0.53 g of the title compound with a purity>85% (yield 84.6%).

Characterization by $^1$H-NMR (400 MHz, CDCl$_3$): δ [delta]= 7.43-7.54 (m, 2H), 7.93 (d, 1H), 8.52 (m, 1H).

Example P.5

2-(3-Chloropyridin-2-yl)-5-methoxy-2H-pyrazole-3-carbonyl chloride

In a reaction vessel equipped with a thermometer, septum, nitrogen inlet and stirring bar 1-(3-chloro-2-pyridyl)-3-triflo- romethyl-1H-pyrazole (2.0 g, 0.01 mol) were dissolved in dry 1,2-dimethoxyethane (15 mL) and cooled to 0° C. By means of a syringe isopropyl magnesium chloride (11.4 mL of a 2 M solution in tetrahydrofuran) was added dropwise with stirring, while cooling the vessel with an ice bath and keeping the internal temperature below 5° C. After 3 h at this temperature a 20% (w/w) solution of phosgene in toluene (17 mL) were added dropwise with stirring. The mixture was allowed to warm to 23° C. and stirred for further 1 h at room temperature. The thus obtained reaction mixture was evaporated to dryness, redissolved in toluene and stirred for further 30 min. at 50° C. Solids were removed by filtration and washed with toluene. The combined filtrates were evaporated to dryness to yield 0.63 g of the title compound which was used in the next step without further purification.

Characterization of the corresponding hydrolysis product (carboxylic acid) by UPLC-MS: 1.170 min, M=218

Example P.6

2-(3-Chloropyridin-2-yl)-5-trifluoromethyl-2H-pyrazole-3-carbonyl chloride

In a reaction vessel equipped with a thermometer, septum, nitrogen inlet and stirring bar 1-(3-chloro-2-pyridyl)-3-methoxy-1H-pyrazole (2.00 g, 8.08 mmol) were dissolved in dry tetrahydrofuran (15 mL) and cooled to 0° C. By means of a syringe isopropyl magnesium chloride (8.1 mL of a 2 M solution in tetrahydrofuran, 16 mmol, 2.0 equiv.) was added dropwise with stirring, while cooling the vessel with an ice bath and keeping the internal temperature below 5° C. After 3 h at this temperature, the reaction mixture was dropwise transferred to a pre-cooled solution of a 20% (w/w) solution of phosgene in toluene (13 mL) while keeping the temperature below 0-5° C. After 15 min, the ice-bath was removed and the thus obtained reaction mixture was evaporated to dryness, redissolved in dichloromethane and stirred for further 5 min. Solids were removed by filtration and washed with dichloromethane. The combined filtrates were evaporated to dryness to yield the title compound (2.66 g, 106%) which was used in the next step without further purification.

$^1$H-NMR (400 MHz, CDCl$_3$): δ[delta]=7.43-7.54 (m, 2H), 7.93 (d, 1H), 8.52 (m, 1H).

Example P.7

2-(3-Chloropyridin-2-yl)-5-trifluoromethyl-2H-pyrazole-3-carbonyl chloride

In a reaction vessel equipped with a thermometer, septum, nitrogen inlet and stirring bar 1-(3-chloro-2-pyridyl)-3-methoxy-1H-pyrazole (2.00 g, 8.08 mmol) were dissolved in dry tetrahydrofuran (15 mL) and cooled to 0° C. By means of a syringe isopropyl magnesium chloride complex with lithium chloride (12.4 mL of a 1.3 M solution in tetrahydrofuran, 16 mmol, 2.0 equiv.) was added dropwise with stirring, while cooling the vessel with an ice bath and keeping the internal temperature below 20° C. After 1 h at this temperature, the reaction mixture was dropwise transferred to a pre-cooled solution of a 20% (w/w) solution of phosgene in toluene (13 mL) while keeping the temperature below 5° C. After 2 min, the ice-bath was removed and the thus obtained reaction mixture was evaporated to dryness, redissolved in dichloromethane and stirred for further 5 min. Solids were removed by filtration and washed with dichloromethane. The combined filtrates were evaporated to dryness to yield the title compound (1.75 g, 70%) which was used in the next step without further purification. $^1$H-NMR (400 MHz, CDCl$_3$): δ[delta]=7.43-7.54 (m, 2H), 7.93 (d, 1H), 8.52 (m, 1H).

Preparation Examples

Preparation of the Compounds of Formula I
(Examples S.1 to S.158)

Example S.1

2-amino-5-chloro-N-(dimethyl-λ$^4$-sulfanylidene)-3-methyl-benzamide

To a solution of 6-chloro-8-methyl-1H-3,1-benzoxazine-2,4-dione (3.00 g, 12.8 mmol) in dichloromethane (40 mL) was added dimethyl sulfinium sulfate (2.25 g, 8.93 mmol, 0.70 equiv.) and potassium tert-butylate (1.58 g, 14.0 mmol, 1.10 equiv.) at room temperature. The mixture was stirred for 1.5 h, upon which water was added and the layers were separated. The aqueous layer was extracted with dichloromethane, combined organic layers were dried over sodium sulphate and concentrated in vacuo. The residue was purified by flash-chromatography on silica gel to yield the title compound (2.63 g, 84%).

Characterization by HPLC-MS: 1.855 min, M=245.00.

Example S.2a 2-amino-5-chloro-N-(bis-2-methylpropyl-λ$^4$-sulfanylidene)-3-methyl-benzamide To a solution of 6-chloro-8-methyl-1H-3,1-benzoxazine-2,4-dione (3.00 g, 12.8 mmol) in dichloromethane (40 mL) was added bis-2-methylpropyl sulfinium sulfate (3.76 g, 8.93 mmol, 0.70 equiv.) and potassium tert-butylate (1.58 g, 14.0 mmol, 1.10 equiv.) at room temperature. The mixture was stirred for 1.5 h, upon which water was added and the layers were separated. The aqueous layer was extracted with dichloromethane, combined organic layers were dried over sodium sulphate and concentrated in vacuo. The residue was purified by flash-chromatography on silica gel to yield the title compound (2.89 g, 69%).

Characterization by $^1$H-NMR (400 MHz, DMSO-d$_6$): δ[delta]=1.04 (m, 12 H), 2.06 (s, 3H), 2.96 (m, 2H), 3.01 (m, 2H), 6.62 (br. s, 2H), 7.03 (s, 1H), 7.72 (s, 1H).

Example S.2b 2-amino-5-chloro-N-(bis-2-methylpropyl-λ$^4$-sulfanylidene)-3-methyl-benzamide To a solution of 6-chloro-8-methyl-1H-3,1-benzoxazine-2,4-dione (12.17 g, 0.06 mol) in anhydrous DMSO (100 mL) was added bis-2-methylpropyl sulfinium sulfate (14.56 g, 0.04 mol, 0.70 equiv.) and triethyl amine (9.19 mL, 6.67 g, 0.07 mol, 1.15 equiv.) at room temperature. The mixture was stirred for 4.5 h, and then added dropwise to ice-water. The mixture was extracted with dichloromethane and the combined organic layers were dried over sodium sulphate and concentrated in vacuo. The residue was triturated with ether to yield the title compound (8.3 g, 46%).

Characterization by $^1$H-NMR (400 MHz, DMSO-d$_6$): δ[delta]=1.04 (m, 12 H), 2.06 (s, 3H), 2.96 (m, 2H), 3.01 (m, 2H), 6.62 (br. s, 2H), 7.03 (s, 1H), 7.72 (s, 1H).

Example S.3

2-amino-5-chloro-N-(diethyl-λ$^4$-sulfanylidene)-3-methyl-benzamide

To a solution of 6-chloro-8-methyl-1H-3,1-benzoxazine-2,4-dione (2 g, 0.01 mol) in anhydrous propylene carbonate (30 mL) was added bis-2-ethyl sulfinium sulfate (2.04 g, 0.01 mol, 0.70 equiv.) and triethyl amine (1.38 mL, 1.0 g, 0.01 mol, 1.05 equiv.) at room temperature. The mixture was stirred for 4.5 h, and then added dropwise to ice-water. The mixture was extracted with dichloromethane and the combined organic layers were dried over sodium sulphate and concentrated in vacuo. The residue was triturated with ether to yield the title compound (1.43 g, 55%).

Characterization by $^1$H-NMR (400 MHz, CDCl$_3$): δ[delta]=1.39 (t, 6H), 2.13 (s, 3H), 3.02 (q, 4H), 5.95 (br. S, 2H), 7.01 (s, 1H), 7.98 (s, 1H).

Example S.4

2-amino-3,5-dichloro-N-(bis-2-methylpropyl-λ$^4$-sulfanylidene)-benzamide

The title compound was prepared by analogy to the method of example S.3
Yield: 60%
Characterization by $^1$H-NMR (400 MHz, DMSO-d$_6$): δ[delta]=1.23 (d, 6H), 1.38 (d, 6H), 3.42 (m, 2H), 7.02 (br. s, 2H), 7.41 (s, 1H), 7.95 (s, 1H).

By the methods described in examples S.1 to S.4 the compounds of formula Ia with $R^4$=H, summarized in the following table C.1 were prepared:

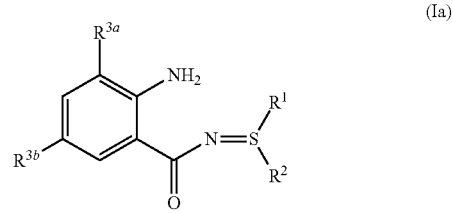
(Ia)

TABLE C.1

| compounds of formula Ia with $R^4$ = H | | | | | |
|---|---|---|---|---|---|
| Cpd. | $R^1$ | $R^2$ | $R^{3a}$ | $R^{3b}$ | HPLC/MS (Method) |
| S.3 | C$_2$H$_5$ | C$_2$H$_5$ | CH$_3$ | Cl | 2.159 min, m/z = 273.0 (A) |
| S.4 | CH$_2$CH(CH$_3$)$_2$ | CH$_2$CH(CH$_3$)$_2$ | Cl | Cl | |
| S.5 | CH(CH$_3$)$_2$ | CH(CH$_3$)$_2$ | Cl | Cl | 3.346 min, m/z = 321.05 (A) |
| S.6 | C$_2$H$_5$ | C$_2$H$_5$ | Cl | Cl | 2.821 min, m/z = 292.9 (A) |
| S.7 | CH$_2$—c-Pr | CH$_2$—c-Pr | CH$_3$ | Cl | 1.191 min, m/z = 325.5 (B) |
| S.8 | CH$_2$—c-Pr | CH$_2$—c-Pr | Cl | Cl | 1.391 min, m/z = 320.8 (B) |
| S.9 | CH$_2$—c-Pr | C$_2$H$_5$ | CH$_3$ | Cl | 1.197 min, m/z = 299.1 (B) |

TABLE C.1-continued compounds of formula Ia with $R^4 = H$

| Cpd. | $R^1$ | $R^2$ | $R^{3a}$ | $R^{3b}$ | HPLC/ MS (Method) |
|---|---|---|---|---|---|
| S.10 | $CH_2$—c-Pr | $CH(CH_3)_2$ | Cl | Cl | 3.200 min, m/z = 333.0 (A) |
| S.11 | $CH_2$—c-Pr | $CH(CH_3)_2$ | $CH_3$ | Cl | 2.433 min, m/z = 313.0 (A) |
| S.12 | $C_2H_5$ | $C_2H_5$ | $CF_3$ | Cl | 3.218 min, m/z = 327.00 (A) |
| S.13 | $C_2H_5$ | $C_2H_5$ | $CF_3$ | Br | 3.291 min, m/z = 372.90 (A) |
| S.14 | $C_2H_5$ | $C_2H_5$ | Br | Cl | 2.980 min, m/z = 338.90 (A) |
| S.15 | $C_2H_5$ | $C_2H_5$ | Cl | Br | 2.970 min, m/z = 338.90 (A) |
| S.16 | $CH(CH_3)_2$ | $CH(CH_3)_2$ | $CF_3$ | Cl | 3.604 min, m/z = 355.05 (A) |
| S.17 | $CH(CH_3)_2$ | $CH(CH_3)_2$ | $CF_3$ | Br | 3.677 min, m/z = 400.95 (A) |
| S.18 | $CH(CH_3)_2$ | $CH(CH_3)_2$ | Br | Cl | 3.390 min, m/z = 366.95 (A) |
| S.19 | $CH(CH_3)_2$ | $CH(CH_3)_2$ | Cl | Br | 3.381 min, m/z = 366.95 (A) |
| S.20 | $CH(CH_3)_2$ | $CH(CH_3)_2$ | Br | Br | 3.409 min, m/z = 410.90 (A) |
| S.21 | $CH_2CH_2CH_3$ | $CH_2CH_2CH_3$ | $CH_3$ | Cl | 1.046 min, m/z = 301.1 (B) |
| S.22 | $CH_2CH_2CH_3$ | $CH_2CH_2CH_3$ | Cl | Cl | 3.441 min, m/z = 320.95 (A) |
| S.23 | $C_2H_5$ | $C_2H_5$ | Br | Br | 1.102 min, m/z = 383.0 (B) |
| S.24 | $CH(CH_3)_2$ | $CH(CH_3)_2$ | $CH_3$ | Cl | 2.510 min, m/z = 301.05 (A) |

$CH_2$—c-Pr = $CH_2$-cyclopropyl

By the methods described in examples S.1 to S.3 the compounds S.24 to S.158 of formula Ia with $R^4$=H, summarized in the following table C.2, can be prepared.
In table C.2 the following abbreviations are used:
mp: melting point
$R^{3b}$-1: CH(=N—OCH$_3$)
$R^{3b}$-2: 3-pyrazol-1H-yl
$R^{3b}$-3: CH(=N—NHCH$_2$CF$_3$)
$R^{3b}$-4: CH[=N—N(CH$_3$)$_2$]
Me: Methyl
OMe: Methoxy
Et: Ethyl
i-Pr: isopropyl
i-Bu: isobutyl
3-Me-2-Bu: 3-methyl-2-butyl
3-Me-1-Bu: 3-methyl-1-butyl
n-Bu: n-butyl
2-Bu: 2-butyl
n-Pe: n-pentyl
n-Hex: n-hexyl
2-EtHex: 2-ethylhexyl
c-Pr: cyclopropyl
c-Bu: cyclobutyl
c-Pe: cyclopentyl
2-Cl-5-Tp: 2-chloro-5-thiophenyl
4-F-Ph: 4-fluorophenyl

TABLE C.2 compounds of formula Ia with $R^4 = H$ (compounds S.25 to S.158)

| # | $R^1$ | $R^2$ | $R^{3a}$ | $R^{3b}$ |
|---|---|---|---|---|
| S.24 | Et | Et | Me | $NO_2$ |
| S.25 | Et | Et | Me | 2-Cl-5-Tp |
| S.26 | $CH_2$—c-P | Et | Me | Cl |
| S.27 | 3-Me-2-Bu | 3-Me-2-Bu | Cl | Cl |
| S.28 | i-Bu | i-Bu | OMe | CN |
| S.29 | Me | n-Pr | Me | Cl |
| S.30 | $CH_2$—c-Pe | $CH_2$—c-Pe | Me | Cl |
| S.31 | Et | Et | Me | F |
| S.32 | Et | $CH_2$—c-Bu | Cl | Cl |
| S.33 | 4-F—Ph | Me | Me | CN |
| S.34 | $CH_2CH_2SCH_2$ | | Me | Cl |
| S.35 | n-Hex | n-Hex | Me | Cl |
| S.36 | $CH_2CH_2OH$ | $CH_2CH_2OH$ | Cl | Cl |
| S.37 | i-Pr | i-Pr | Br | $CF_3$ |
| S.38 | 3-Me-2-Bu | 3-Me-2-Bu | Me | Cl |
| S.39 | i-Pr | i-Pr | Me | Cl |
| S.40 | $(CH_2)_2$—c-Pr | $(CH_2)_2$—c-Pr | Me | CN |
| S.41 | i-Pr | i-Pr | Cl | CN |
| S.42 | i-Pr | i-Pr | Me | F |
| S.43 | n-Pe | n-Pe | Me | CN |
| S.44 | 3-Me-1-Bu | 3-Me-1-Bu | Me | Cl |
| S.45 | i-Pr | c-Pr | Cl | Cl |
| S.46 | Me | Me | Me | I |
| S.47 | $CH_2$—c-Pr | i-Pr | Cl | CN |
| S.48 | Et | Me | Me | I |
| S.49 | Et | Et | Me | CH(=N—OH) |
| S.50 | $CH_2$—c-Pe | $CH_2$—c-Pe | Cl | Cl |
| S.51 | Et | c-Pr | Cl | Cl |
| S.52 | $CH_2$—c-Pt | Et | Me | CN |
| S.53 | $CH_2CH_2CH_2CH_2$ | | Me | CN |
| S.54 | $CH_2$—c-Bu | Et | Me | CN |
| S.55 | Et | c-Pr | Me | Cl |
| S.56 | $CH_2$—c-Bu | $CH_2$—c-Bu | Me | CN |
| S.57 | Me | Me | c-Pr | Cl |
| S.58 | $(CH_2)_2$—c-Pr | Et | Me | Cl |
| S.59 | i-Pr | i-Pr | OMe | Cl |
| S.60 | n-Pe | $CH_2CH_2OH$ | Me | Cl |
| S.61 | Et | Et | Me | $R^{3b}$-1 |
| S.62 | Et | i-Pr | Cl | Cl |
| S.63 | 2-EtHex | 2-EtHex | Cl | Cl |
| S.64 | i-Bu | i-Bu | Cl | Cl |
| S.65 | Et | Et | Me | CN |
| S.66 | $CH_2$—c-Pe | i-Pr | Me | Cl |
| S.67 | $CH_2$—c-Pe | i-Pr | Cl | Cl |
| S.68 | n-Hex | n-Hex | Me | CN |
| S.69 | Et | $CH_2CH_2$—c-Pr | Me | CN |
| S.70 | Et | Et | Me | $R^{3b}$-2 |
| S.71 | Et | Et | c-Pr | Cl |
| S.72 | $CH_2$—c-Pe | Et | Cl | Cl |
| S.73 | $CH_2$—c-Pr | $CH_2$—c-Pr | Cl | CN |
| S.74 | $CH_2CH_2CH_2CH_2$ | | Me | Cl |
| S.75 | $CH_2$—c-Bu1 | i-Pr | Me | CN |
| S.76 | Et | $CH=CH_2$ | Me | CN |
| S.77 | n-Pe | n-Pe | Me | Cl |
| S.78 | Et | Et | Me | Br |
| S.79 | Me | Me | Me | CN |
| S.80 | $CH_2CH_2CH_2CH_2CH_2$ | | Me | I |
| S.81 | $CH_2CH_2CH_2CH_2$ | | Me | CN |
| S.82 | Et | Et | Me | 3-isoxazolyl |
| S.83 | i-Pr | $(CH_2)_2$—c-Pr | Me | Cl |
| S.84 | i-Pr | i-Pr | Et | Cl |
| S.85 | Et | Et | Et | Cl |
| S.86 | i-Pr | c-Pr | Me | Cl |
| S.87 | $CH_2CH_2CH_2CH_2$ | | Br | Cl |
| S.88 | Et | Et | Br | $CF_3$ |
| S.89 | i-Pr | i-Pr | Me | $NO_2$ |
| S.90 | 3-Me-2-Bu | Et | Cl | Cl |
| S.91 | $(CH_2)_2$—c-Pr | i-Pr | Me | CN |
| S.92 | Et | Et | Me | Cl |
| S.93 | i-Pr | i-Pr | Me | 3-isoxazolyl |
| S.94 | $CH_2CH_2OH$ | n-Pe | Me | CN |
| S.95 | $(CH_2)_2$—c-Pr | Et | Cl | Cl |
| S.96 | Me | 4-F—Ph | Me | Cl |
| S.97 | i-Pr | i-Pr | Cl | CH(=N—OH) |
| S.98 | $CH_2$—c-Bu | i-Pr | Cl | Cl |
| S.99 | Me | n-Pr | Me | I |
| S.100 | i-Bu | i-Bu | c-Pr | Cl |
| S.101 | 2-EtHex | 2-EtHex | Me | CN |

TABLE C.2-continued compounds of formula Ia with $R^4$ = H (compounds S.25 to S.158)

| # | $R^1$ | $R^2$ | $R^{3a}$ | $R^{3b}$ |
|---|---|---|---|---|
| S.102 | Et | Et | Me | $R^{3b}$-3 |
| S.103 | 2-Bu | Me | Me | Cl |
| S.104 | $CH_2CH_2SCH_2$ | | Me | CN |
| S.105 | $(CH_2)_2$—c-Pr | i-Pr | Me | Cl |
| S.106 | Me | 4-Fl—Ph | Me | I |
| S.107 | $(CH_2)_2$—c-Pr | $(CH_2)_2$—c-Pr | Cl | Cl |
| S.108 | n-Pe | n-Pe | Cl | Cl |
| S.109 | i-Pr | $CH(CH_3)$—c-Pr | Cl | Cl |
| S.110 | 3-Me-1-Bu | 3-Me-1-Bu | Me | CN |
| S.111 | $(CH_2)_2$—c-Pr | $(CH_2)_2$—c-Pr | Me | Cl |
| S.112 | i-Pr | i-Pr | Me | CH(=N—OH) |
| S.113 | Me | Me | OMe | Cl |
| S.114 | 2-EtHex | 2-EtHex | Me | Cl |
| S.115 | Et | Et | Cl | CN |
| S.116 | n-Pe | $CH_2CH_2OH$ | Me | I |
| S.117 | Me | Me | Et | Cl |
| S.118 | $CH_2$—c-Bu | i-Pr | Me | Cl |
| S.119 | $(CH_2)_2$—c-Pr | i-Pr | Cl | Cl |
| S.120 | i-Bu | i-Bu | Et | Cl |
| S.121 | n-Hex | n-Hex | Cl | Cl |
| S.122 | i-Pr | i-Pr | Me | I |
| S.123 | $CH_2CH_2OH$ | $CH_2CH_2OH$ | Me | CN |
| S.124 | 2-Bu | Me | Me | CN |
| S.125 | $CH_2CH_2Cl$ | Et | Me | I |
| S.126 | $CH_2$—c-Pr | Et | Cl | CN |
| S.127 | $CH_2$—c-Bu | $CH_2$—c-Bu | Cl | Cl |
| S.128 | $CH_2CH_2SCH_2$ | | Cl | Cl |
| S.129 | $CH_2CH_2SCH_2$ | | Me | I |
| S.130 | Me | Et | Me | CN |
| S.131 | Et | Et | Cl | CH(=N—OH) |
| S.132 | $CH_2CH_2CH_2CH_2$ | | Cl | Cl |
| S.133 | Et | i-Pr | Me | Cl |
| S.134 | i-Bu | i-Bu | OMe | Cl |
| S.135 | Me | Me | OMe | CN |
| S.136 | $CH_2$—c-Bu | Et | Me | Cl |
| S.137 | $CH_2CH_2CH_2CH_2$ | | Me | I |
| S.138 | $CH_2$—c-Pr | Et | Cl | Cl |
| S.139 | i-Pr | i-Pr | Cl | $CF_3$ |
| S.140 | $CH_2CH_2OH$ | $CH_2CH_2OH$ | Me | Cl |
| S.141 | $CH_2$—c-Pe | $CH_2$—c-Pe | Me | CN |
| S.142 | Et | Et | Cl | $CF_3$ |
| S.143 | Et | Et | OMe | Cl |
| S.144 | i-Pr | i-Pr | Me | Br |
| S.145 | Et | Et | Me | $R^{3b}$-4 |
| S.146 | i-Pr | i-Pr | Me | 2-Cl-5-Tp |
| S.147 | Et | 3-Me-2-Bu | Me | Cl |
| S.148 | i-Pr | i-Pr | Me | CN |
| S.149 | Et | Me | Me | Cl |
| S.150 | $CH_2$—c-Pe | i-Pr | Me | CN |
| S.151 | i-Pr | i-Pr | c-Pr | Cl |
| S.152 | $CH_2$—c-Bu | $CH_2$—c-Bu | Me | Cl |
| S.153 | i-Pr | 3-Me-2-Bu | Me | Cl |
| S.154 | Me | Me | Cl | Cl |
| S.155 | 3-Me-1-Bu | 3-Me-1-Bu | Cl | Cl |
| S.156 | i-Pr | 3-Me-2-Bu | Cl | Cl |
| S.157 | n-Pr | Me | Me | CN |
| S.158 | Me | Me | $OCHF_2$ | Cl |

Preparation of the Compounds of Formula V (Examples 1 to 5)

Example 1a 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a solution of 2-amino-3,5-dichloro-N-(diethyl-$\lambda^4$-sulfanylidene)benzamide (8.82 g, 25.6 mmol) in pyridine (30 mL) was added N,N-dimethylamino pyridine (312 mg, 2.56 mmol, 10.0 mol %). At 90° C., a solution of 2-(3-chloro-2-pyridyl)-5-(trifluoromethyl)pyrazole-3-carbonyl chloride (10.90 g, 29.12 mmol, 1.100 equiv.) in pyridine (50 mL) was added dropwise and the mixture was stirred for 1 h. The mixture was cooled and concentrated in vacuum. Water was added and the mixture was extracted with ethyl acetate. Combined organic layers were washed with water and brine, dried over sodium sulphate, filtered and concentrated in vacuum. Flash-chromatography on silica gel yielded the title compound (4.12 g, 28%).

Characterization by $^1$H-NMR (400 MHz, DMSO-$d_6$): δ[delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 1b 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a suspension of potassium carbonate (7.78 g, 56.3 mmol, 1.10 equiv) and 2-amino-3,5-dichloro-N-(diethyl-$\lambda^4$-sulfanylidene)benzamide (15.00 g, 51.16 mmol) in toluene (50 mL) was added a solution of 2-(3-chloro-2-pyridyl)-5-(trifluoromethyl)-pyrazole-3-carbonyl chloride (17.62 g, 51.15 mmol, 1.000 equiv.) in toluene (55 mL) at 60° C. After 1.5 h at this temperature, the mixture was cooled and water was added. The resulting precipitate was collected by filtration, washed with water and petrol ether and dried to obtain the title compound (18.73 g, 65%).

Characterization by $^1$H-NMR (400 MHz, DMSO-$d_6$): δ[delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 1c 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a suspension of potassium carbonate (7.06 g, 50 mmol, 1.50 equiv) and 2-amino-3,5-dichloro-N-(diethyl-$\lambda^4$-sulfanylidene)benzamide (9.98 g, 34.05 mmol) in dichloromethane (50 mL) was added a solution of 2-(3-chloro-2-pyridyl)-5-(trifluoromethyl)pyrazole-3-carbonyl chloride (13.8 g, 37.8 mmol, 1.10 equiv.) in dichloromethane (50 mL) at room temperature. After 3 h at this temperature, the solids were filtered off and water was added to the filtrate. The mixture was extracted with dichloromethane and dried over $Na_2SO_4$. After filtration, the filtrate was concentrated in vacuum and the resulting solids were crystallized from diethyl ether to yield the title compound (10.1 g, 52%).

Characterization by $^1$H-NMR (400 MHz, DMSO-$d_6$): δ[delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 1d 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a suspension of potassium carbonate (1.42 g, 10 mmol, 1.50 equiv) and 2-amino-3,5-dichloro-N-(diethyl-$\lambda^4$-sulfanylidene)benzamide (2.00 g, 6.83 mmol) in dichloromethane (10 mL) was added a solution of 2-(3-chloro-2-pyridyl)-5-(trifluoromethyl)pyrazole-3-carbonyl chloride (2.77 g, 7.59 mmol, 1.10 equiv.) in dichloromethane (5 mL) at room temperature. After 2 h at this temperature, the solids were filtered off and water was added to the filtrate. The mixture was extracted with dichloromethane and dried over $Na_2SO_4$. After filtration, the filtrate was concentrated in vacuum and the resulting solids were crystallized from diethyl ether to yield the title compound (2.6 g, 67%).

Characterization by $^1$H-NMR (400 MHz, DMSO-$d_6$):
δ[delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 1e 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a suspension of potassium carbonate (8.08 g, 58.5 mmol, 1.50 equiv) and 2-amino-3,5-dichloro-N-(diethyl-$\lambda^4$-sulfanylidene)benzamide (11.43 g, 38.98 mmol) in acetonitrile (100 mL) was added a solution of 2-(3-chloro-2-pyridyl)-5-(trifluoromethyl)pyrazole-3-carbonyl chloride (15.8 g, 43.31 mmol, 1.10 equiv.) in acetonitrile (50 mL) at room temperature. After 6 h at this temperature, the solids were filtered off. The resulting filtrate was washed with water and dried over $Na_2SO_4$. After filtration, the filtrate was concentrated in vacuum and the resulting solids were crystallized from diisopropyl ether to yield the title compound (19.53 g, 88%).

Characterization by $^1$H-NMR (400 MHz, DMSO-$d_6$):
δ[delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 2a

Synthesis of 2-(3-chloro-2-pyridyl)-N-[2,4-dichloro-6-[(bis-2-propyl-$\lambda^4$-sulfanylidene)carbamoyl]phenyl]-5-(trifluoromethyl)pyrazole-3-carboxamide To a suspension of potassium carbonate (0.892 g, 6.46 mmol, 1.10 equiv) and 2-amino-3,5-dichloro-N-(bis-2-propyl-$\lambda^4$-sulfanylidene)benzamide (2.05 g, 5.87 mmol) in toluene (30 mL) was added a solution of 2-(3-chloro-2-pyridyl)-5-(trifluoromethyl)pyrazole-3-carbonyl chloride (2.02 g, 5.87 mmol, 1.00 equiv.) in toluene (20 mL) at 60° C. After 45 min at this temperature, the mixture was cooled and water was added. The resulting precipitate was collected by filtration, washed with water and toluene and dried to obtain the title compound (3.07 g, 84%).

Characterization by UPLC-MS: 1.395 min, M=602.1

Example 2b

Synthesis of 2-(3-chloro-2-pyridyl)-N-[2,4-dichloro-6-[(bis-2-propyl-$\lambda^4$-sulfanylidene)carbamoyl]phenyl]-5-(trifluoromethyl)pyrazole-3-carboxamide To a solution of 6,8-dichloro-1H-3,1-benzoxazine-2,4-dione (2.50 g, 10.8 mmol) in anhydrous propylene carbonate (20 mL) was added bis-2-methylpropyl sulfinium sulfate (2.75 g, 7.53 mmol, 0.70 equiv.) and triethyl amine (1.14 g, 11.3 mmol, 1.10 equiv.) at room temperature. The mixture was stirred for 3 h. ⅓ of the resulting mixture was transferred to a separate reaction flask and used for the next transformation as such.

To a solution of the above obtained solution of 2-amino-3,5-dichloro-N-(bis-2-propyl-$\lambda^4$-sulfanylidene)benzamide (6.7 mL; ~3.6 mmol) was added potassium carbonate (0.60 g, 4.3 mmol, 1.20 equiv) and a solution of 2-(3-chloro-2-pyridyl)-5-(trifluoromethyl)pyrazole-3-carbonyl chloride (1.34 g, 4.31 mmol, 1.20 equiv.) in toluene (10 mL) at room temperature. After 6 h at this temperature, the mixture poured onto water and treated with a small amount of ethanol under sonification. The resulting precipitate was collected by filtration, washed with water and diisopropyl ether and dried to obtain the title compound (1.29 g, 60%).

Characterization by $^1$H-NMR (400 MHz, DMSO-$d_6$):
δ[delta]=1.18 (d, 6H), 1.22 (d, 6H), 3.30 (m, 2H), 7.68 (dd, 1H), 7.75 (m, 2H), 7.81 (s, 1H), 8.21 (d, 1H), 8.54 (d, 1H), 10.76 (s, 1H).

Example 3a

Synthesis of 2-(3-chloro-2-pyridyl)-N-[2-methyl-4-chloro-6-[(bis-2-propyl-$\lambda^4$-sulfanylidene)carbamoyl]phenyl]-5-(trifluoromethyl)pyrazole-3-carboxamide To a suspension of potassium carbonate (1.79 g, 10 mmol, 1.30 equiv) and 2-amino-3-methyl-5-chloro-N-(bis-2-propyl-$\lambda^4$-sulfanylidene)benzamide (3.00 g, 9.97 mmol) in dichloromethane (20 mL) was added a solution of 2-(3-chloro-2-pyridyl)-5-(trifluoromethyl)pyrazole-3-carbonyl chloride (4.000 g, 10.97 mmol, 1.10 equiv.) in dichloromethane (10 mL) at room temperature. After 2 h at this temperature, the solids were filtered off. The resulting filtrate was washed with water and dried over $Na_2SO_4$. After filtration, the filtrate was concentrated in vacuum and the resulting solids were crystallized from diisopropyl ether to yield the title compound (3.1 g, 54%).

Characterization by UPLC-MS: 1.303 min, M=574.3

Example 3b

Synthesis of 2-(3-chloro-2-pyridyl)-N-[2-methyl-4-chloro-6-[(bis-2-propyl-$\lambda^4$-sulfanylidene)carbamoyl]phenyl]-5-(trifluoromethyl)pyrazole-3-carboxamide To a suspension of potassium carbonate (126.01 g, 911.76 mmol, 1.30 equiv) and 2-amino-3-methyl-5-chloro-N-(bis-2-propyl-$\lambda^4$-sulfanylidene)benzamide (211 g, 701 mmol) in dichloromethane (300 mL) was added a solution of 2-(3-chloro-2-pyridyl)-5-(trifluoromethyl)pyrazole-3-carbonyl chloride (256.78 g, 771.49 mmol, 1.10 equiv.) in dichloromethane (200 mL) at room temperature. After 2 h at this temperature, the solids were filtered off. The resulting filtrate was washed with water and dried over $Na_2SO_4$. After filtration, the filtrate was concentrated in vacuum and the resulting solids were crystallized from diisopropyl ether to yield the title compound (344.2 g, 85%).

Characterization by UPLC-MS: 1.303 min, M=574.3

Example 4a 2-(3-chloro-2-pyridyl)-N-[2-methyl-4-chloro-6-[(diethyl-$\lambda^4$-sulfanylidene)carbamoyl]phenyl]-5-(trifluoromethyl)pyrazole-3-carboxamide (Compound Va-1)

To a suspension of potassium carbonate (0.71 g, 10 mmol, 1.3 equiv) and 2-amino-3-methyl-5-chloro-N-(diethyl-$\lambda^4$- sulfanylidene)benzamide (1.42 g, 3.96 mmol) in propylene carbonate (20 mL) was added a solution of 2-(3-chloro-2-pyridyl)-5-(trifluoromethyl)pyrazole-3-carbonyl chloride (1.35 g, 4.35 mmol, 1.10 equiv.) in propylene carbonate (10 mL) at room temperature. After 24 h at this temperature, the mixture was poured onto water and spiked with ethanol under vigorous stirring. The resulting solids were collected by filtration and contained pure title compound (1.57 g, 73%).

LCMS (Method B): r.t. 1.19 min, m/z 546.1 (M+H)+; m.p. 189° C.;

$^1$H NMR (500 MHz, DMSO) [delta]: 10.87 (s, 1H), 8.53 (d, 1H), 8.22 (d, 1H), 7.75 (s, 1H), 7.65 (m, 2H), 7.40 (s, 1H), 3.09 (m, 2H), 2.92 (m, 2H) 1.15 (m, 6H).

Example 4b 2-(3-chloro-2-pyridyl)-N-[2-methyl-4-chloro-6-[(diethyl-$\lambda^4$-sulfanylidene)carbamoyl]phenyl]-5-(trifluoromethyl)pyrazole-3-carboxamide To a solution of 2-(3-chloro-2-pyridyl)-5-(trifluoromethyl)pyrazole-3-carbonyl chloride (150 g, 435 mmol) in acetonitrile (900 mL) at room temperature was added potassium carbonate (59 g, 427 mmol). A solution of 2-amino-5-chloro-N-(diethyl-sulfanylidene)-3-methyl-benzamide (117 g, 427 mmol) in acetonitrile (100 mL) was added dropwise within 1 hour while maintaining a reaction temperature of 25-28° C. with occasional cooling (slightly exothermic reaction). The mixture was stirred for 16 hours at room temperature. The reaction mixture was then poured on ice-water mixture (5 L) and the pH was adjusted to 7-8 with concentrated HCl. The mixture stirred for an additional 2 hours. The light brown solid was filtered, washed with water and dried under air to give the crude product (229 g).

3 combined batches of crude product (789 g) were suspended in acetonitrile (2.6 L) and dissolved upon heating at 60° C. After 1 hour of stirring at 60° C. the solution was cooled by means of an ice-bath and the thereby formed solid was filtered off. The mother-liquor was concentrated to 300 mL and cooled with ice-bath. Thereby additional solid formed was filtered. The combined solids were washed with cold acetonitrile and dried at 50° C. in a vacuum-oven over night to give the title product (703 g, 89%) as a crystalline white solid. The crystalline material was analyzed by means of DSC and by means of X-ray powder diffractometry (XRPD). The data revealed that form A of Va-1 was obtained.

Example 5

2-(3-chloro-2-pyridyl)-N-[2-methyl-4-chloro-6-[(di-2-propyl-$\lambda^4$-sulfanylidene)carbamoyl]phenyl]-5-(trifluoromethyl)pyrazole-3-carboxamide (Compound Va-2)

To a suspension of bis-2-isopropyl sulfinium sulfate (192 g, 0.53 mol, 0.68 equiv.) in DMSO (700 mL) a solution of 6-chloro-8-methyl-1H-3,1-benzoxazine-2,4-dione (162 g, 0.77 mol) in anhydrous DMSO (300 mL) was added at 22° C. followed by addition of triethylamine (117.4 mL, 84.75 g, 0.85 mol, 1.1 equiv.) at 22° C. The mixture was stirred for 6 h, and then added dropwise to ice-water. The mixture was extracted with dichloromethane and the combined organic layers were dried over sodium sulphate and concentrated in vacuo. The residue was triturated with diisopropyl ether to yield the title compound (189.9 g, 82%).

Characterization by $^1$H-NMR (400 MHz, CDCl$_3$): δ[delta]=1.40 (2×d, 12H), 2.11 (s, 3H), 3.23 (m, 2H), 6.05 (br. s, 2H), 7.03 (s, 1H), 8.01 (s, 1H).

HPLC: r.t. 0.908, m/z 301.3

To a suspension of potassium carbonate (9.73 g, 70.0 mmol, 1.10 equiv) and 2-amino-5-chloro-N-(diisopropyl-$\lambda^4$-sulfanylidene)-3-methyl-benzamide (18.7 g, 62.4 mmol, 1.00 equiv) in toluene (80 mL) a solution of 2-(3-chloro-2-pyridyl)-5-(trifluoromethyl)pyrazole-3-carbonyl chloride (20.1 g, 64.1 mmol, 1.03 equiv.) in toluene (40 mL) was added at 60° C. After 35 minutes at 60° C., the reaction mixture was cooled to room temperature and diluted with EtOAc (50 mL) and water (50 mL). The organic phase was washed with water (50 mL), 0.1 M HCl (50 mL), dried over Na$_2$SO$_4$ and concentrated. The crude product was recrystallized from methyl tert-butyl ether to yield the title compound (24.4 g, 66%). The crystalline material was analyzed by means of DSC and by means of X-ray powder diffractometry (XRPD). The data revealed that form I of Va-2 was obtained.

Characterization by $^1$H-NMR (400 MHz, DMSO-d$_6$): δ[delta]=1.20 (d, 6H), 1.30 (d, 6H), 2.15 (s, 3H), 3.30 (m, 2H), 7.41 (s, 1H), 7.62 (m, 2H), 7.80 (s, 1H), 8.22 (d, 1H), 8.52 (d, 1H), 10.88 (s, 1H).

HPLC: r.t. 3.820, m/z 574.1

By the methods described in examples 1 to 5 the compounds of formula (V-A) or V-B, summarized in the following tables T.1 to T.5, were prepared:

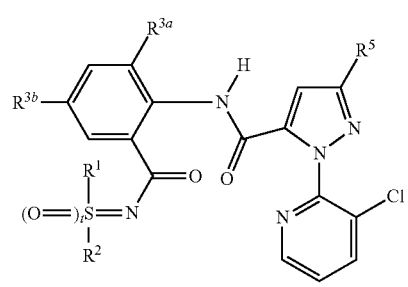

(V-A)

Compounds V-A are compounds of the formula Va with $R^6$=Cl, $R^4$=H and Q=N.

In tables T.1 to T.5 the following abbreviations are used:
mp: melting point
$R^{3b}$-1: CH(=N—OCH3)
$R^{3b}$-2: 3-pyrazol-1H-yl
$R^{3b}$-3: CH(=N—NHCH$_2$CF$_3$)
$R^{3b}$-4: CH[=N—N(CH$_3$)$_2$]
Me: Methyl
OMe: Methoxy
Et: Ethyl
i-Pr: isopropyl
i-Bu: isobutyl
3-Me-2-Bu: 3-methyl-2-butyl
3-Me-1-Bu: 3-methyl-1-butyl
n-Bu: n-butyl
2-Bu: 2-butyl
n-Pe: n-pentyl
n-Hex: n-hexyl
2-EtHex: 2-ethylhexyl
c-Pr: cyclopropyl
c-Bu: cyclobutyl
c-Pe: cyclopentyl
2-Cl-5-Tp: 2-chloro-5-thiophenyl
4-F-Ph: 4-fluorophenyl

TABLE T.1

Compounds of formula V-A where $R^5$ is $CF_3$.

| # | t | $R^1$ | $R^2$ | $R^{3a}$ | $R^{3b}$ | MS | RT[min] | m/z |
|---|---|---|---|---|---|---|---|---|
| 1 | 0 | Et | Et | Cl | Cl | A | 3.450 | 565.90 |
| 2 | 0 | i-Pr | i-Pr | Cl | Cl | A | 3.835 | 596.05 |
| 3 | 0 | CH₂—c-Pr | CH₂—c-Pr | Cl | Cl | B | 1.518 | 620.0 |
| 4 | 0 | i-Bu | i-Bu | Me | Cl | B | 1.395 | 602.1 |
| 5 | 0 | Et | Et | Me | NO₂ | B | 1.19 | 557 |
| 6 | 0 | CH₂—c-Pr | i-Pr | Me | Cl | B | 1.372 | 586.1 |
| 7 | 0 | Et | Et | Me | 2-Cl-5-Tp | A | 3.989 | 628.90 |
| 8 | 0 | CH₂—c-P | Et | Me | Cl | B | 1.372 | 600.3 |
| 9 | 0 | 3-Me-2-Bu | 3-Me-2-Bu | Cl | Cl | B | 1.488 | 652.1 |
| 10 | 0 | i-Bu | i-Bu | OMe | CN | A | 3.701 | 611 |
| 11 | 0 | Me | n-Pr | Me | Cl | | logP: 3.2 [pH = 10.0] | |
| 12 | 0 | CH₂—c-Pe | CH₂—c-Pe | Me | Cl | B | 1.500 | 654.3 |
| 13 | 0 | Et | Et | Me | F | B | 1.114 | 530 |
| 14 | 0 | Et | CH₂—c-Bu | Cl | Cl | B | 1.344 | 607.9 |
| 15 | 0 | 4-F—Ph | Me | Me | CN | | mp: 72° C. | |
| 16 | 0 | CH₂CH₂SCH₂ | | Me | Cl | A | 3.631 | 561.95 |
| 17 | 0 | n-Hex | n-Hex | Me | Cl | B | 1.58 | 660.4 |
| 18 | 0 | CH₂CH₂OH | CH₂CH₂OH | Cl | Cl | B | 1.064 | 600 |
| 19 | 0 | n-Pr | n-Pr | Cl | Cl | A | 3.981 | 595.95 |
| 20 | 0 | CH₂—c-Pr | Et | Me | Cl | A | 3.714 | 571.95 |
| 21 | 1 | n-Pe | CH₂CH₂OH | Me | Cl | | | |
| 22 | 0 | i-Pr | i-Pr | Br | CF₃ | B | 1.350 | 674.00 |
| 23 | 0 | 3-Me-2-Bu | 3-Me-2-Bu | Me | Cl | B | 1.473 | 630.3 |
| 24 | 0 | i-Pr | i-Pr | Me | Cl | | logP: 3.3 [pH = 10.0]. m.p: 142° C. | |
| 25 | 0 | (CH₂)₂—c-Pr | (CH₂)₂—c-Pr | Me | CN | B | 1.376 | 617.5 |
| 26 | 0 | i-Pr | i-Pr | Cl | CN | B | 1.262 | 585.3 |
| 27 | 0 | i-Pr | i-Pr | Me | F | A | 3.400 | 558 |
| 28 | 0 | n-Pe | n-Pe | Me | CN | B | 1.443 | 621.5 |
| 29 | 0 | 3-Me-1-Bu | 3-Me-1-Bu | Me | Cl | B | 1.491 | 630.4 |
| 30 | 0 | i-Pr | c-Pr | Cl | Cl | B | 1.282 | 593.8 |
| 31 | 0 | Me | Me | Me | I | | logP: 3.2 [pH = 10.0]; m.p: 165° C. | |
| 32 | 0 | CH₂—c-Pr | i-Pr | Cl | CN | B | 1.271 | 597.1 |
| 33 | 0 | Et | Me | Me | I | | logP: 3.3 [pH = 10.0]; m.p: 181° C. | |
| 34 | 1 | Et | Et | Cl | Cl | B | 1.242 | 584.2 |
| 35 | 0 | Et | Et | Me | CH(=N—OH) | A | 2.94 | 555 |
| 36 | 0 | CH₂—c-Pe | CH₂—c-Pe | Cl | Cl | B | 1.514 | 676.2 |
| 37 | 0 | Et | c-Pr | Cl | Cl | B | 1.253 | 578.1 |
| 38 | 0 | i-Pr | i-Pr | Br | Cl | A | 3.630 | 639.90 |
| 39 | 0 | CH₂—c-Pt | Et | Me | CN | B | 1.310 | 591.4 |
| 40 | 0 | i-Pr | i-Pr | Br | Br | A | 3.665 | 683.90 |
| 41 | 0 | CH₂CH₂CH₂CH₂ | | Me | CN | | m.p: 194° C. | |
| 42 | 0 | CH₂—c-Bu | Et | Me | CN | B | 1.282 | 577.4 |
| 43 | 0 | Et | c-Pr | Me | Cl | B | 1.238 | 558.0 |
| 44 | 0 | CH₂—c-Bu | CH₂—c-Bu | Me | CN | B | 1.390 | 617.2 |
| 45 | 0 | Me | Me | c-Pr | Cl | A | 3.385 | 545 |
| 46 | 0 | (CH₂)₂—c-Pr | Et | Me | Cl | B | 1.311 | 586.4 |
| 47 | 0 | i-Pr | i-Pr | OMe | Cl | A | 3.343 | 592 |
| 48 | 0 | n-Pe | CH₂CH₂OH | Me | Cl | | logP: 3.6 [pH = 10.0]; m.p: 133° C. | |
| 49 | 0 | Et | Et | Me | $R^{3b}$-1 | A | 3.205 | 570 |
| 50 | 0 | Et | i-Pr | Cl | Cl | B | 1.303 | 581.8 |
| 51 | 0 | 2-EtHex | 2-EtHex | Cl | Cl | B | 1.679 | 461.4 |
| 52 | 0 | i-Bu | i-Bu | Cl | Cl | B | 1.408 | 623.8 |
| 53 | 0 | Et | Et | Me | CN | B | 1.179 | 537.3 |
| 54 | 0 | CH₂—c-Pe | i-Pr | Me | Cl | B | 1.395 | 616 |
| 55 | 0 | CH₂—c-Pe | i-Pr | Cl | Cl | B | 1.401 | 636 |
| 56 | 0 | n-Hex | n-Hex | Me | CN | B | 1.534 | 649.2 |
| 57 | 0 | Et | CH₂CH₂—c-Pr | Me | CN | B | 1.264 | 577.4 |
| 58 | 0 | i-Pr | i-Pr | Cl | Br | A | 3.710 | 639.90 |
| 59 | 0 | Et | Et | Br | Cl | A | 3.633 | 611.85 |
| 60 | 0 | Et | Et | Me | $R^{3b}$-2 | A | 2.896 | 578.00 |
| 61 | 0 | Et | Et | c-Pr | Cl | A | 3.580 | 573 |
| 62 | 0 | CH₂—c-Pe | Et | Cl | Cl | B | 1.385 | 620.2 |
| 63 | 0 | CH₂—c-Pr | CH₂—c-Pr | Cl | CN | B | 1.287 | 609.1 |
| 64 | 0 | CH₂CH₂CH₂CH₂ | | Me | Cl | A | 3.481 | 544.05 |
| 65 | 0 | CH₂—c-BuI | i-Pr | Me | CN | B | 1.306 | 591.4 |
| 66 | 0 | Et | CH=CH₂ | Me | CN | | m.p: 60° C. | |
| 67 | 0 | n-Pe | n-Pe | Me | Cl | B | 1.492 | 630.4 |
| 68 | 0 | Et | Et | Me | Br | B | 1.225 | 592 |
| 69 | 0 | Me | Me | Me | CN | | m.p: 225° C. | |
| 70 | 0 | Et | Et | Br | Br | B | 1.218 | 655.9 |
| 71 | 0 | CH₂CH₂CH₂CH₂CH₂ | | Me | I | | logP: 3.6 [pH = 10.0]; m.p: 215° C. | |
| 72 | 0 | CH₂CH₂CH₂CH₂CH₂ | | Me | CN | | m.p: 85° C. | |
| 73 | 0 | Et | Et | Me | 3-isoxazolyl | B | 1.094 | 581 |
| 74 | 0 | i-Pr | (CH₂)₂—c-Pr | Me | Cl | B | 1.378 | 600.2 |
| 75 | 0 | i-Pr | i-Pr | Et | Cl | A | 3.785 | 589 |
| 76 | 0 | Et | Et | Et | Cl | A | 3.549 | 561 |

TABLE T.1-continued

Compounds of formula V-A where $R^5$ is $CF_3$.

| # | t | $R^1$ | $R^2$ | $R^{3a}$ | $R^{3b}$ | MS | RT[min] | m/z |
|---|---|---|---|---|---|---|---|---|
| 77 | 0 | i-Pr | c-Pr | Me | Cl | B | 1.257 | 572.1 |
| 78 | 0 | CH₂CH₂CH₂CH₂ | | Br | Cl | A | 3.537 | 609.85 |
| 79 | 0 | Et | Et | Br | $CF_3$ | B | 1.301 | 646.1 |
| 80 | 0 | i-Pr | i-Pr | Me | $NO_2$ | B | 1.274 | 585 |
| 81 | 0 | 3-Me-2-Bu | Et | Cl | Cl | B | 1.351 | 610 |
| 82 | 0 | (CH₂)₂—c-Pr | i-Pr | Me | CN | B | 1.313 | 591.3 |
| 83 | 0 | Et | Et | Me | Cl | B | 1.207 | 546.1 |
| 84 | 0 | i-Pr | i-Pr | Me | 3-isoxazolyl | B | 1.155 | 609.0 |
| 85 | 0 | Et | Et | $CF_3$ | Br | B | 1.248 | 645.9 |
| 86 | 0 | CH₂CH₂OH | n-Pe | Me | CN | | m.p: 47° C. | |
| 87 | 1 | Me | Me | Me | Cl | B | 1.191 | 534.0 |
| 88 | 0 | (CH₂)₂—c-Pr | Et | Cl | Cl | B | 1.319 | 608.2 |
| 89 | 0 | CH₂—c-Pr | CH₂—c-Pr | Me | Cl | A | 3.735 | 598.0 |
| 90 | 0 | Me | 4-F-Ph | Me | Cl | | m.p: 185° C. | |
| 91 | 0 | i-Pr | i-Pr | Cl | CH(=N—OH) | A | 3.238 | 603 |
| 92 | 0 | CH₂—c-Bu | i-Pr | Cl | Cl | B | 1.372 | 622.2 |
| 93 | 0 | Me | n-Pr | Me | I | | logP: 3.6 [pH = 10.0]; m.p: 85° C. | |
| 94 | 0 | i-Bu | i-Bu | c-Pr | Cl | A | 4.135 | 629 |
| 95 | 0 | 2-EtHex | 2-EtHex | Me | CN | B | 1.662 | 705.3 |
| 96 | 0 | Et | Et | Cl | Br | A | 3.704 | 611.85 |
| 97 | 0 | Et | Et | Me | $R^{3b}$-3 | A | 3.421 | 637 |
| 98 | 1 | Me | n-Pr | Me | I | | | |
| 99 | 0 | 2-Bu | Me | Me | Cl | | m.p: 88° C. | |
| 100 | 0 | CH₂CH₂SCH₂ | | Me | CN | | m.p: 88° C. | |
| 101 | 0 | (CH₂)₂—c-Pr | i-Pr | Me | Cl | B | 1.365 | 600.3 |
| 102 | 0 | Me | 4-Fl-Ph | Me | I | | m.p: 182° C. | |
| 103 | 0 | (CH₂)₂—c-Pr | (CH₂)₂—c-Pr | Cl | Cl | B | 1.427 | 648 |
| 104 | 0 | n-Pe | n-Pe | Cl | Cl | B | 1.508 | 652.1 |
| 105 | 0 | i-Pr | CH(CH₃)—c-Pr | Cl | Cl | B | 1.263 | 553.9 |
| 106 | 0 | 3-Me-1-Bu | 3-Me-1-Bu | Me | CN | B | 1.443 | 621.6 |
| 107 | 0 | (CH₂)₂—c-Pr | (CH₂)₂—c-Pr | Me | Cl | B | 1.422 | 626.4 |
| 108 | 0 | i-Pr | i-Pr | Me | CH(=N—OH) | A | 3.087 | 583 |
| 109 | 0 | Me | Me | OMe | Cl | A | 2.911 | 535 |
| 110 | 0 | Me | Me | Me | Cl | | logP: 2.9 [pH = 10.0]; m.p: 182° C. | |
| 111 | 0 | 2-EtHex | 2-EtHex | Me | Cl | B | 1.604 | 680.5 |
| 112 | 0 | Et | Et | Cl | CN | B | 1.171 | 557.3 |
| 113 | 0 | n-Pe | CH₂CH₂OH | Me | I | | logP: 3.9 [pH = 10.0]; m.p: 135° C. | |
| 114 | 0 | Me | Me | Et | Cl | A | 3.352 | 533 |
| 115 | 0 | CH₂—c-Bu | i-Pr | Me | Cl | B | 1.373 | 600.3 |
| 116 | 0 | (CH₂)₂—c-Pr | i-Pr | Cl | Cl | B | 1.374 | 622.2 |
| 117 | 0 | i-Bu | i-Bu | Et | Cl | A | 4.105 | 618 |
| 118 | 0 | n-Hex | n-Hex | Cl | Cl | B | 1.588 | 680.3 |
| 119 | 0 | n-Pr | n-Pr | Me | Cl | B | 1.318 | 574.0 |
| 120 | 0 | i-Pr | i-Pr | Me | I | | logP: 3.4 [pH = 10.0]; m.p: 75° C. | |
| 121 | 0 | CH₂CH₂OH | CH₂CH₂OH | Me | CN | B | 1.005 | 569.1 |
| 122 | 0 | 2-Bu | Me | Me | CN | | m.p: 66° C. | |
| 123 | 0 | CH₂CH₂Cl | Et | Me | I | | m.p: 164° C. | |
| 124 | 0 | CH₂—c-Pr | Et | Cl | CN | B | 1.236 | 583.2 |
| 125 | 0 | i-Pr | i-Pr | $CF_3$ | Br | B | 1.308 | 673.9 |
| 126 | 1 | Et | Et | Me | Cl | B | 1.256 | 562.2 |
| 127 | 0 | CH₂—c-Bu | CH₂—c-Bu | Cl | Cl | B | 1.449 | 648.1 |
| 128 | 0 | CH₂CH₂SCH₂ | | Cl | Cl | A | 3.613 | 583.85 |
| 129 | 0 | CH₂CH₂SCH₂ | | Me | I | | logP: 3.5 [pH = 10.0]; m.p: 148° C. | |
| 130 | 0 | Me | Et | Me | CN | | m.p: 65° C. | |
| 131 | 0 | Et | Et | Cl | CH(=N—OH) | A | 3.061 | 575 |
| 132 | 0 | CH₂CH₂CH₂CH₂ | | Cl | Cl | A | 3.543 | 564.00 |
| 133 | 0 | Et | i-Pr | Me | Cl | B | 1.527 | 560.0 |
| 134 | 0 | i-Bu | i-Bu | OMe | Cl | A | 3.742 | 620 |
| 135 | 0 | Me | Me | OMe | CN | A | 2.805 | 526 |
| 136 | 0 | CH₂—c-Bu | Et | Me | Cl | B | 1.327 | 586.3 |
| 137 | 0 | CH₂CH₂CH₂CH₂ | | Me | I | | logP: 3.1 [pH = 10.0]; m.p: 185° C. | |
| 138 | 0 | CH₂—c-Pr | Et | Cl | Cl | A | 3.704 | 594.0 |
| 139 | 0 | i-Pr | i-Pr | Cl | $CF_3$ | B | 1.358 | 628.1 |
| 140 | 0 | CH₂CH₂OH | CH₂CH₂OH | Me | Cl | B | 1.065 | 578.3 |
| 141 | 0 | CH₂—c-Pe | CH₂—c-Pe | Me | CN | B | 1.459 | 645.4 |
| 142 | 0 | Et | Et | Cl | $CF_3$ | B | 1.284 | 600.1 |
| 143 | 0 | Et | Et | OMe | Cl | A | 3.117 | 563 |
| 144 | 0 | i-Pr | i-Pr | $CF_3$ | Cl | B | 1.169 | 628.1 |
| 145 | 0 | i-Pr | i-Pr | Me | Br | B | 1.300 | 620.0 |
| 146 | 0 | Et | Et | Me | $R^{3b}$-4 | A | 3.053 | 583 |
| 147 | 0 | Et | Et | $CF_3$ | Cl | B | 1.231 | 600.0 |
| 148 | 0 | i-Pr | i-Pr | Me | 2-Cl-5-Tp | A | 4.181 | 666.00 |
| 149 | 0 | Et | 3-Me-2-Bu | Me | Cl | B | 1.342 | 588.1 |
| 150 | 0 | i-Pr | i-Pr | Me | CN | B | 1.253 | 565.3 |
| 151 | 0 | i-Pr | i-Pr | Me | Cl | B | 1.303 | 574.3 |
| 152 | 0 | Et | Me | Me | Cl | | logP: 2.9 [pH = 10.0]; m.p: 181° C. | |

TABLE T.1-continued

Compounds of formula V-A where $R^5$ is $CF_3$.

| # | t | $R^1$ | $R^2$ | $R^{3a}$ | $R^{3b}$ | MS | RT[min] | m/z |
|---|---|---|---|---|---|---|---|---|
| 153 | 0 | CH$_2$—c-Pe | i-Pr | Me | CN | B | 1.35 | 605.5 |
| 154 | 0 | CH$_2$—c-Pe | i-Pr | Cl | Cl | A | 3.993 | 607.95 |
| 155 | 0 | i-Pr | i-Pr | c-Pr | Cl | A | 3.787 | 601 |
| 156 | 0 | CH$_2$—c-Bu | CH$_2$—c-Bu | Me | Cl | B | 1.444 | 626.3 |
| 157 | 0 | i-Pr | 3-Me-2-Bu | Me | Cl | B | 1.364 | 602.3 |
| 158 | 0 | Me | Me | Cl | Cl | A | 3.372 | 539.95 |
| 159 | 0 | 3-Me-1-Bu | 3-Me-1-Bu | Cl | Cl | B | 1.489 | 652.1 |
| 160 | 0 | i-Pr | 3-Me-2-Bu | Cl | Cl | B | 1.409 | 623.9 |
| 161 | 0 | n-Pr | Me | Me | CN | | m.p: 70° C. | |
| 162 | 0 | Me | Me | OCHF$_2$ | Cl | A | 3.31 | 571 |

TABLE T.2

Compounds of formula V-A where $R^5$ is $CHF_2$.

| # | t | $R^1$ | $R^2$ | $R^{3a}$ | $R^{3b}$ | MS | RT[min] | m/z |
|---|---|---|---|---|---|---|---|---|
| 163 | 0 | CH$_2$—c-Pr | CH$_2$—c-Pr | Me | Cl | A | 3.702 | 580.0 |
| 164 | 1 | Et | Et | Me | Cl | A | 3.473 | 544 |
| 165 | 0 | CH$_2$—c-Pr | CH$_2$—c-Pr | Br | Cl | B | 1.275 | 646.1 |
| 166 | 0 | Et | Et | Br | Br | B | 1.171 | 638.1 |
| 167 | 0 | CH$_2$—c-Pr | CH$_2$—c-Pr | Cl | Cl | B | 1.269 | 602.2 |
| 168 | 0 | i-Bu | i-Bu | Br | Cl | B | 1.333 | 650.2 |
| 169 | 0 | Et | i-Pr | Cl | Cl | B | 1.174 | 564.2 |
| 170 | 0 | i-Bu | i-Bu | Me | CN | B | 1.254 | 575.4 |
| 171 | 0 | Et | Et | Br | Cl | B | 1.148 | 594.1 |
| 172 | 0 | Me | Me | Me | CN | B | 1.005 | 491.2 |
| 173 | 0 | Et | Et | Me | CN | B | 3.035 | 519 |
| 174 | 0 | i-Pr | i-Pr | Me | Cl | B | 1.225 | 556.3 |
| 175 | 0 | i-Bu | i-Bu | Cl | Cl | B | 1.329 | 606.2 |
| 176 | 0 | Et | Et | Cl | Cl | B | 1.144 | 549.9 |
| 177 | 0 | n-Pr | n-Pr | Me | Cl | A | 3.639 | 556.1 |
| 178 | 0 | Me | Me | Br | Br | B | 1.087 | 610.0 |
| 179 | 0 | i-Pr | i-Pr | Me | CN | A | 3.277 | 547.1 |
| 180 | 0 | i-Pr | i-Pr | Br | Br | B | 1.245 | 666.1 |
| 181 | 0 | Et | Et | Me | Cl | B | 1.134 | 528.2 |
| 182 | 0 | i-Pr | i-Pr | Cl | Cl | B | 1.24 | 578 |
| 183 | 0 | CH$_2$—c-Pr | CH$_2$—c-Pr | Br | Br | B | 1.282 | 690.1 |
| 184 | 0 | i-Bu | i-Bu | Br | Br | B | 1.346 | 694.3 |
| 185 | 0 | i-Pr | i-Pr | Br | Cl | B | 1.205 | 622.2 |
| 186 | 0 | Me | Me | Cl | Cl | B | 1.062 | 520.2 |
| 187 | 0 | i-Bu | i-Bu | Me | Cl | B | 1.329 | 584.3 |
| 188 | 0 | Me | Me | Me | Cl | B | 1.06 | 500.2 |
| 189 | 1 | Et | Et | Cl | Cl | B | 1.163 | 566.1 |

TABLE T.3

Compounds of formula V-A where $R^5$ is CN

| # | t | $R^1$ | $R^2$ | $R^{3a}$ | $R^{3b}$ | MS | RT[min] | m/z |
|---|---|---|---|---|---|---|---|---|
| 190 | 0 | n-Pe | n-Pe | Me | CN | B | 1.356 | 578.3 |
| 191 | 0 | Et | Et | Me | Cl | B | 1.098 | 503.3 |
| 192 | 0 | Et | Et | Cl | Cl | B | 1.119 | 524.9 |
| 193 | 0 | i-Pr | i-Pr | Me | Cl | B | 1.19 | 531.3 |
| 194 | 0 | i-Pr | i-Pr | Cl | Cl | B | 1.209 | 553.1 |

TABLE T.4

Compounds of formula V-A

| # | t | $R^1$ | $R^2$ | $R^{3a}$ | $R^{3b}$ | $R^5$ | MS | RT[min] | m/z |
|---|---|---|---|---|---|---|---|---|---|
| 195 | 0 | CH$_2$CH$_2$OH | n-Pe | Me | I | OCH$_2$CCH | | logP: 3.5 [pH = 10.0] | |
| 196 | 0 | i-Pr | i-Pr | Me | I | OCH$_2$CCH | | logP: 3.1 [pH = 10.0] | |
| 197 | 0 | i-Pr | i-Pr | Me | Cl | OCH$_2$CCH | | logP: 2.7 [pH = 10.0] | |
| 198 | 0 | Et | Et | Me | Cl | CHCl$_2$ | B | 1.194 | 562.2 |
| 199 | 0 | Me | Me | Me | H | CF$_3$ | | logP: 2.2 [pH = 10.0]; m.p: 206° C. | |
| 200 | 0 | CH$_2$CH$_2$SCH$_2$ | | Me | Cl | OCH$_2$CCH | | logP: 2.5 [pH = 10.0] | |
| 201 | 0 | Me | 4-F—Ph | Me | Cl | OCH$_2$CCH | | logP: 2.9 [pH = 10.0] | |

TABLE T.4-continued

Compounds of formula V-A

| # | t | R¹ | R² | R³ᵃ | R³ᵇ | R⁵ | MS | RT[min] | m/z |
|---|---|---|---|---|---|---|---|---|---|
| 202 | 0 | i-Pr | i-Pr | Cl | Cl | OCH₃ | A | 3.284 | 557.90 |
| 203 | 0 | Et | Et | Me | Cl | OCH₃ | A | 2.953 | 508.05 |
| 204 | 0 | Me | 4-F—Ph | Me | I | OCH₂CCH | | logP: 3.4 [pH = 10.0] | |
| 205 | 0 | | CH₂CH₂CH₂CH₂ | Me | H | CF₃ | A | 2.994 | 510.05 |
| 206 | 0 | Et | CH₂CH₂Cl | Me | H | CF₃ | | m.p: 171° C. | |
| 207 | 0 | Et | Et | Me | Cl | NO₂ | B | 1.154 | 523.2 |
| 208 | 0 | | CH₂CH₂SCH₂ | Me | H | CF₃ | | logP: 2.2 [pH = 10.0]; m.p: 188° C. | |
| 209 | 0 | | CH₂CH₂CH₂CH₂ | Me | Cl | OCH₂CCH | | logP: 2.8 [pH = 10.0] | |
| 210 | 0 | Me | Et | Me | H | CF₃ | | logP: 2.5 [pH = 10.0]; m.p: 181° C. | |
| 211 | 0 | n-Pr | Me | Me | H | CF₃ | | logP: 2.8 [pH = 10.0]; m.p: 143° C. | |
| 212 | 0 | Et | Et | Cl | Cl | OCH₃ | A | 3.096 | 529.95 |
| 213 | 0 | n-Pe | CH₂CH₂OH | Me | H | CF₃ | | logP: 3.4 [pH = 10.0]; m.p: 106° C. | |
| 214 | 0 | i-Pr | i-Pr | Me | H | CF₃ | | logP: 2.7 [pH = 10.0]; m.p: 192° C. | |
| 215 | 0 | Me | 4-F—Ph | Me | H | CF₃ | | logP: 3.2 [pH = 10.0]; m.p: 180° C. | |
| 216 | 0 | CH₂CH₂OH | n-Pe | Me | Cl | OCH₂CCH | | logP: 3.3 [pH = 10.0] | |
| 217 | 0 | | CH₂CH₂CH₂CH₂ | Br | Cl | Br | A | 3.285 | 619.85 |
| 218 | 0 | Et | Et | OMe | Cl | Br | A | 2.821 | 574 |
| 219 | 0 | | CH₂CH₂SCH₂ | Br | Cl | Br | A | 3.419 | 639.75 |
| 220 | 0 | | CH₂CH₂CH₂CH₂ | Me | Cl | Br | | logP: 3 [pH = 10.0]; m.p: 223° C. | |
| 221 | 0 | | CH₂CH₂SCH₂ | Me | I | Br | | logP: 3.3 [pH = 10.0]; m.p: 120° C. | |
| 222 | 0 | | CH₂CH₂CH₂CH₂ | Me | H | Br | | logP: 2.1 [pH = 10.0] | |
| 223 | 0 | Et | Me | Me | I | Br | | logP: 3.1 [pH = 10.0]; m.p: 124° C. | |
| 224 | 0 | Et | Me | Me | Cl | Br | | logP: 2.7 [pH = 10.0]; m.p: 192° C. | |
| 225 | 0 | Et | CH═CH₂ | Me | CN | Br | | m.p: 60° C. | |
| 226 | 0 | CH═CH₂ | Et | Me | Cl | Br | A | 3.622 | 555.90 |
| 227 | 0 | i-Bu | i-Bu | OMe | Cl | Br | A | 3.512 | 630 |
| 228 | 0 | Et | CH₂CH₂Cl | Me | Cl | Br | A | 3.484 | 591.74 |
| 229 | 0 | Et | Et | Me | Cl | Br | A | 3.309 | 557.95 |
| 230 | 0 | Et | CH═CH₂ | Me | I | Br | | m.p: 80° C. | |
| 231 | 0 | i-Pr | i-Pr | Cl | Cl | Br | A | 3.538 | 605.80 |
| 232 | 0 | | CH₂CH₂SCH₂ | Me | H | Br | | m.p: 169° C. | |
| 233 | 0 | Me | Me | OMe | Cl | Br | A | 2.605 | 546 |
| 234 | 0 | i-Pr | i-Pr | Me | CN | Br | | m.p: 185° C. | |
| 235 | 0 | Me | 4-F—Ph | Me | Cl | Br | | logP: 3.2 [pH = 10.0]; m.p: 195° C. | |
| 236 | 0 | i-Pr | i-Pr | Me | H | Br | | logP: 2.3 [pH = 10.0]; m.p: 180° C. | |
| 237 | 0 | Me | 4-F—Ph | Me | H | Br | | logP: 2.7 [pH = 10.0]; m.p: 120° C. | |
| 238 | 0 | Me | 4-F—Ph | Me | I | Br | | logP: 3.5 [pH = 10.0]; m.p: 201° C. | |
| 239 | 0 | | CH₂CH₂CH₂CH₂ | Cl | Cl | Br | A | 3.184 | 575.80 |
| 240 | 0 | n-Pe | CH₂CH₂OH | Me | CN | Br | | m.p: 50° C. | |
| 241 | 0 | n-Pr | Me | Me | CN | Br | | m.p: 70° C. | |
| 242 | 0 | n-Pr | Me | Me | Cl | Br | | logP: 2.9 [pH = 10.0]; m.p: 179° C. | |
| 243 | 0 | i-Pr | i-Pr | Me | Cl | Br | | logP: 2.9 [pH = 10.0] | |
| 244 | 0 | | CH₂CH₂CH₂CH₂ | Me | CN | Br | | m.p: 92° C. | |
| 245 | 0 | Me | 2-Bu | Me | CN | Br | | m.p: 71° C. | |
| 246 | 0 | | CH₂CH₂CH₂CH₂ | Me | I | Br | | logP: 2.9 [pH = 10.0]; m.p: 195° C. | |
| 247 | 1 | Me | Me | Me | CN | Br | B | 1.035 | 536.9 |
| 248 | 1 | | CH₂CH₂CH₂CH₂ | Me | Cl | Br | | | |
| 249 | 0 | Et | Me | Me | CN | Br | | m.p: 80° C. | |
| 250 | 0 | n-Pe | CH₂CH₂OH | Me | H | Br | | logP: 2.9 [pH = 10.0] | |
| 251 | 0 | 4-F—Ph | Me | Me | CN | Br | | m.p: 180° C. | |
| 252 | 0 | n-Pe | CH₂CH₂OH | Me | I | Br | | logP: 3.7 [pH = 10.0] | |
| 253 | 0 | i-Pr | i-Pr | Br | Cl | Br | A | 3.519 | 649.80 |
| 254 | 0 | Me | Me | Me | Cl | Br | A | 3.067 | 529.95 |
| 255 | 0 | Me | Me | Cl | Cl | Br | A | 3.015 | 549.80 |
| 256 | 0 | Me | Me | Me | CN | Br | | m.p: 205° C. | |
| 257 | 0 | i-Pr | i-Pr | Me | I | Br | | logP: 3.3 [pH = 10.0]; m.p: 75° C. | |
| 258 | 0 | n-Pe | CH₂CH₂OH | Me | Cl | Br | | logP: 3.4 [pH = 10.0]; m.p: 160° C. | |
| 259 | 0 | Me | Me | Me | I | Br | | logP: 3 [pH = 10.0]; m.p: 115° C. | |
| 260 | 0 | i-Pr | i-Pr | OMe | Cl | Br | A | 2.82 | 626 |
| 261 | 0 | Et | CH═CH₂ | Me | H | Br | | logP: 2.1 [pH = 10.0]; m.p: 60° C. | |
| 262 | 0 | | CH₂CH₂CH₂CH₂ | Me | CN | Br | | m.p: 85° C. | |
| 263 | 0 | n-Pr | Me | Me | H | Br | | logP: 2.3 [pH = 10.0]; m.p: 150° C. | |
| 264 | 1 | Me | Me | Me | Cl | Br | B | 1.21 | 543.9 |
| 265 | 0 | | CH₂CH₂CH₂CH₂ | Br | F | Br | A | 3.012 | 603.70 |
| 266 | 0 | | CH₂CH₂SCH₂ | Me | CN | Br | A | 3.199 | 564.90 |
| 267 | 0 | | CH₂CH₂CH₂CH₂ | Me | I | Br | | logP: 3.4 [pH = 10.0]; m.p: 213° C. | |
| 268 | 0 | CH₂CH₂Cl | Et | Me | I | Br | | logP: 3.2 [pH = 10.0]; m.p: 80° C. | |
| 269 | 0 | | CH₂CH₂CH₂CH₂ | Me | Cl | Br | A | 3.277 | 556.00 |
| 270 | 0 | Et | Me | Me | H | Br | | logP: 2 [pH = 10.0]; m.p: 161° C. | |
| 271 | 0 | | CH₂CH₂SCH₂ | Me | Cl | Br | A | 3.399 | 573.85 |
| 272 | 0 | Me | n-Pr | Me | I | Br | | logP: 3.2 [pH = 10.0] | |
| 273 | 0 | | CH₂CH₂SCH₂ | Cl | Cl | Br | A | 3.408 | 593.85 |
| 274 | 0 | Me | Me | Me | H | Br | | logP: 1.9 [pH = 10.0]; m.p: 200° C. | |

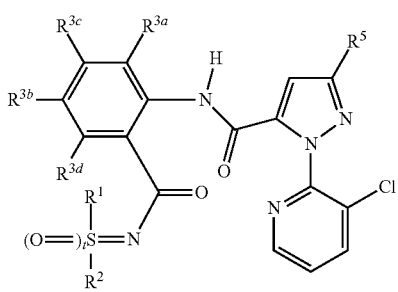

(V-B)

Compounds V-B are compounds of the formula V with $R^6$=Cl, $R^4$=H and Q=N.

| # | t | $R^1$ | $R^2$ | $R^{3a}$ | $R^{3c}$ | $R^{3b}$ | $R^{3d}$ | $R^5$ | MS | RT[min] | m/z |
|---|---|---|---|---|---|---|---|---|---|---|---|
| 275 | 0 | Et | Et | Me | Cl | H | H | $CF_3$ | B | 1.208 | 546 |
| 276 | 0 | i-Pr | i-Pr | Me | Me | H | H | $CF_3$ | B | 1.13 | 554 |
| 277 | 0 | i-Pr | i-Pr | Me | Cl | H | H | $CF_3$ | B | 1.298 | 574 |
| 278 | 0 | i-Pr | i-Pr | Me | H | —CH=N—NH— | | OMe | B | 1.076 | 542.2 |
| 279 | 0 | $CH_2CH_2SCH_2$ | | H | H | —CH=N—NH— | | $CF_3$ | A | 3.570 | 554.9 |
| 280 | 0 | Et | Et | Me | H | H | Me | $CF_3$ | B | 1.004 | 526 |
| 281 | 0 | Et | Et | Me | H | —CH=N—NH— | | OMe | B | 0.992 | 514.3 |
| 282 | 0 | i-Pr | i-Pr | Me | H | H | Me | $CF_3$ | B | 1.056 | 554 |
| 283 | 0 | Et | Et | Me | Me | H | H | $CF_3$ | B | 1.073 | 526 |

B. Biological Examples

The activity of the compounds of formula I of the present invention can be demonstrated and evaluated in biological tests described in the following.

If not otherwise specified the test solutions are prepared as follow:

The active compound is dissolved at the desired concentration in a mixture of 1:1 (vol:vol) distilled water:aceton. The test solution is prepared at the day of use and in general at concentrations of ppm (wt/vol).

B.1 Green Peach Aphid (*Myzus persicae*)

The active compounds are formulated in cyclohexanone as a 10,000 ppm solution supplied in tubes. The tubes are inserted into an automated electrostatic sprayer equipped with an atomizing nozzle and they served as stock solutions for which lower dilutions are made in 50% acetone:50% water (v/v). A nonionic surfactant (Kinetic®) is included in the solution at a volume of 0.01% (v/v).

Bell pepper plants at the first true-leaf stage are infested prior to treatment by placing heavily infested leaves from the main colony on top of the treatment plants. Aphids are allowed to transfer overnight to accomplish an infestation of 30-50 aphids per plant and the host leaves are removed. The infested plants are then sprayed by an automated electrostatic plant sprayer equipped with an atomizing spray nozzle. The plants are dried in the sprayer fume hood, removed, and then maintained in a growth room under fluorescent lighting in a 24-hr photoperiod at about 25° C. and about 20-40% relative humidity. Aphid mortality on the treated plants, relative to mortality on untreated control plants, is determined after 5 days.

In this test, compounds S.9, S.10 and S.11, respectively, at 2500 ppm showed over 75% mortality in comparison with untreated controls.

B.2 Vetch Aphid (*Megoura viciae*)

For evaluating control of vetch aphid (*Megoura viciae*) through contact or systemic means the test unit consists of 24-well-microtiter plates containing broad bean leaf disks. The compounds are formulated using a solution containing 75% v/v water and 25% v/v DMSO. Different concentrations of formulated compounds are sprayed onto the leaf disks at 2.5 μl, using a custom built micro atomizer, at two replications.

After application, the leaf disks are air-dried and 5-8 adult aphids placed on the leaf disks inside the microtiter plate wells. The aphids are then allowed to suck on the treated leaf disks and incubated at about 23±1° C. and about 50±5% relative humidity for 5 days. Aphid mortality and fecundity is then visually assessed.

In this test, compound S.9 at 1415 ppm showed over 75% mortality in comparison with untreated controls.

B.3 Tobacco Budworm (*Heliothis virescens*) I

The active compounds are formulated in cyclohexanone as a 10,000 ppm solution supplied in tubes. The tubes are inserted into an automated electrostatic sprayer equipped with an atomizing nozzle and they serve as stock solutions for which lower dilutions are made in 50% acetone:50% water (v/v). A nonionic surfactant (Kinetic®) is included in the solution at a volume of 0.01% (v/v).

Cotton plants are grown 2 plants to a pot and selected for treatment at the cotyledon stage. Test solutions are sprayed onto the foliage by an automated electrostatic plant sprayer equipped with an atomizing spray nozzle. The plants are dried in the sprayer fume hood and then removed from the sprayer. Each pot is placed into perforated plastic bags with a zip closure. About 10 to 11 budworm larvae are placed into the bag and the bags zipped closed. Test plants are maintained in a growth room at about 25° C. and about 20-40% relative humidity for 4 days, avoiding direct exposure to fluorescent light (24 hour photoperiod) to prevent trapping of heat inside the bags. Mortality and reduced feeding are assessed 4 days after treatment, compared to untreated control plants.

In this test, compounds S.7, S.9, S.10, S.11, S.14, S.20 and S.23 respectively, at 1415 ppm showed over 75% mortality in comparison with untreated controls.

In this test, the compound and S.22, at 800 ppm showed over 75% mortality in comparison with untreated controls.

B.4 Cowpea Aphid (*Aphis craccivora*)

The active compound is dissolved at the desired concentration in a mixture of 1:1 (vol:vol) distilled water: acetone. Surfactant (Alkamuls® EL 620) is added at a rate of 0.1% (vol/vol). The test solution is prepared at the day of use.

Potted cowpea plants were colonized with approximately 50 to 100 aphids of various stages by manually transferring a leaf tissue cut from infested plant 24 hours before application. Plants were sprayed after the pest population has been recorded. Treated plants are maintained on light carts at about 28° C. Percent mortality was assessed after 72 hours.

In this test, compounds S.15 and S.23, respectively, at 500 ppm showed over 75% mortality in comparison with untreated controls.

B.4 Orchid Thrips (*Dichromothrips corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus 0.01% vol/vol Alkamuls® EL 620 surfactant.

Thrips potency of each compound was evaluated by using a floral-immersion technique. Plastic petri dishes were used as test arenas. All petals of individual, intact orchid flowers were dipped into treatment solution and allowed to dry. Treated flowers were placed into individual petri dishes along with about 20 adult thrips. The petri dishes were then covered with lids. All test arenas were held under continuous light and a temperature of about 28° C. for duration of the assay. After 3 days, the numbers of live thrips were counted on each flower, and along inner walls of each petri dish. The percent mortality was recorded 72 hours after treatment.

In this test, compounds S.12, S.14, S.15, S.17 and S.22, respectively, at 500 ppm showed over 75% mortality in comparison with untreated controls.

The invention claimed is

1. A compound of the formula (I)

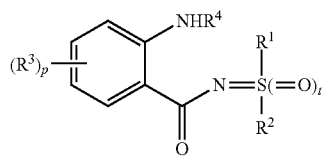

in which
t is 0 or 1;
p is 0, 1, 2, 3 or 4;
$R^1$ and $R^2$ are selected, independently of one another, from the group consisting of hydrogen, $C_1$-$C_{10}$-alkyl, $C_1$-$C_{10}$-haloalkyl, $C_3$-$C_{10}$-cycloalkyl, $C_3$-$C_{10}$-halocycloalkyl, $C_2$-$C_{10}$-alkenyl, $C_2$-$C_{10}$-haloalkenyl, $C_2$-$C_{10}$-alkynyl, and $C_2$-$C_{10}$-haloalkynyl, wherein the eight last radicals may optionally be substituted by one or more radicals $R^a$, or $R^1$ and $R^2$ together represent a $C_2$-$C_9$-alkylene, $C_2$-$C_9$-alkenylene or $C_6$-$C_9$-alkynylene chain forming together with the sulfur atom to which they are attached a 3-, 4-, 5-, 6-, 7-, 8-, 9- or 10-membered saturated, partially unsaturated or fully unsaturated ring, wherein 1 to 4 of the $CH_2$ groups in the $C_2$-$C_9$-alkylene chain or 1 to 4 of any of the $CH_2$ or CH groups in the $C_2$-$C_9$-alkenylene chain or 1 to 4 of any of the $CH_2$ groups in the $C_6$-$C_9$-alkynylene chain may be replaced by 1 to 4 groups independently selected from the group consisting of C=O, C=S, O, S, N, NO, SO, $SO_2$ and $NR^y$, and wherein the carbon atoms in the $C_2$-$C_9$-alkylene, $C_2$-$C_9$-alkenylene or $C_6$-$C_9$-alkynylene chain may be substituted with 1 to 5 identical or different substituents $R^x$, and wherein the sulfur and nitrogen atoms in the $C_2$-$C_9$-alkylene, $C_2$-$C_9$-alkenylene or $C_6$-$C_9$-alkynylene chain, independently of one another, may be oxidized;

$R^3$ if present, are independently selected from the group consisting of halogen, cyano, azido, nitro, —SCN, $SF_5$, $C_1$-$C_8$-alkyl, $C_1$-$C_8$-haloalkyl, $C_3$-$C_8$-cycloalkyl, $C_3$-$C_8$-halocycloalkyl, $C_2$-$C_8$-alkenyl, $C_2$-$C_8$-haloalkenyl, $C_2$-$C_8$-alkynyl, $C_2$-$C_8$-haloalkynyl, wherein the eight last radicals may optionally be substituted by one or more radicals $R^a$, —$OR^b$, $SR^b$, —$S(O)_mR^b$, —$S(O)_nN(R^c)R^d$, —$N(R^c)R^d$, —$Si(R^f)_2R^g$, —$N(R^c)C(=O)R^b$, —$C(=NR^c)R^b$, —$C(=O)N(R^c)R^d$, —$C(=S)N(R^c)R^d$, phenyl which may be substituted by 1, 2, 3, 4 or 5 radicals $R^e$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^e$, for p>1 it being possible that $R^3$ are identical or different,
or two radicals $R^3$ bound on adjacent carbon atoms may be together a group selected from the group consisting of —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —$OCH_2OCH_2$—, —$CH_2CH_2CH_2$—, —CH=$CHCH_2$—, —$CH_2CH_2O$—, —CH=CHO—, —$CH_2OCH_2$—, —$CH_2C(=O)O$—, —C(=O)$OCH_2$—, —O($CH_2$)O—, —$SCH_2CH_2CH_2$—, —SCH=$CHCH_2$—, —$CH_2SCH_2CH_2$—, —$SCH_2CH_2S$—, —$SCH_2SCH_2$—, —$CH_2CH_2S$—, —CH=CHS—, —$CH_2SCH_2$—, —$CH_2C(=S)S$—, —C(=S)$SCH_2$—, —S($CH_2$)S—, —$CH_2CH_2NR^y$—, —$CH_2CH=N$—, —CH=CH—$NR^y$—, —CH=N—$NR^y$—, —OCH=N— and —SCH=N—, thus forming, together with the carbon atoms to which they are bound, a 5- or 6-membered ring, where the hydrogen atoms of the above groups may be replaced by one or more substituents selected from the group consisting of halogen, methyl, halomethyl, hydroxyl, methoxy and halomethoxy or one or more $CH_2$ groups of the above groups may be replaced by a C=O group;

$R^4$ is selected from the group consisting of hydrogen, $C_1$-$C_{10}$-alkyl, $C_1$-$C_{10}$-haloalkyl, $C_3$-$C_8$-cycloalkyl, $C_3$-$C_8$-halocycloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, and phenyl;

$R^a$ is selected from the group consisting of cyano, azido, nitro, —SCN, $SF_5$, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —$Si(R^f)_2R^g$, —$OR^b$, —$SR^b$, —$S(O)_mR^b$, —$S(O)_nN(R^c)R^d$, —$N(R)R^d$, —$C(=O)R^b$, $C(=O)OR^b$, $C(=O)N(R^c)R^d$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^e$;

or two geminally bound radicals $R^a$ together form a group selected from =$CR^hR^k$, =$NR^c$, =$NOR^b$ and =$NNR^c$;
or two radicals $R^a$, together with the carbon atoms to which they are bound, form a 3-, 4-, 5-, 6-, 7- or 8-membered saturated or partially unsaturated carbocyclic ring or a 3-, 4-, 5-, 6-, 7- or 8-membered saturated or partially unsaturated heterocyclic ring containing 1, 2 or 3 heteroatoms or heteroatom groups selected from the group consisting of N, O, S, NO, SO and $SO_2$, as ring members;

wherein, in the case of more than one $R^a$, $R^a$ can be identical or different;

$R^b$ is selected from the group consisting of hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, where the five last mentioned radicals may be unsubstituted, partially or fully halogenated and/or wherein one or two $CH_2$ groups may be replaced by a CO group; and/or may carry 1-2 radicals selected from $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkoxycarbonyl, —Si($R^f$)$_2$$R^g$, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and $C_1$-$C_6$-alkoxycarbonyl;

wherein, in the case of more than one $R^b$, $R^b$ can be identical or different;

$R^c$, $R^d$ are, independently from one another, selected from the group consisting of hydrogen, cyano, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, where the five last mentioned radicals may be unsubstituted, partially or fully halogenated and/or wherein one or two $CH_2$ groups may be replaced by a CO group; and/or may carry 1 or 2 radicals selected from $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-alkoxycarbonyl, —Si($R^f$)$_2$$R^g$, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and $C_1$-$C_6$-alkoxycarbonyl;

or $R^c$ and $R^d$, together with the nitrogen atom to which they are bound, form a 3-, 4-, 5-, 6- or 7-membered saturated, partly unsaturated or completely unsaturated N-heterocyclic ring which may contain 1 or 2 further heteroatoms selected from the group consisting of N, O and S as ring members, where the heterocyclic ring may carry 1, 2, 3 or 4 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^e$ is selected from the group consisting of halogen, cyano, $C_1$-$C_6$-alkyl, $C_2$-$C_6$-alkenyl, $C_2$-$C_6$-alkynyl and $C_3$-$C_8$-cycloalkyl, where the four last-mentioned radicals may be unsubstituted, partially or fully halogenated and/or wherein one or two $CH_2$ groups may be replaced by a CO group, and/or may carry 1-2 radicals selected from $C_1$-$C_4$-alkoxy, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkoxycarbonyl, —Si($R^f$)$_2$$R^g$, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$haloalkoxy and $C_1$-$C_6$-alkoxycarbonyl;

wherein, in the case of more than one $R^e$, $R^e$ can be identical or different;

$R^f$, $R^g$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, $C_3$-$C_8$-cycloalkyl-$C_1$-$C_4$-alkyl, phenyl and benzyl;

$R^h$, $R^k$ are, independently from one another, selected from the group consisting of hydrogen, halogen, cyano, azido, nitro, —SCN, SF$_5$, $C_1$-$C_6$-alkyl, $C_2$-$C_6$-alkenyl, $C_2$-$C_6$-alkynyl and $C_3$-$C_8$-cycloalkyl, where the four last mentioned radicals may be unsubstituted, partially or fully halogenated and/or oxgenated, and/or may carry 1 or 2 radicals selected from $C_1$-$C_4$-alkyl; $C_1$-$C_4$-haloalkyl; $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, —Si($R^f$)$_2$$R^g$, —OH, —SH, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$haloalkoxy; ($C_1$-$C_6$-alkoxy)carbonyl, ($C_1$-$C_6$-alkyl)amino, and di-($C_1$-$C_6$-alkyl)amino;

or $R^h$ and $R^k$ together form a group =C($C_1$-$C_4$-alkyl)$_2$, =N($C_1$-$C_6$-alkyl), =NO($C_1$-$C_6$-alkyl), or =O;

$R^x$ is selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl and $C_2$-$C_6$-haloalkynyl, said substituents $R^x$ being identical or different from one another if more than one substituent $R^x$ is present;

$R^y$ is selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl and $C_3$-$C_8$-cycloalkyl-$C_1$-$C_4$-alkyl;

m is 1 or 2, wherein, in the case of several occurrences, m may be identical or different.

n is 0, 1 or 2; wherein, in the case of several occurrences, n may be identical or different;

or a salt thereof.

2. The compound as claimed in claim 1, where t is 0.

3. The compound as claimed in claim 1, where $R^1$ and $R^2$, independently of each other, are selected from the group consisting of $C_1$-$C_6$-alkyl, $C_3$-$C_7$-cycloalkyl and $C_3$-$C_8$-cycloalkyl-$C_1$-$C_4$-alkyl or $R^1$ and $R^2$ together represent a $C_3$-$C_7$-alkylene or $C_3$-$C_7$-alkenylene forming together with the sulfur atom to which they are attached a 4-, 5-, 6-, 7- or 8-membered saturated or partially unsaturated ring, wherein 1 or 2 of the $CH_2$ groups in the $C_3$-$C_7$-alkylene chain or 1 or 2 of any of the $CH_2$ or CH groups in the $C_3$-$C_7$-alkenylene chain may be replaced may be replaced by 1 or 2 groups independently selected from the group consisting of O, S and NR$^y$, and wherein the carbon atoms in the $C_3$-$C_7$-alkylene or $C_3$-$C_7$-alkenylene chain may be substituted with 1 to 5 identical or different substituents $R^x$.

4. The compound as claimed in claim 1, where p is 0, 1 or 2.

5. The compound as claimed in claim 1, where $R^3$ is selected from the group consisting of halogen, methyl, cyano and halomethyl, for p>1 it being possible that $R^3$ are identical or different.

6. The compound as claimed in claim 1, where $R^4$ is hydrogen.

7. The compound as claimed in claim 1, which is represented by the following formula Ia:

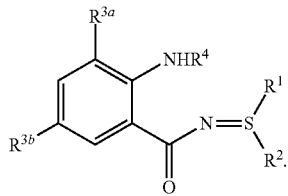

8. The compound as claimed in claim 7, where $R^{3a}$ is selected from the group consisting of hydrogen, halogen, methyl and halomethyl and where $R^{3b}$ is selected from the group consisting of hydrogen, halogen, methyl, cyano and halomethyl.

9. A process for preparing a compound of the formula I according to claim 1, which comprises reacting a compound of the formula II with a compound of the formulae III or IV:

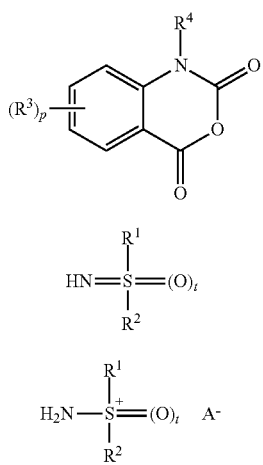

where $A^-$ is an equivalent of an anion having a $pK_B$ of at least 10 (determined under standard conditions in water).

10. The process as claimed in claim 9, where the reaction of the compound of the formula II with the compound of the formulae III or IV is performed in the presence of a base.

11. The process as claimed in claim 10, where the base is selected from the group consisting of alkalimetal alkanolates and tertiary amines.

12. A method for controlling invertebrate pest, which method comprises contacting the invertebrate pest or their food supply, habitat, breeding grounds or their locus with a compound of claim 1 in a pesticidally effective amount.

13. A method for controlling invertebrate pest, which method comprises contacting the invertebrate pest or their food supply, habitat, breeding grounds or their locus with a compound of claim 2 in a pesticidally effective amount.

14. A method for controlling invertebrate pest, which method comprises contacting the invertebrate pest or their food supply, habitat, breeding grounds or their locus with a compound of claim 3 in a pesticidally effective amount.

15. A method for controlling invertebrate pest, which method comprises contacting the invertebrate pest or their food supply, habitat, breeding grounds or their locus with a compound of claim 4 in a pesticidally effective amount.

16. A method for controlling invertebrate pest, which method comprises contacting the invertebrate pest or their food supply, habitat, breeding grounds or their locus with a compound of claim 5 in a pesticidally effective amount.

17. A method for controlling invertebrate pest, which method comprises contacting the invertebrate pest or their food supply, habitat, breeding grounds or their locus with a compound of claim 6 in a pesticidally effective amount.

18. A method for controlling invertebrate pest, which method comprises contacting the invertebrate pest or their food supply, habitat, breeding grounds or their locus with a compound of claim 7 in a pesticidally effective amount.

19. A method for controlling invertebrate pest, which method comprises contacting the invertebrate pest or their food supply, habitat, breeding grounds or their locus with a compound of claim 8 in a pesticidally effective amount.

\* \* \* \* \*